US007176006B2

(12) United States Patent
Jefferson et al.

(10) Patent No.: US 7,176,006 B2

(45) Date of Patent: Feb. 13, 2007

(54) MICROBIAL β-GLUCURONIDASE GENES, GENE PRODUCTS AND USES THEREOF

(75) Inventors: Richard A. Jefferson, Googong (AU); Jorge E. Mayer, Canberra (AU)

(73) Assignee: Cambia, Act (AU)

(*) Notice: Subject to any disclaimer, the term of this patent is extended or adjusted under 35 U.S.C. 154(b) by 117 days.

(21) Appl. No.: 10/364,649

(22) Filed: Feb. 12, 2003

(65) Prior Publication Data

US 2003/0229921 A1 Dec. 11, 2003

Related U.S. Application Data

(63) Continuation of application No. 09/270,957, filed on Mar. 17, 1999, now Pat. No. 6,641,996, which is a continuation-in-part of application No. 09/149,727, filed on Sep. 8, 1998, now Pat. No. 6,391,547.

(60) Provisional application No. 60/058,263, filed on Sep. 9, 1997.

(51) Int. Cl.
*C12N 9/00* (2006.01)
*C07K 1/00* (2006.01)

(52) U.S. Cl. ...................................... 435/183; 530/350

(58) Field of Classification Search ................ 435/183; 530/350

See application file for complete search history.

(56) References Cited

U.S. PATENT DOCUMENTS

| | | | |
|---|---|---|---|
| 5,252,484 | A | 10/1993 | Matner et al. |
| 5,599,670 | A | 2/1997 | Jefferson |

FOREIGN PATENT DOCUMENTS

| | | | |
|---|---|---|---|
| EP | 297 944 B1 | 1/1989 | |
| EP | 601 092 B1 | 6/1994 | |
| GB | 2 197 653 A | 5/1998 | |
| JP | 4023982 A | 1/1992 | |
| JP | 4267876 A | 9/1992 | |
| JP | 6256196 A | 9/1994 | |
| JP | 7274948 A | 10/1995 | |
| WO | WO 89 03880 | 5/1989 | |
| WO | WO 96/37609 | 11/1996 | |
| WO | WO 99 13085 | 3/1999 | |

OTHER PUBLICATIONS

Burchhardt et al (Gene vol. 106, pp. 13-19, 1991).*

Ogushi et al (Agricultural and Biological Chemistry vol. 50, No. 12, pp. 3093-3100, 1986).*

Akao et al., "Glycyrrhizin β-D-Glucuronidase of *Eubacterium* sp. from Human Intestinal Flora," Chem. Pharm. Bull. 35(2): 705-710, 1987.

Akao, "Purification and Characterization of Glycyrrhetic Acid Mono-glucuronide β-D-Glucuronidase in *Eubacterium* sp. GLH," Biol. Pharm. Bull. 22(1): 80-82, 1999.

Blattner et al., "The Complete Genome Sequence of *Escherichia coli* K-12," Science 277: 1453-1462, 1997 (+ Database EMBL—EMPRO Entry ECAE257, Acc. No. AE000257; U00096, Jan. 29, 1997).

Dean et al., "Iodinated fibroblast β-glucuronidase as a ligand for receptor-mediated endocytosis," Biochem. J. 229: 213-219, 1985.

Denecke et al., "Protein Secretion in Plant Cells Can Occur via a Default Pathway," The Plant Cell 2: 51-59, 1990.

Fan et al., "Determination and comparison of β-glucuronidase activity among strains of *B. fragilis* and *E. coli*," Hua.His.I.Ko.Ta. Hseuh.Pao. 22(2): 211-212, 1991.

Firek et al., "Endoplasmic Reticulum Targeting of Active Modified β-Glucuronidase (GUS) in Transgenic Tobacco Plants," Transgenic Research 3: 326-331, 1994.

Ikeda et al., "Variations in concentrations of bacterial metabolites, enzyme activities, moisture, pH and bacterial composition between and within individuals in faeces of seven healthy adults," Journal of Applied Bacteriology 77: 185-194, 1994.

Islam et al., "C-terminal Processing of Human β-Glucuronidase. The Propetide is Required for Full Expression of Catalytic Activity, Intracellular Retention, and Proper Phosphorylation," J. Bio. Chem. 268(30): 22627-22633, 1993.

Jain et al., "Structure of human β-glucuronidase reveals candidate lysosomal targeting and active-site motifs," Nat. Struct. Bio. 3(4): 375-381, 1996.

Jefferson et al., "Beta glucuronidase from *Escherichia coli* as a gene-fusion marker," PNAS vol. 83: 8447-8451, Nov. 1986.

Jefferson et al., "GUS fusions : β-glucuronidase as a sensitive and versatile gene fusion marker in higher plants," The EMBO Journal 6(13): 3901-3907, 1987.

Kelley et al., "Influence of Hypercholesterolemia and Cholesterol Accumulation on Rabbit Carrageenan Granuloma Macrophage Activation," American Journal of Pathology 131(3): 539-546, 1988.

Khasanov et al., "Determination of the minimal length DNA homologous region required for plasmid integration into the Baccillus subtillis chromosome via homologous recombination," Genetika (Russia) vol. 28(7): 38-45, 1992.

Nelson Ke et al., "*Thermotoga maritime* beta-glucuronidase," Database PIR2 'Online' EMBL, Heidelberg, Germany; ID/AC AE001766; Q9XOF2, Jun. 4, 1999, nucleotides 4542-6233.

Nelson Ke et al., "Evidence for lateral gene transfer between Archaea and Bacteria from genome sequence of *Thermotoga maritime*," Nature 399: 323-329, 1999.

Russell WM and Klaenhammer TR, "Identification and Cloning of *gus*A, Encoding a New β-Glucuronidase from *Lactobacillus gasseri* ADH," Applied and Environmental Microbiology 67: 1253-1261, 2001.

Sakaguchi and Murata, "β-Glucuronidase of Clostridium Perfringens," Zbl. Bakt. Hyg. A 257: 308-316, 1984.

(Continued)

*Primary Examiner*—Mark Navarro

(74) *Attorney, Agent, or Firm*—Cougar Patent Law; Carol Nottenburg

(57) ABSTRACT

Genes encoding microbial β-glucuronidases and proteins and their uses are provided.

3 Claims, 33 Drawing Sheets

OTHER PUBLICATIONS

Tapsall and McIver, "β-D- Glucuronidase Activity Among Prototrophic and Auxotrophic Variants of *Escherichia coli* and Other *Enterobacteriaceae* Commonly Implicated in Urinary Tract Infections,"Diagn. Microbiol. Infect. Dis. 22: 261-266, 1995.

Wheeler et al., "*N*-Acetyl- β-glucosaminidase, β-Glucuronidase and Acid Phosphatase in *Mycobacterium leprae*," Journal of General Microbiology 128: 1063-1071.

Wilson et al., "GUS Protocols: Using the GUS Genes as a Reporter of Gene Expression," Academic Press, Inc., San Diego, 1992, Chapter 1, "The *Escherichia coli* gus Operan: Induction and Expression of the *gus* Operon in *E. coli* and the Occurrences and Use of Gus in Other Bacteria," pp. 7-22.

Wong et al., "Identification of Glu-540 as the Catalytic Nucleophile of Human β-Glucuronidase Using Electrospray Mass Spectrometry," The Journal of Biological Chemistry 213(51): 34057-34062, 1998.

Yan et al., "Gene Fusions of Signal Sequences with a Modified β-Glucuronidase Gene Results in Retention of the β-Glucuronidase Protein in the Secretory Pathway/Plasma Membrane," Plant. Physiol. 115(3): 915-924, 1997.

* cited by examiner

FIG. 1A 1 aagcttgagc ggtcatatct gccccaccca cgctcgcgtc ccaatttatt catgacttgc
61 tgggtaggcg ggaaaaactt ttcggccgct gcttcagtac tctccgcaat gaaaccatgg
121 gaatgggaag caaccggcaa ctttgacacg tcatgacctg catgagcggc tgcctttttta
181 tagagcctca caagtggctc aaactgcagt gggcggcccc caataatggc tagaactagt
241 ggcaagccaa gcaggccagc acggatgacg gaatcctgac tgccgccact gccaatccaa
301 acaggtaaag gatcctgaac aggtcttggg tacacaccga gattctggat ggccggccga
361 tgtccgcctt tccagttcac cttctcggac tcccgtattt ttaacaaaag ctccagtttc
421 tcatcgaata attcatcata gtcttttaaa tcatagccaa acagcggaaa ggattcgata
481 aaggagcctc gccctgccat aatctctgca cgtccattcg atatggcatc gagggtagca
541 aaatcctgaa atactcggac tggatcagca gaagatagaa ccgtcaccgc acttgttaaa
601 cgaatccgtt ttgtctgcca agcagcggca gccaatagaa ctgctggaga tgatgccgca
661 aaatcttcgc gatgatgctc accaacacca aagacatcca gcaatacctc gtctgcgagt
721 acaatttcct caaccacttc ccgaatccgt tgggaatgac tcatcacttc accggtttca
781 acatccggtg ttgtctctac gaacgtgctt atacctattt ccacaatcat tacctcctat
841 gtataatcgt ttgctcttgt gccaaagcta tatgaatttc ttattattgc tgactttttc
901 accatatata taaatgaaag aatatttcaa acgttattat cttatatttt cctatttatt
961 tcaaaaaaat tgtttaacta gcgaaagtag gactaccata caaaatgccc atgttgaaca
1021 aaacaaagca tttttttccgc cgttgtttca tacataagaa aggtgcatga ttaagaaatt
1081 ctataaaggc gcaccgagga ggacaatgat gattcaacaa accgttatga ttaacagaga
1141 agcaggttta tatgctcagc cagtcaatca attagtgcaa acagcttcac aattcaatgc
1201 tgatatcttt ctttcataca aaggacgaaa ggttagtgtg aaatcggtac tcggcgtttt
1261 atcgttagcg atacctaaac aggccgaaat tatcttagaa gtttccggag atgatgaaaa
1321 agaagcactc aaaggggtta tcaatgcgtt ggagaaatta gactagggtt ttcccttttt
1381 aatagggaat caccttgaca ttgaaaaagt ataagaaaat gaaaatagga aaaaccaatg
1441 acttaagggg agtctctatt ggaaagagac tccccttatt caacattaga acgaaattag
1501 agcctttact tttctttcaa cttttcatcc cgatactttt ttgtaatagt tttttcatt
1561 aataatacaa gtcctgattt tgcaagaata atcctttta gataaaaata tctatgctaa
1621 taataacatg taaccactta catttaaaaa ggagtgctat catgttatat ccaatcaata
1681 cagaaacccg aggagttttt gatttaaatg gggtctggaa ttttaaatta gattacggca
1741 aaggactgga agaaaagtgg tatgaatcaa aactgacaga taccatatca atggctgtac
1801 cttcctccta taatgatatc ggtgttacga aggaaattcg aaaccatatc ggctatgtat
1861 ggtacgagcg tgaatttacc gttcctgctt atttaaaaga tcagcgcatc gtcctgcgtt
1921 ttggttcagc aacacataag gctattgtat acgttaacgg agaactagta gttgaacaca
1981 aaggcggctt cttaccgttt gaggcagaaa taaacaacag cttaagagac ggaatgaatc
2041 gtgtaacagt agcggttgat aatattttag atgattctac gctcccagtt gggctatata
2101 gtgaaagaca tgaagaaggt ttgggaaaag tgattcgtaa taaacctaat tttgacttct
2161 ttaactatgc aggcttacat cgtcctgtaa aaatttatac aacccctttt acctatgttg
2221 aggatatatc ggttgtaacc gattttaacg gtccaacggg aacagttacg tatacagttg
2281 attttcaggg taaggcagaa accgtaaagg ttagtgtagt tgatgaagaa gggaaagttg
2341 ttgcttcaac tgaaggcctc tctggtaatg ttgagattcc taacgttatc ctttgggaac
2401 ctttaaatac ctatctctat caaattaaag ttgagttagt aaatgatggt ctaactattg
2461 atgtatacga agagccattt ggagttcgaa ccgttgaagt aaacgacggg aaattcctca
2521 ttaataacaa accattttat tttaaagggt tcggaaaaca cgaggatact ccaataaatg
2581 gaagaggctt taatgaagca tcaaatgtaa tggattttaa tattttgaaa tggatcggtg
2641 cgaattcctt tcggacggcg cactatcctt attctgaaga actgatgcgg ctcgcagatc
2701 gtgaagggtt agtcgtcata gatgaaaccc cagcagttgg tgttcatttg aactttatgg
2761 caacgactgg tttgggcgaa ggttcagaga gagtgagtac ttgggaaaaa atccggacct
2821 ttgaacatca tcaagatgta ctgagagagc tggtttctcg tgataaaaac cacccctctg
2881 ttgtcatgtg gtcgattgca aatgaagcgg ctacggaaga agaaggcgct tatgaatact

FIG. 1B 2941 ttaagccatt agttgaatta acgaaagaat tagatccaca aaaacgccca gttaccattg
3001 ttttgttcgt aatggcgaca ccagaaacag ataaagtggc ggagttaatt gatgtgattg
3061 cattgaatcg atacaacggc tggtattttg atgggggtga tcttgaagcc gcgaaagtcc
3121 accttcgtca ggaatttcat gcgtggaata aacgctgtcc aggaaaacct ataatgataa
3181 cagagtatgg ggctgatacc gtagctggtt ttcatgatat tgatccggtt atgtttacag
3241 aagagtatca ggttgaatat taccaagcaa atcatgtagt atttgatgaa tttgagaact
3301 ttgttggcga gcaggcctgg aattttgcag actttgctac aagccagggt gtcatgcgtg
3361 ttcaaggtaa caaaaaaggt gttttcacac gcgaccgcaa accaaaatta gcagcacatg
3421 ttttccgcga acgttggaca aacatcccgg atttcggtta taaaaattaa taaaaagctg
3481 gttctccaat aggaggccag ctttttttaca tggatacaat ggttgtaaat taaaaaccct
3541 cttcattttt tatataaaaa tgaagagggt tttaattttt taaatgttat tacattttttt
3601 ctaagcccac tcatacaata tgggactttg gatagcatgg gaaacagctt ttttagactg
3661 tagttttcca gtcagctgca aatttttcaa ttccttggtc tgttaaagga tgttttgata
3721 attgctcaat taccttgaat ggaatcgttg caatatgagc tccagccatc gccacacgtg
3781 taacatgatc tggatgacga acagatgcag caatgatttg tgaatccaag ttttgaatct
3841 ggaacatctt agcaattttt gcgactaatt ctacaccatc ttcgttaata tcatctaacc
3901 tgcctaagaa tggtgaaaca taagttgcac ctgctcgtgc tgccagcaat gcctggttaa
3961 cactaaaaat caaagtaacg ttggttttta caccttttttt cgttagataa cggcaagcct
4021 ctagtccatc taacgtcatc ggaagtttaa ttgtaatatt tttatcgccg ccgttaattt
4081 taatgagctc atttgcttca gcaatcattt gatcagctgt caaagcatta ggtgttactt
4141 cggcagaaac agactcaacc tcgggtacgg cattaaggat ttcagcaata cggtcctcaa
4201 atttcacgcc ctctttagct actaaagaag ggttcgttgt tactcctgat aacacgccaa
4261 ttttataggc ttttttgatt tcctctaggt tggcagtatc gataaaaaat ttcataatgt
4321 ttttcctcca atttttagta aagtaatttt tcgtttctaa agcatgtccc caacggaaat
4381 taggttattg aatataatat aggttacttt ccgttaccat aatataacta tccgacaata
4441 atcgtcaagt aaaatgtctt gaattaaaga tatttatttt tttcaaaaga tactatttac
4501 tttactttat tgataagaat tcacgcatcc taactaggat ggcgtgaatt aactttcctt
4561 attcgacaac tccatctcgt tattgtgagg gagtacttcc tgtttctttt ttaaatactc
4621 ttgcaaagta ggagggatca tcatagccaa tcgtccaggc gatttcctct acggataaat
4681 tctctgtttt taaaaggtgc ttggcttgct tcattcgtaa tatttgctga aaagcggtta
4741 aggtcatctt tgtttcgtct ttaaattttc gggaaagatg acttggatgg gtagacaatt
4801 gtgctgccaa ttcttcttta ttgatttgct tattataaaa acttagcagg tgttcaatca
4861 ccctttgggt catgtttgta tagctactta atgaattgga aatgattaaa tcgcaatatt
4921 cctcaatcat acaatcttct aattgatgca gtacttctag ttgattagca ttttcgattt
4981 cgtaagcata tttttccgaa attcgatgaa taatgatggc aggtacttgg ctgtttcttg
5041 ctgacgtacg gagaagtatt taatataatc gctacatttt ttagtctgcg caacggctga
5101 ttgggaaatc gttcctaaaa agaaaacagc atatttttag aattaatgag ctgtaatgcc
5161 atttttttat ctccacgctc aacggcatgc atgaaatctt ttcagtcttg taccttaatt
5221 tgactagttc cgcttcttca tccacgttaa gatgattcac tttattgtga ataggacggt
5281 tgtttttatc agaaacaatg acaaacgggg taatctcttc ctccaacatg tgtggaaact
5341 gctgaaggat gcttgcataa ctgctggcct gttcagcggt tagtacataa attttatcgc
5401 ttataagcat taaatcttca ctttgtggac ttgtgagacg atattccttt gataaactgt
5461 atagattcgg tgtcttatca aaatatggtc cgatgataat ggtgtaggct gcctgctttt
5521 gggtgaagga atatccgaaa tagtgtaagt cccattcgtt tatataagaa tataattggt
5581 cctgatgctt catttttttcg aacaaattca gtggatcttc tttctctgaa cctggcataa
5641 atagcgggat tgcaatgatt tcatgatggt acacaaactc cccattttga tctaaaacat
5701 atgtatttaa attggttata tggtggattt tcatagtggt tgagatgatt tttggttgtt
5761 ccatctgatt cctccaattg aactttaaac cataattaaa ttcattttat cctgatattg
5821 ttaaataaat cctaaagaga atcaattgag ttcattatac tagtatcata ttcgcgcttt
5881 caattttaaa ataatgcctt tgttaaactt ggctgttgat ttccgctcca ggtgagtgcg
5941 gttcgcgggc ggtccgggga gcctcctcgg cgctaagcgc ctgtggggtg tcccctgccc
6001 cgtcctcccg caggacattg agtaagctt

*Staphylococcus* β-glucuronidase

```
  1  MLYPINTETR GVFDLNGVWN FKLDYGKGLE EKWYESKLTD TISMAVPSSY
 51  NDIGVTKEIR NHIGYVWYER EFTVPAYLKD QRIVLRFGSA THKAIVYVNG
101  ELVVEHKGGF LPFEAEINNS LRDGMNRVTV AVDNILDDST LPVGLYSERH
151  EEGLGKVIRN KPNFDFFNYA GLHRPVKIYT TPFTYVEDIS VVTDFNGPTG
201  TVTYTVDFQG KAETVKVSVV DEEGKVVAST EGLSGNVEIP NVILWEPLNT
251  YLYQIKVELV NDGLTIDVYE EPFGVRTVEV NDGKFLINNK PFYFKGFGKH
301  EDTPINGRGF NEASNVMDFN ILKWIGANSF RTAHYPYSEE LMRLADREGL
351  VVIDETPAVG VHLNFMATTG LGEGSERVST WEKIRTFEHH QDVLRELVSR
401  DKNHPSVVMW SIANEAATEE EGAYEYFKPL VELTKELDPQ KRPVTIVLFV
451  MATPETDKVA ELIDVIALNR YNGWYFDGGD LEAAKVHLRQ EFHAWNKRCP
501  GKPIMITEYG ADTVAGFHDI DPVMFTEEYQ VEYYQANHVV FDEFENFVGE
551  QAWNFADFAT SQGVMRVQGN KKGVFTRDRK PKLAAHVFRE RWTNIPDFGY
601  KN
```

*B*

*Enterobacter/Salmonella* ß-glucuronidase

```
  1  GKLSPTPTAY IQDVTVXTDV LENTEQATVL GNVGADGDIR VELRDGQQQI
 51  VAQGLGATGI FELDNPHLWE PGEGYLYELR VTCEANGECD EYPVRVGIRS
101  ITXKGEQFLI NHKPFYLTGF GRHEDADFRG KGFDPVLMVH DHALMNWIGA
151  NSYRTSHYPY AEKMLDWADE HVIVVINETA AGGFNTLSLG ITFDAGERPK
201  ELYSEEAING ETSQQAHLQA IKELIARDKN HPSVVCWSIA NEPDTRPNGA
251  REYFAPLAKA TRELDPTRPI TCVNVMFCDA ESDTITDLFD VVCLNRYYGW
301  YVQSGDLEKA EQMLEQELLA WQSKLHRPII ITEYGVDTLA GMPSVYPDMW
351  SEKYQWKWLE MYHRVFDRGS VC
```

*C*

*Staphylococcus homini* ß-D-glucuronidase

```
  1  GLSGNVEIPN VILWEPLNTY LYQIKVELVN DGLTIDVYEE PFGVRTVEVN
 51  DGKFLINNKP FYFKGFGKHE DTPINGRGFN EASNVMDFNI LKWIGANSFR
101  TAHYPYSEEL MRLADREGLV VIDETPAVGV HLNFMATTGL GEGSERVSTW
151  EKIRTFEHHQ DVLRELVSRD KNHPSVVMWS IANEAATEEE GAYEYFKPLG
201  GAAKELDPXK RPVTIVLFVM ATPETDKVAE LIDVIALNRY NGWYFDGGDL
251  EAAKVHLRQE FHAWNKRCPG KPIMITEYGA DTVAGFHDID PVMFTEEYQV
301  EYYQANHVVF DEFENFVGEQ AWNFADFATS QGVMRVQGNK KGVFTRDRKP
351  XLAAHVFRER RTNIPDFGYK NASHHH
```

*Staphylococcus warneri* ß-D-glucuronidase

```
  1  LXLLHPITTG TRGGFALYGX XNLMLDYGXG LTDTWTXSLL TELSRLVVLS
 51  WTTHXLTGEX PAISILWPNS ELTVSXLYXG SLXSSSXLCS SLTXHVVICQ
101  XVTLXVDHTG LIXXFEFMST TCCXXDELVT GTLAXILYHX ILPHGLYRKR
151  HEXGLGKXNF YXLHFAFFXY AXLXRTVXMY XNLVRXQDIX VVTXXHXXXX
201  TVEQCVXXNX KIXSVKITIL DENDHAIXES EGAKGNVTIQ NPILWQPLHA
251  YLYNMKVELL NDNECVDVYT ERFGIRSVEV KDGQFLINDK PFYFKGFGKH
301  EDTYXNGRGL NESANVMDIN LMKWIGANSF RTSHYPYSEE MMRLADEQGI
351  VVIDETTXVG IHLNFMXTLG GSXAHDTWXE FDTLEFHKEV IXDLIXRDKN
401  HAWVVMWXFG NEXGXNKGGA KAXFEPFVNL AGEKDXXXXP VTIVTILXAX
451  RNVCEVXDLV DVVCLXXXXG WYXQSGDLEG AKXALDKEXX EWWKXQXNKP
501  XMFTEYGVDX VVGLXXXPDK MXPEEYKMXF YKGYXKIMDK
```

*E*

*Thermotoga maritima* ß-glucuronidase

```
  1  MVRPQRNKKR FILILNGVWN LEVTSKDRPI AVPGSWNEQY QDLCYEEGPF
 51  TYKTTFYVPK XLSQKHIRLY FAAVNTDCEV FLNGEKVGEN HIEYLPFEVD
101  VTGKVKSGEN ELRVVVENRL KVGGFPSKVP DSGTHTVGFF GSFPPANFDF
151  FPYGGIIRPV LIEFTDHARI LDIWVDTSES EPEKKLGKVK VKIEVSEEAV
201  GQEMTIKLGE EEKKIRTSNR FVEGEFILEN ARFWSLEDPY LYPLKVELEK
251  DEYTLDIGIR TISWDEKRLY LNGKPVFLKG FGKHEEFPVL GQGTFYPLMI
301  KDFNLLKWIN ANSFRTSHYP YSEEWLDLAD RLGILVIDEA PHVGITRYHY
351  NPETQKIAED NIRRMIDRHK NHPSVIMWSV ANEPESNHPD AEGFFKALYE
401  TANEMDRTRP VVMVSMMDAP DERTRDVALK YFDIVCVNRY YGWYIYQGRI
451  EEGLQALEKD IEELYARHRK PIFVTEFGAD AIAGIHYDPP QMFSEEYQAE
501  LVEKTIRLLL KKDYIIGTHV WAFADFKTPQ NVRRPILNHK GVFTRDRQPK
551  LVAHVLRRLW SEV
```

FIG. 4A

*Staphylococcus* β-glucuronidase

```
    MetLeuTyrProIleAsnThrGluThrArgGlyValPheAspLeuAsnGl
1   ATGTTATATCCAATCAATACAGAAACCCGAGGAGTTTTTGATTTAAATGG

    yValTrpAsnPheLysLeuAspTyrGlyLysGlyLeuGluGluLysTrpT
51  GGTCTGGAATTTTAAATTAGATTACGGCAAAGGACTGGAAGAAAAGTGGT

    yrGluSerLysLeuThrAspThrIleSerMetAlaValProSerSerTyr
101 ATGAATCAAAACTGACAGATACCATATCAATGGCTGTACCTTCCTCCTAT

    AsnAspIleGlyValThrLysGluIleArgAsnHisIleGlyTyrValTr
151 AATGATATCGGTGTTACGAAGGAAATTCGAAACCATATCGGCTATGTATG

    pTyrGluArgGluPheThrValProAlaTyrLeuLysAspGlnArgIleV
201 GTACGAGCGTGAATTTACCGTTCCTGCTTATTTAAAAGATCAGCGCATCG

    alLeuArgPheGlySerAlaThrHisLysAlaIleValTyrValAsnGly
251 TCCTGCGTTTTGGTTCAGCAACACATAAGGCTATTGTATACGTTAACGGA

    GluLeuValValGluHisLysGlyGlyPheLeuProPheGluAlaGluIl
301 GAACTAGTAGTTGAACACAAAGGCGGCTTCTTACCGTTTGAGGCAGAAAT

    eAsnAsnSerLeuArgAspGlyMetAsnArgValThrValAlaValAspA
351 AAACAACAGCTTAAGAGACGGAATGAATCGTGTAACAGTAGCGGTTGATA

    snIleLeuAspAspSerThrLeuProValGlyLeuTyrSerGluArgHis
401 ATATTTTAGATGATTCTACGCTCCCAGTTGGGCTATATAGTGAAAGACAT

    GluGluGlyLeuGlyLysValIleArgAsnLysProAsnPheAspPhePh
451 GAAGAAGGTTTGGGAAAAGTGATTCGTAATAAACCTAATTTTGACTTCTT

    eAsnTyrAlaGlyLeuHisArgProValLysIleTyrThrThrProPheT
501 TAACTATGCAGGCTTACATCGTCCTGTAAAAATTTATACAACCCCTTTTA

    hrTyrValGluAspIleSerValValThrAspPheAsnGlyProThrGly
551 CCTATGTTGAGGATATATCGGTTGTAACCGATTTTAACGGTCCAACGGGA

    ThrValThrTyrThrValAspPheGlnGlyLysAlaGluThrValLysVa
601 ACAGTTACGTATACAGTTGATTTTCAGGGTAAGGCAGAAACCGTAAAGGT

    lSerValValAspGluGluGlyLysValValAlaSerThrGluGlyLeuS
651 TAGTGTAGTTGATGAAGAAGGGAAAGTTGTTGCTTCAACTGAAGGCCTCT
```

FIG. 4B

```
     erGlyAsnValGluIleProAsnValIleLeuTrpGluProLeuAsnThr
701  CTGGTAATGTTGAGATTCCTAACGTTATCCTTTGGGAACCTTTAAATACC

     TyrLeuTyrGlnIleLysValGluLeuValAsnAspGlyLeuThrIleAs
751  TATCTCTATCAAATTAAAGTTGAGTTAGTAAATGATGGTCTAACTATTGA

     pValTyrGluGluProPheGlyValArgThrValGluValAsnAspGlyL
801  TGTATACGAAGAGCCATTTGGAGTTCGAACCGTTGAAGTAAACGACGGGA

     ysPheLeuIleAsnAsnLysProPheTyrPheLysGlyPheGlyLysHis
851  AATTCCTCATTAATAACAAACCATTTTATTTTAAAGGGTTCGGAAAACAC

     GluAspThrProIleAsnGlyArgGlyPheAsnGluAlaSerAsnValMe
901  GAGGATACTCCAATAAATGGAAGAGGCTTTAATGAAGCATCAAATGTAAT

     tAspPheAsnIleLeuLysTrpIleGlyAlaAsnSerPheArgThrAlaH
951  GGATTTTAATATTTTGAAATGGATCGGTGCGAATTCCTTTCGGACGGCGC

     isTyrProTyrSerGluGluLeuMetArgLeuAlaAspArgGluGlyLeu
1001 ACTATCCTTATTCTGAAGAACTGATGCGGCTCGCAGATCGTGAAGGGTTA

     ValValIleAspGluThrProAlaValGlyValHisLeuAsnPheMetAl
1051 GTCGTCATAGATGAAACCCCAGCAGTTGGTGTTCATTTGAACTTTATGGC

     aThrThrGlyLeuGlyGluGlySerGluArgValSerThrTrpGluLysI
1101 AACGACTGGTTTGGGCGAAGGTTCAGAGAGAGTGAGTACTTGGGAAAAAA

     leArgThrPheGluHisHisGlnAspValLeuArgGluLeuValSerArg
1151 TCCGGACCTTTGAACATCATCAAGATGTACTGAGAGAGCTGGTTTCTCGT

     AspLysAsnHisProSerValValMetTrpSerIleAlaAsnGluAlaAl
1201 GATAAAAACCACCCCTCTGTTGTCATGTGGTCGATTGCAAATGAAGCGGC

     aThrGluGluGluGlyAlaTyrGluTyrPheLysProLeuValGluLeuT
1251 TACGGAAGAAGAAGGCGCTTATGAATACTTTAAGCCATTAGTTGAATTAA

     hrLysGluLeuAspProGlnLysArgProValThrIleValLeuPheVal
1301 CGAAAGAATTAGATCCACAAAAACGCCCAGTTACCATTGTTTTGTTCGTA

     MetAlaThrProGluThrAspLysValAlaGluLeuIleAspValIleAl
1351 ATGGCGACACCAGAAACAGATAAAGTGGCGGAGTTAATTGATGTGATTGC

     aLeuAsnArgTyrAsnGlyTrpTyrPheAspGlyGlyAspLeuGluAlaA
1401 ATTGAATCGATACAACGGCTGGTATTTTGATGGGGGTGATCTTGAAGCCG
```

FIG. 4C

```
      laLysValHisLeuArgGlnGluPheHisAlaTrpAsnLysArgCysPro
1451  CGAAAGTCCACCTTCGTCAGGAATTTCATGCGTGGAATAAACGCTGTCCA

      GlyLysProIleMetIleThrGluTyrGlyAlaAspThrValAlaGlyPh
1501  GGAAAACCTATAATGATAACAGAGTATGGGGCTGATACCGTAGCTGGTTT

      eHisAspIleAspProValMetPheThrGluGluTyrGlnValGluTyrT
1551  TCATGATATTGATCCGGTTATGTTTACAGAAGAGTATCAGGTTGAATATT

      yrGlnAlaAsnHisValValPheAspGluPheGluAsnPheValGlyGlu
1601  ACCAAGCAAATCATGTAGTATTTGATGAATTTGAGAACTTTGTTGGCGAG

      GlnAlaTrpAsnPheAlaAspPheAlaThrSerGlnGlyValMetArgVa
1651  CAGGCCTGGAATTTTGCAGACTTTGCTACAAGCCAGGGTGTCATGCGTGT

      lGlnGlyAsnLysLysGlyValPheThrArgAspArgLysProLysLeuA
1701  TCAAGGTAACAAAAAAGGTGTTTTCACACGCGACCGCAAACCAAAATTAG

      laAlaHisValPheArgGluArgTrpThrAsnIleProAspPheGlyTyr
1751  CAGCACATGTTTTCCGCGAACGTTGGACAAACATCCCGGATTTCGGTTAT

      LysAsn
1801  AAAAAT
```

FIG. 4D

*Enterobacter/Salmonella* ß-glucuronidase gene

```
CATTGGGGAAACTTTCCCCCACACCTACTGCGTATATTCAGGATGTTACG    50
GTTNTTACTGATGTTTTGGAAAATACTGAACAGGCGACCGTAACTGGGGA   100
ATGTGGGGGCTGATGGTGATATTCGGGTTGAGCTTCGCGATGGGCAGCAA   150
CAAATAGTGGCACAAGGGCTGGGGGCCACAGGTATATTTGAACTGGATAA   200
TCCTCATCTTTGGGAACCAGGTGAAGGGTATTTGTACGAGCTGCGGGTTA   250
CCTGCGAAGCCAATGGTGAGTGTGACGAATATCCAGTACGTGTCGGTATC   300
CGTTCCATTACGGNTAAGGGTGAGCAGTTTTTGATTAACCACAAACCGTT   350
TTATTTAACCCGGTTTTGGTCGACATGAAGATGCAGATTTTCGCGGCAAA   400
GGTTTCGACCCGGGTGTTGATGGTTCACGACCACGCGTTGATGAACTGGA   450
TTGGGCTAACTCCTATCGCACGTCCCACTACCCTTACGCGGAAAAGATGC   500
TCGATTGGGCTGATGAGCACGTATCGTAGTGATTAATGAAACCGCGGCGG   550
GTGGCTTTAACACTTTATCGTTGGGAATCACTTTTGACGCAGGCGAAAGA   600
CCTAAAGAACTTCTACAGCGAAGAGGCGATTAATGGCGAGACTTCAGCAG   650
GCTCACTTGCAGGCTATAAAAGAGCTTATTGCCCGGGATAAAAACCATCC   700
AAGTGTAGTGTGTGGAGTATTGCCAATGAGCCCGACACCCGTCCAAATGG   750
AGCCAGAGAGTACTTTGCGCCTTTAGCTAAGGCCACTCGTGAACTGGATC   800
CGACACGTCCGATTACCTGCGTAAACGTGATGTTCTGCGATGCCGAAAGC   850
GACACCATCACCGACCTGTTCGACGTGGTTTGTCTGAATCGCTATTACGG   900
CTGGTATGTGCAATCAGGTGATTTGGAAAAAGCAGAACAGATGCTGGAGC   950
AAGAACTGCTGGCCTGGCAGTCAAAACTACATCGCCCAATTATTATTACG  1000
GAATACGGTGTCGATACGCTGGCAGGAATGCCCTCGGTTTATCCCGACAT  1050
GTGGAGTGAAAAGTACCAGTGAAATGGCTTGAAATGTATCACCGTGTCTT  1100
TGACCGGGGGAGCGTTTGCAAGCGCNAAGCTTAGTTAACACCGGNGGTAC  1150
CGATCACGCGTNAGGCGCCNCCCATGGNCATATGNGCTAGCNTGCGGCCG  1200
```

FIG. 4E

CNATGCATTCTGCAGCGATCGCAGCTGAGTACACGAGCTCACCCGCGGAG 1250

TCGACAAGATCCAAGTACTACCCGGGNATACGTAACTAGTGCATGCTCGC 1300

GAAATATTTAGGCCTTATCGAATTAAT 1328

Pseudomonas ß-D-glucuronidase

CTTGCTGGACNACNGTTNAGGATTTTTAGACACGNGGAGCTAAAGCTTGC 50

TGACCNAACTATCACGCCGGNCGTGCANGCTTGGACCGCGACATTNCCTG 100

ACANGNGAAANACTCCGCCATATCCATCTTTGCTGGCCCAACAGTGAGTT 150

NACNGTNNCGNACNNTNNGANGGATCAGTGNATCGAGCTCCNTTNANNTT 200

CTNCGCTAACATAACATGTNGCATATGTCAATNAATNACGCTGGNCGTGG 250

ANCNCACCGGGCTNATTCGNTGNNATTCGAATTGNATGNCAACAACTNTG 300

NTGCACGNTGGNAAANAATTGCGTNACAGGGACTTTGGCCNCTTCCTAAA 350

CCATNGCATCCTCCCNATGGGCTGTACACGAATGNGCCCCCAAAANGGCN 400

TTCAGAAAGGCAATTTNTAACAAGGCNGANNTTTGACTTTTTCAACTATG 450

CAGNNCTGCACCGGACGCTGAAAATGTACANGACCCTGGGTACGTNCNAC 500

CAAGACATNNAAGTNGTGACCGACTCCATTGTNCTAACCGGGACTGTACC 550

TATAATGCGGACTATCANGGCAATGCATGACGTNGAANCGACACACCAGG 600

ATNAGGAAAACAANTGGTGGNANCNCACCANGCCATGATTGTCACGTTTT 650

GTTAGCNTNGANACNAATTCNATTGCTTTNTTAGCTTNTTANATNAGCCT 700

NTTTANATTAGANTTCTNANTGAGACTGT 730

Salmonella ß-glucuronidase

NCTCATGACCCNCCCNTTTTNGTANCNTNTTTGNNANCTGCTGCANNNGA 50

TCACNACNNGGANNCGGGGNGGGTTCGNNCTCTATGGCNCGNGGAACNNN 100

ATGNTGGNCNACNGTTNANGACTGACAGACACGTGGAGCTAAAGCTTGCT 150

FIG. 4F

GCCGAACTATCACTCAGNTCNTGNAAGTTGGACAACACATTNCCTGACAN 200

GNGAAAAGCCCGCCATATCCATACTGTGCTGGCCCAACANTGAGTTCACN 250

GTCGTCGNACTNTATGANGGATCACCTGTATCGANCTCCNTTNATNTTCT 300

NCAGCTAACATAACTGTGNGCATATGTCAATGNATGACCTGGTCGGTGNA 350

NCACACCGGGCGTNATTGNTGNNATTCGAATTTNATGTCAACAACTTTGN 400

TGCANGNTGGAATGAATCTGGGGGCCAGGGACTTTGGCCANCTTCCTNAA 450

CCATTCGCANCCTCCCCCAGTGGGCTTGTACACNATTGNGCCCCAAAAAG 500

GCNTCAGATAGGCATTTTGACAAGCTCCANNTTAACTTTTTCAACTATGC 550

NGNCCTGCACCGGACGCTGAAAAANGTACANGANCCTTGTACGTTCCACC 600

AAGANATTTAAGGTGTGACCCACNTCCATTTTCCTAACNGGACTGTGACT 650

NATAAAGGNTGACCNTTCANGGACACATTGCAATGACCCTTTNAAACGGA 700

ANAACCCCCGGNTTAAAGGAAAAACAAATTTGGTTGGGNAGTCCANCCAA 750

GGGCCAATTANTTGTTNCNCGGGGGANTAAANCCCCCNCCAATCGATCTT 800

CGAAATTTAAACAGCGCTCCGGCCGCCACGTGCGAATTCCGATATCGGAT 850

GAGGCCAGCGCNAAGCTTAGTTAACACCGGNGGTACCGATCACGCGTNAG 900

GCGCCNCCCATGGNCATATGNGCTAGCNTGCGGCCGCNATGCATTCTGCA 950

GCGATCGCAGCTGAGTACACGAGCTCACCCGCGGAGTCGACAAGATCCAA 1000

GTACTACCCGGGNATACGTAACTAGTGCATGCTCGCGAAATATTTAGGCC 1050

TTATCGAATTAA 1063

Staphylococcus warneri ß-glucuronidase

TANANCTTGTNTCTGCTGCACCCNATCACGACAGGGACCCGGGGNGGGTT 50

CGCGCTCTATGGCNCGNGGAACTTAATGCTGGACTACGGTTNAGGACTGA 100

CAGACACGTGGACTNAAAGCTTGCTGACCGAACTATCACGACTGGTCGTG 150

CTAAGTTGGACCACACATTNCCTGACAGGGGAAANACCCGCCATATCCAT 200

FIG. 4G

CTTGTGGCCCAACAGTGAGTTAACCGTGTCGANCTTATATGANGGATCAC 250

TGNATTCGAGCTCCNTCTTATGTTCTTCGCTAACATANCATGTNGTCATA 300

TGTCAATANGTGACNCTGGNCGTGGATCACACCGGGCTNATTGNTGNATT 350

CGAATTTATGTCAACAACTTGTTGCANGNTGGATGAATTGGTNACAGGGA 400

CTTTGGCCANCATCCTATACCATNGCATCCTTCCCCATGGGCTTTACCGA 450

AAGCGCCACGAAAANGGCCTCGGAAAAGNCAATTTTTACNGGCTCCACTT 500

TGCNTTTTTCAANTATGCNGANCTGNACCGGACGGTNANAATGTACANGA 550

ACCTTGTACGTCNNCAAGACATTTAGGTTGTGACCGNTTAGCATNAGCNG 600

TNNTAAACAGTAGAACAATGTGTGANCCNTAACTAAAAAATANACAGCGT 650

TAAAATCACGATTCTGGATGAAAATGATCATGCAATANCCGAAAGCGAAG 700

GCGCTAAAGGCAATGTAACTATTCAAAATCCTATATTGTGGCAACCTTTA 750

CATGCCTATTTATACAATATGAAAGTAGAATTACTCAACGATAATGAGTG 800

TGTAGATGTTTATACAGAACGTTTCGGTATTCGATCTGTNGAAGTGAAGG 850

ATGGACAGTTTTTAATTAATGACAAACCATTTTATTTCAAAGGTTTCGGT 900

AAACATGAAGATACCTATTAAAATGGTCGAGGCTTAAACGAATCAGCCAA 950

CGTCATGGACATCAACTTAATGAAATGGATAGGTGCTAATTCATTTAGAA 1000

CCTCTCATTACCCATATTCAGAAGAAATGATGCGTTTAGCAGATGAACAA 1050

GGTATTGTAGTGATAGATGAGACAACANGTGTCGGTATACATCTTAATTT 1100

TATGGNNACCTTAGGTGGCTCCNTTGCACATGATACATGGAANGAATTTG 1150

ACACTCTCGAGTTTCATAAAGAAGTCATANAAGACTTGATTGNGAGAGAC 1200

AAGAATCATGCATGGGTAGTCATGTGGTNATTTGGCAATGAGCNAGGGTN 1250

AAATAAAGGGGGTGCTAAAGCATNCTTTGAGCCATTTGTTAATTTAGCAG 1300

GTGAAAAAGATNNTCNGNNTNGCCCAGTGACTATCGTTACTATATTANCT 1350

GCNNANCGAAATGTATGTGAAGTTNNAGATTTAGTCGATGTGGTTTGTCT 1400

FIG. 4H

NNNNAGNNNNTANGGTTGGTATNCACAATCAGGTGATTTAGAAGGTGCTA 1450

AACNAGCATTAGATAAGGAGNTAGNCGAATGGTGGAAANGACAACNAAAT 1500

AAGCCAATNATGTTTACAGAGTATGGTGTGGATANNGTTGTAGGTTTACA 1550

NNCGATNCCTGATAAAATGCNNCCAGAAGAGTATAAAATGAGNTTTTATA 1600

AAGGNTATNATAAAATTATGGATAAACGATCGCAGCTGAGTACACGAGCT 1650

CACCCGCGGAGTCGACAAGATCCAAGTACTACCCGGGNATACGTAACTAG 1700

TGCATGCTCGCGAAATATTTAGGCCTTATCGAATTAAT 1739

*Staphylococcus homini* ß-glucuronidase gene

TGTGGGNCTTTGTTCCTTGNTCAGCTCCCCAACGGCTTGAAGTACTCGTA 50

CGCGCCCTCTTCCTCAGTCGCCGCCTCGTTGGCGATGCTCCACATCACGA 100

CGCTTGGATGGTTCTTGTCACGAGACACCAGTTCACGGAGAACGTCTTGA 150

TGGTGCTCAAACGTCCGAATCTTCTCCCAGGTACTGACGCGCTCGCTGCC 200

TTCGCCGAGTCCCGTGGTGGCCATGAAGTTGAGGTGCACGCCAACTGCCG 250

GAGTCTCGTCGATCACGACCAGACCCTCGCGATCCGCAAGACGCATCAAC 300

TCTTCAGAGTACGGATAGTGTGCGGTCCGGAAGCTGTTGGCGCCGATCCA 350

TTTGAGGATATTGAAATCCATCACATTGCTCGCTTCGTTAAAGCCACGGC 400

CGTTGATAGGAGTGTCCTCATGTTTGCCAAAGCCCTTGAAGTAGAACGGT 450

TTGTTGTTGATGAGGAACTTGCCGTCGTTGACTTCACGGTCCGCACGCCG 500

AACGGCTCTTCATAGACATCGATGGTCAAGTCCCGTCGTTCACCAGTTCC 550

ACTTTGATCTGGTAGAGATACGTGTTCAAGTGGTTCCCAGAGGATGACAT 600

TCGGAATCTTCACGTTACCGCTCAAGCC 629

FIG. 4I

Thermotoga maritima ß-glucuronidase

```
ATGGTAAGACCGCAACGAAACAAGAAGAGATTTATTCTTATCTTGAATGG    50
AGTTTGGAATCTTGAAGTAACCAGCAAAGACAGACCAATCGCCGTTCCTG   100
GAAGCTGGAATGAGCAGTACCAGGATCTGTGCTACGAAGAAGGACCCTTC   150
ACCTACAAAACCACCTTCTACGTTCCGAAGNAACTTTCACAAAAACACAT   200
CAGACTTTACTTTGCTGCGGTGAACACGGACTGCGAGGTCTTCCTCAACG   250
GAGAGAAAGTGGGAGAGAATCACATTGAATACCTTCCCTTCGAAGTAGAT   300
GTGACGGGGAAAGTGAAATCCGGAGAGAACGAACTCAGGGTGGTTGTTGA   350
GAACAGATTGAAAGTGGGAGGATTTCCCTCGAAGGTTCCAGACAGCGGCA   400
CTCACACCGTGGGATTTTTTGGAAGTTTTCCACCTGCAAACTTCGACTTC   450
TTCCCCTACGGTGGAATCATAAGGCCTGTTCTGATAGAGTTCACAGACCA   500
CGCGAGGATACTCGACATCTGGGTGGACACGAGTGAGTCTGAACCGGAGA   550
AGAAACTTGGAAAAGTGAAAGTGAAGATAGAAGTCTCAGAAGAAGCGGTG   600
GGACAGGAGATGACGATCAAACTTGGAGAGGAAGAGAAAAAGATTAGAAC   650
ATCCAACAGATTCGTCGAAGGGGAGTTCATCCTCGAAAACGCCAGGTTCT   700
GGAGCCTCGAAGATCCATATCTTTATCCTCTCAAGGTGGAACTTGAAAAA   750
GACGAGTACACTCTGGACATCGGAATCAGAACGATCAGCTGGGACGAGAA   800
GAGGCTCTATCTGAACGGGAAACCTGTCTTTTTGAAGGGCTTTGGAAAGC   850
ACGAGGAATTCCCCGTTCTGGGGCAGGGCACCTTTTATCCATTGATGATA   900
AAAGACTTCAACCTTCTGAAGTGGATCAACGCGAATTCTTTCAGGACCTC   950
TCACTATCCTTACAGTGAAGAGTGGCTGGATCTTGCCGACAGACTCGGAA  1000
TCCTTGTGATAGACGAAGCCCCGCACGTTGGTATCACAAGGTACCACTAC  1050
AATCCCGAGACTCAGAAGATAGCAGAAGACAACATAAGAAGAATGATCGA  1100
CAGACACAAGAACCATCCCAGTGTGATCATGTGGAGTGTGGCGAACGAAC  1150
CAGAGTCCAACCATCCAGACGCGGAGGGTTTCTTCAAAGCCCTTTATGAG  1200
```

FIG. 4J

ACTGCCAATGAAATGGATCGAACACGCCCCGTTGTCATGGTGAGCATGAT 1250

GGACGCACCAGACGAGAGAACAAGAGACGTGGCGCTGAAGTACTTCGACA 1300

TCGTCTGTGTGAACAGGTACTACGGCTGGTACATCTATCAGGGAAGGATA 1350

GAAGAAGGACTTCAAGCTCTGGAAAAAGACATAGAAGAGCTCTATGCAAG 1400

GCACAGAAAGCCCATCTTTGTCACAGAATTCGGTGCGGACGCGATAGCTG 1450

GCATCCACTACGATCCACCTCAAATGTTCTCCGAAGAGTACCAAGCAGAG 1500

CTCGTTGAAAAGACGATCAGGCTCCTTTTGAAAAAAGACTACATCATCGG 1550

AACACACGTGTGGGCCTTTGCAGATTTTAAGACTCCTCAGAATGTGAGAA 1600

GACCCATTCTCAACCACAAGGGTGTTTTCACAAGAGACAGACAACCCAAA 1650

CTCGTTGCTCATGTACTGAGAAGACTGTGGAGTGAGGTT 1689

FIG. 5A

```
BGUS    ------MLYPINTETRGVFDLNGVWNFKLDYG----KGLEEKWYESKLTDT---ISMAVP 47
HGUS    LGLQGGMLYPQESPSRECKELDGLWSFRADFSDNRRRGFEEQWYRRPLWESGPTVDMPVP 60
EGUS    ------MLRPVETPTREIKKLDGLWAFSLDREN---CGIDQRWWESALQESR---AIAVP 48

BGUS    SSYNDIGVTKEIRNHIGYVWYEREFTVPAYLKD---QRIVLRFGSATHKAIVYVNGELVV 104
HGUS    SSFNDISQDWRLRHFVGWVWYEREVILPERWTQDLRTRVVLRIGSAHSYAIVWVNGVDTL 120
EGUS    GSFNDQFADADIRNYAGNVWYQREVFIPKGWAG---QRIVLRFDAVTHYGKVWVNNQEVM 105

BGUS    EHKGGFLPFEAEINNSLRDG----MNRVTVAVDNILDDSTLPVG-LYSERHEEGLGKVIR 159
HGUS    EHEGGYLPFEADISNLVQVGPLPSRLRITIAINNTLTPTTLPPGTIQYLTDTSKYPKGYF 180
EGUS    EHQGGYTPFEADVTPYVIAG---KSVRITVCVNNELNWQTIPPG--MVITDENGKKK--- 157

BGUS    -NKPNFDFFNYAGLHRPVKIYTTPFTYVEDISVVTDFNGPT--GTVTYTVDFQG-KAETV 215
HGUS    VQNTYFDFFNYAGLQRSVLLYTTPTTYIDDITVTTSVEQDS--GLVNYQISVKGSNLFKL 238
EGUS    -QSYFHDFFNYAGIHRSVMLYTTPNTWVDDITVVTHVAQDCNHASVDWQVVANG----DV 212

BGUS    KVSVVDEEGKVVASTEGLSGNVEIPNVILWEP-----LNTYLYQIKVELVNDGLT---ID 267
HGUS    EVRLLDAENKVVANGTGTQGQLKVPGVSLWWPYLMHERPAYLYSLEVQLTAQTSLGPVSD 298
EGUS    SVELRDADQQVVATGQGTSGTLQVVNPHLWQP-----GEGYLYELCVTAKSQTEC----D 263

BGUS    VYEEPFGVRTVEVNDGKFLINNKPFYFKGFGKHEDTPINGRGFNEASNVMDFNILKWIGA 327
HGUS    FYTLPVGIRTVAVTKSQFLINGKPFYFHGVNKHEDADIRGKGFDWPLLVKDFNLLRWLGA 358
EGUS    IYPLRVGIRSVAVKGEQFLINHKPFYFTGFGRHEDADLRGKGFDNVLMVHDHALMDWIGA 323

BGUS    NSFRTAHYPYSEELMRLADREGLVVIDETPAVGVHLNFMATTGLGEGSERVSTWEKIR-- 385
HGUS    NAFRTSHYPYAEEVMQMCDRYGIVVIDECPGVGLAL-----------P------QFFNNV 401
EGUS    NSYRTSHYPYAEEMLDWADEHGIVVIDETAAVGFNLSLGIGFEAGNKPKELYSEEAVNGE 383

BGUS    TFEHHQDVLRELVSRDKNHPSVVMWSIANEAATEEEGAYEYFKPLVELTKELDPQKRPVT 445
HGUS    SLHHHMQVMEEVVRRDKNHPAVVMWSVANEPASHLESAGYYLKMVIAHTKSLDPS-RPVT 460
EGUS    TQQAHLQAIKELIARDKNHPSVVMWSIANEPDTRPQGAREYFAPLAEATRKLDPT-RPIT 442

BGUS    IVLFVMATPETDKVAELIDVIALNRYNGWYFDGGDLEAAKVHLRQEFHAWNKRCPGKPIM 505
HGUS    FVS--NSNYAADKGAPYVDVICLNSYYSWYHDYGHLELIQLQLATQFENWYKKYQ-KPII 517
EGUS    CVNVMFCDAHTDTISDLFDVLCLNRYYGWYVQSGDLETAEKVLEKELLAWQEKLH-QPII 501

BGUS    ITEYGADTVAGFHDIDPVMFTEEYQVEYYQANHVVFD--EFENFVGEQAWNFADFATSQG 563
HGUS    QSEYGAETIAGFHQDPPLMFTEEYQKSLLEQYHLGLDQKRRKYVVGELIWNFADFMTEQS 577
EGUS    ITEYGVDTLAGLHSMYTDMWSEEYQCAWLDMYHRVFD--RVSAVVGEQVWNFADFATSQG 559

BGUS    VMRVQGNKKGVFTRDRKPKLAAHVFRERWTNIPDFGYKN----- 602
HGUS    PTRVLGNKKGIFTRQRQPKSAAFLLRERYWKIAN-ET------- 613
EGUS    ILRVGGNKKGIFTRDRKPKSAAFLLQKRWTGMNFGEKPQQGGKQ 603
```

FIG. 5B-1

```
Bacillus  : MVDLTSLYPINTETRGVFDLNGVWNFKLDYG-KGLEEKWYESKLTDTISMAVPSSY :  55
Staph_homi: -------------------------------------------------------- :   -
Staph_warn: ---LXLLHPITTGTRGGFALYGXXNLMLDYG-XGLTDTWTXSLLTELSRLVVLSWT :  52
Thermotoga: -----MVRPQRNKKRFILILNGVWNLEVTSK--------------D-RPIAVPGSW :  36
Enb/Salmon: -------------------------------------------------------- :   -
E_coli    : -----MLRPVETPTREIKKLDGLWAFSLDRENCGIDQRWWESALQESRAIAVPGSF :  51

Bacillus  : NDIGVTKEIRNHIGYVWYEREFTVPAYLKDQR--IVLRFGSATHKAIVYVNGELVV : 109
Staph_homi: -------------------------------------------------------- :   -
Staph_warn: THX-LTGEX-PAISILWPNSELTVSXLYXGSLXSSSXLCSSLTXHVVICQXVTLXV : 106
Thermotoga: NEQ--YQDLCYEEGPFTYKTTFYVPKXLSQKH--IRLYFAAVNTDCEVFLNGEKVG :  88
Enb/Salmon: -------------------------------------------------------- :   -
E_coli    : NDQFADADIRNYAGNVWYQREVFIPKGWAGQR--IVLRFDAVTHYGKVWVNNQEVM : 105

Bacillus  : EHKGGFLPFEAEIN-NSLRDGMNRVTVAVDNILDDSTLPVGLYSERHEEGLGKVIR : 164
Staph_homi: -------------------------------------------------------- :   -
Staph_warn: DHTGLIXXFEFMSTTCCXXDELVTGTLAX--ILYHXILPHGLYRKRHEXGLGKXNF : 160
Thermotoga: ENHIEYLPFEVDVTGKVKSGENELRVVVEN-RLKVGGFPSKVPDSGTHTVGFFGSF : 143
Enb/Salmon: -------------------------------------------------------- :   -
E_coli    : EHQGGYTPFEADVTPYVIAGKSVRITVCVNNELNWQTIPPGMVITDENG----KKK : 157

Bacillus  : NKPNFDFFNYAGLHRPVKIYTTPFTYVEDISVVTDFNGP---TGTVTYTVDFQGKA : 217
Staph_homi: -------------------------------------------------------- :   -
Staph_warn: YXLHFAFFXYAXLXRTVXMYX-NLVRXQDI-VVTX-HX-----XX-TVEQCVXXN- : 206
Thermotoga: PPANFDFFPYGGIIRPVLIEFTDHARILDIWVDTSESEPEKKLGKVKVKIEVSEEA : 199
Enb/Salmon: ----------------GKLSPTPTAYIQDVTVXTDVLEN---TEQATVLGNVGADG :  37
E_coli    : QSYFHDFFNYAGIHRSVMLYTTPNTWVDDITVVTHVAQD---CNHASVDWQVVANG : 210
```

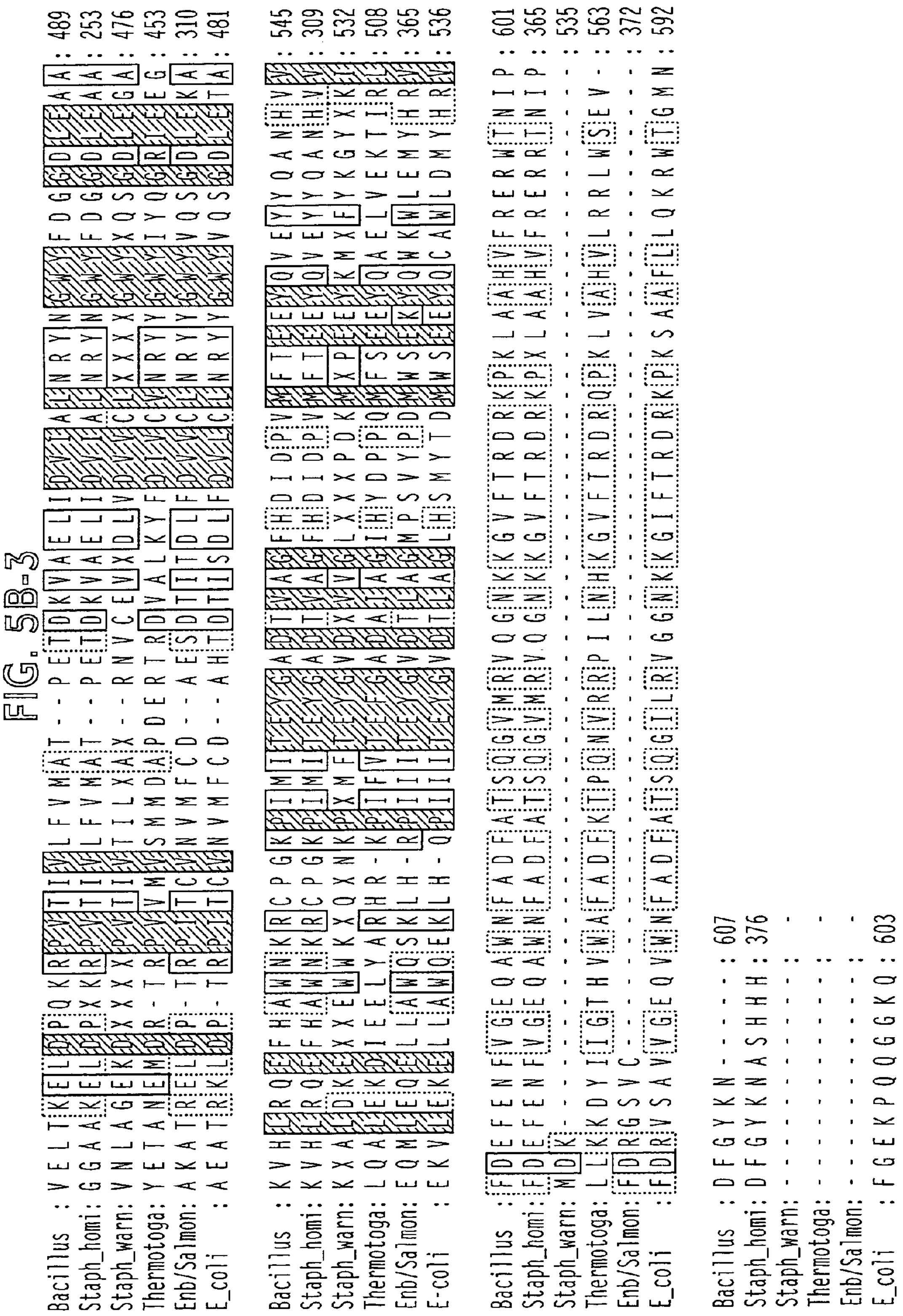

FIG. 5B-3

```
Bacillus  : V E L T K E L T P Q K R T I I - - - - - - L F V M A T - - P E T D K V A E L I A N R Y N G A F D G G D L E A A : 489
Staph_homi: G G A A K E L P X X X K K R T I I - - - - - - L F V M A T - - P E T D K V A E L I A N R Y N G A F D G G D L E A A : 253
Staph_warn: V N L A G E K D X X X X X X X I I I - - - - - - L X A X - - R N V C E V X D L V X X X X C G A I Y Q S G D L E G A : 476
Thermotoga: Y E T A N E M R - - - T R V M S M M D A P D E R T R D V A L K Y F D X G F I Y Q S G A L E E G : 453
Enb/Salmon: A K A T R E L D P - - T R T C C N V M F C D - - A E S D T I T D L F G V G R I E K A : 310
E-coli    : A E A T R K L D P - - T R T C C A H T D T I S D L F G V Q S G D L E T A : 481

Bacillus  : K V H H R Q F F H A W N K R C P G K I M I - - - F H D I D P V A G A N R Y F T E E Q V E Y Y Y Q A N H V : 545
Staph_homi: K V H H R Q F F H A W N K R C P G K K N K - - - F H D I D P V A G A N R Y F T E E Q V E Y Y Y Q A N H V : 309
Staph_warn: K X A D K E X X E W X X X Q X N K X P - K X X M F - - - L X X X P O K X X X A T A X X P F X K M X F Y X K : 532
Thermotoga: L Q A E E L Y A I E L Y X K - - K R L H - R - - I H Y D P P P I Q A E L V E K T I R : 508
Enb/Salmon: E Q M F E Q L L A W Q S K L H - - M P S V Y P D W W S K Q W K W L E M Y H R : 365
E-coli    : E K V L E J K L L A W Q E K L H - Q P I L H S M Y T D A W S E E Q C A W L D M Y H R : 536

Bacillus  : F D E F E N F V G E Q A W N F A D F A T S Q G V M R V Q G N K K G V F T R D R K P K L A A H V F R E R W T N I P : 601
Staph_homi: F D E F E N F V G E Q A W N F A D F A T S Q G V M R V Q G N K K G V F T R D R K P L A A H V F R E R R T N I P : 365
Staph_warn: M D K - - - - - - - - - - - K T P Q N V R R P I L N H K G V F T R D R Q P K L V A H V L R R L W S E V - : 535
Thermotoga: L L K K D Y I I G T H V W A F A D F K T P Q N V R R P I L N H K G V F T R D R Q P K L V A H V L R R L W S E V - : 563
Enb/Salmon: F D R G S V C - - - - - - - - - - - - - - - - - - - - - - - - - - - - - - - - - - - : 372
E-coli    : F D R V S A V G E Q V W N F A D F A T S Q G I I L R I V G G N K K G I F T R D R K P K S A A F L I L Q K R W T I G M N : 592

Bacillus  : D F G Y K N - - - - - : 607
Staph_homi: D F G Y K N A S H H H : 376
Staph_warn: - - - - - - - - - - - 
Thermotoga: - - - - - - - - - - - 
Enb/Salmon: - - - - - - - - - - - 
E-coli    : F G E K P Q Q G G K Q : 603
```

SECRETION OF GUS$^{Stp}$ IN E. coli

CELLULAR FRACTIONS WERE ASSAYED FOR GLUCURONIDASE AND GALACTOSIDASE ACTIVITY

SECRETION INDEX WAS CALCULATED AS FOLLOWS:

- PERCENT OF TOTAL ACTIVITY IN THE PERIPLASM FRACTION FOR GLUCURONIDASE AND GALACTOSIDASE WAS CALCULATED

- GALACTOSIDASE VALUE WAS SUBTRACTED FROM GLUCURONIDASE AS "CONTAMINATION"

THERMAL STABILITY OF β-GLUCURONIDASES

TURNOVER NUMBER (37°C)

TURNOVER NUMBER (RT)

EFFECT OF DETERGENTS ON GUS$^{Stp}$ ACTIVITY

EFFECT OF GLUCURONIC ACID, THE REACTION PRODUCT, ON GUS$^{Stp}$ ACTIVITY $GUS^{Stp}$ ACTIVITY IN SALT AND IN DIFFERENT ORGANIC SOLVENTS

FIG. 13A

```
                                MetValAspLeuThrSerLeuTyr
ATACGACTCA CTAGTGGGTC GACCCATGGTAGATCTGACTAGTCTGTAC
                  SalI    NcoI   BglII

ProIleAsnThrGluThrArgGlyValPheAspLeuAsnGlyValTrpAsn
CCGATCAACACCGAGACCCGTGGCGTCTTCGACCTCAATGGCGTCTGGAAC

PheLysLeuAspTyrGlyLysGlyLeuGluGluLysTrpTyrGluSerLys
TTCAAGCTGGACTACGGGAAAGGACTGGAAGAGAAGTGGTACGAAAGCAA

LeuThrAspThrIleSerMetAlaValProSerSerTyrAsnAspIle
GCTGACCGACACTATTAGTATGGCCGTCCCAAGCAGTTACAATGACATTG

GlyValThrLysGluIleArgAsnHisIleGlyTyrValTrpTyrGluArg
GCGTGACCAAGGAAATCCGCAACCATATCGGATATGTCTGGTACGAACGT

GluPheThrValProAlaTyrLeuLysAspGlnArgIleValLeuArgPhe
GAGTTCACGG TGCCGGCCTATCTGAAGGATCAGCGTATCGTGCTCCGCTT

GlySerAlaThrHisLysAlaIleValTyrValAsnGlyGluLeuVal
CGGCTCTGCAACTCACAAAGCAATTGTCTATGTCAATGGTGAGCTGGTCG

ValGluHisLysGlyGlyPheLeuProPheGluAlaGluIleAsnAsnSer
TGGAGCACAAGGGCGGATTCCTGCCATTCGAAGCGGAAATCAACAACTCG

LeuArgAspGlyMetAsnArgValThrValAlaValAspAsnIleLeuAsp
CTGCGTGATGGCATGAATCGCGTCACCGTCGCCGTGGACAACATCCTCGA

AspSerThrLeuProValGlyLeuTyrSerGluArgHisGluGluGly
CGATAGCACCCTCCCGGTGGGGCTGTACAGCGAGCGCCACGAAGAGGGCC

LeuGlyLysValIleArgAsnLysProAsnPheAspPhePheAsnTyrAla
TCGGAAAAGTCATTCGTAACAAGCCGAACTTCGACTTCTTCAACTATGCA

GlyLeuHisArgProValLysIleTyrThrThrProPheThrTyrValGlu
GGCCTGCACCGTCCGGTGAAAATCTACACGACCCCGTTTACGTACGTCGA

AspIleSerValValThrAspPheAsnGlyProThrGlyThrValThr
GGACATCTCGGTTGTGACCGACTTCAATGGCCCAACCGGGACTGTGACCT

TyrThrValAspPheGlnGlyLysAlaGluThrValLysValSerValVal
ATACGGTGGACTTTCAAGGCAAAGCCGAGACCGTGAAAGTGTCGGTCGTG

AspGluGluGlyLysValValAlaSerThrGluGlyLeuSerGlyAsnVal
GATGAGGAAGGCAAAGTGGTCGCAAGCACCGAGGGCCTGAGCGGTAACGT

GluIleProAsnValIleLeuTrpGluProLeuAsnThrTyrLeuTyr
GGAGATTCCGAATGTCATCCTCTGGGAACCACTGAACACGTATCTCTACC
```

FIG. 13B

GlnIleLysValGluLeuValAsnAspGlyLeuThrIleAspValTyrGlu
CAGATCAAAGTGGAACTGGTGAACGACGGACTGACCATCGATGTCTATGAA

GluProPheGlyValArgThrValGluValAsnAspGlyLysPheLeuIle
GAGCCGTTCGGCGTGCGGACCGTGGAAGTCAACGACGGCAAGTTCCTCAT

AsnAsnLysProPheTyrPheLysGlyPheGlyLysHisGluAspThr
CAACAACAAACCGTTCTACTTCAAGGGCTTTGGCAAACATGAGGACACTC

ProIleAsnGlyArgGlyPheAsnGluAlaSerAsnValMetAspPheAsn
CTATCAACGGCCGTGGCTTTAACGAAGCGAGCAATGTGATGGATTTCAAT

IleLeuLysTrpIleGlyAlaAsnSerPheArgThrAlaHisTyrProTyr
ATCCTCAAATGGATCGGCGCCAACAGCTTCCGGACCGCACACTATCCGTA

SerGluGluLeuMetArgLeuAlaAspArgGluGlyLeuValValIle
CTCTGAAGAGTTGATGCGTCTTGCGGATCGCGAGGGTCTGGTCGTGATCG

AspGluThrProAlaValGlyValHisLeuAsnPheMetAlaThrThrGly
ACGAGACTCCGGCAGTTGGCGTGCACCTCAACTTCATGGCCACCACGGGA

LeuGlyGluGlySerGluArgValSerThrTrpGluLysIleArgThrPhe
CTCGGCGAAGGCAGCGAGCGCGTCAGTACCTGGGAGAAGATTCGGACGTT

GluHisHisGlnAspValLeuArgGluLeuValSerArgAspLysAsn
TGAGCACCATCAAGACGTTCTCCGTGAACTGGTGTCTCGTGACAAGAACC

HisProSerValValMetTrpSerIleAlaAsnGluAlaAlaThrGluGlu
ATCCAAGCGTCGTGATGTGGAGCATCGCCAACGAGGCGGCGACTGAGGAA

GluGlyAlaTyrGluTyrPheLysProLeuValGluLeuThrLysGluLeu
GAGGGCGCGTACGAGTACTTCAAGCCGTTGGTGGAGCTGACCAAGGAACT

AspProGlnLysArgProValThrIleValLeuPheValMetAlaThr
CGACCCACAGAAGCGTCCGGTCACGATCGTGCTGTTTGTGATGGCTACCC

ProGluThrAspLysValAlaGluLeuIleAspValIleAlaLeuAsnArg
CGGAGACGGACAAAGTCGCCGAACTGATTGACGTCATCGCGCTCAATCGC

TyrAsnGlyTrpTyrPheAspGlyGlyAspLeuGluAlaAlaLysValHis
TATAACGGATGGTACTTCGATGGCGGTGATCTCGAAGCGGCCAAAGTCCA

LeuArgGlnGluPheHisAlaTrpAsnLysArgCysProGlyLysPro
TCTCCGCCAGGAATTTCACGCGTGGAACAAGCGTTGCCCAGGAAAGCCGA

IleMetIleThrGluTyrGlyAlaAspThrValAlaGlyPheHisAspIle
TCATGATCACTGAGTACGGCGCAGACACCGTTGCGGGCTTTCACGACATT

AspProValMetPheThrGluGluTyrGlnValGluTyrTyrGlnAlaAsn
GATCCAGTGATGTTCACCGAGGAATATCAAGTCGAGTACTACCAGGCGAA

FIG. 13C

```
  HisValValPheAspGluPheGluAsnPheValGlyGluGlnAlaTrp
 CCACGTCGTGTTCGATGAGTTTGAGAACTTCGTGGGTGAGCAAGCGTGGA

AsnPheAlaAspPheAlaThrSerGlnGlyValMetArgValGlnGlyAsn
 ACTTCGCGGACTTCGCGACCTCTCAGGGCGTGATGCGCGTCCAAGGAAAC

 LysLysGlyValPheThrArgAspArgLysProLysLeuAlaAlaHisVal
 AAGAAGGGCGTGTTCACTCGTGACCGCAAGCCGAAGCTCGCCGCGCACGT

  PheArgGluArgTrpThrAsnIleProAspPheGlyTyrLysAsn
 CTTTCGCGAGCGCTGGACCAACATTCCAGATTTCGGCTACAAGAACGCTA

SerHisHisHisHisHisHisVal *
 GCCATCACCATCACCATCACGTGTGAATTGGTGACCG
 NheI                PmlI       BstEII
```

FIG. 15
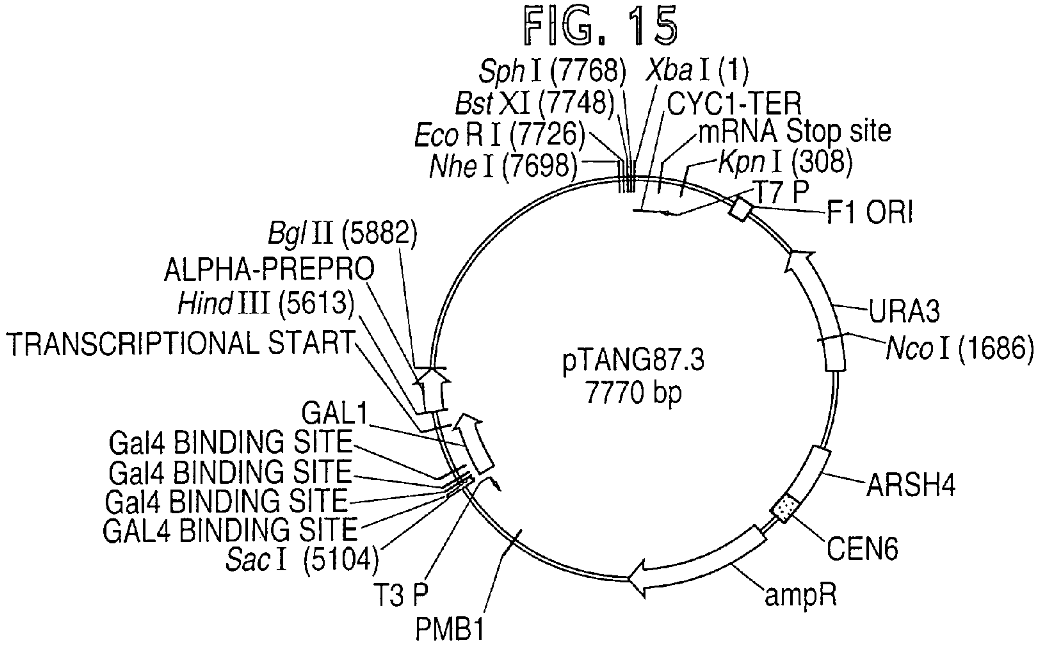
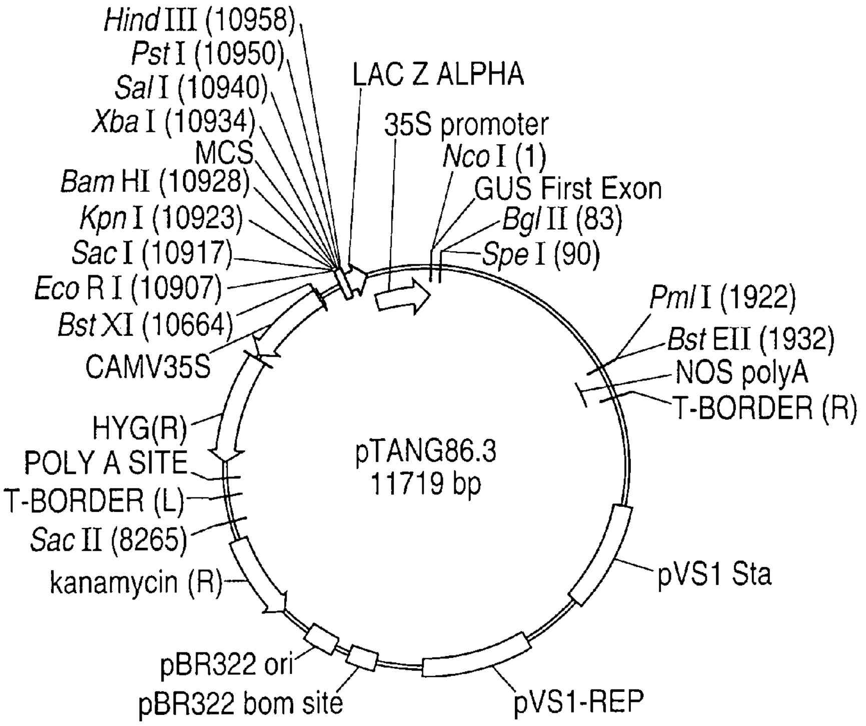

SEQUENCE LISTING

<160> NUMBER OF SEQ ID NOS: 112

<210> SEQ ID NO 1
<211> LENGTH: 2100
<212> TYPE: DNA
<213> ORGANISM: Bacillus sp.

<400> SEQUENCE: 1

```
agcctttact tttctttcaa cttttcatcc cgatactttt ttgtaatagt ttttttcatt      60

aataatacaa gtcctgattt tgcaagaata atccttttta gataaaaata tctatgctaa     120

taataacatg taaccactta catttaaaaa ggagtgctat catgttatat ccaatcaata     180

cagaaacccg aggagttttt gatttaaatg gggtctggaa ttttaaatta gattacggca     240

aaggactgga agaaaagtgg tatgaatcaa aactgacaga taccatatca atggctgtac     300

cttcctccta taatgatatc ggtgttacga aggaaattcg aaaccatatc ggctatgtat     360

ggtacgagcg tgaatttacc gttcctgctt atttaaaaga tcagcgcatc gtcctgcgtt     420

ttggttcagc aacacataag gctattgtat acgttaacgg agaactagta gttgaacaca     480

aaggcggctt cttaccgttt gaggcagaaa taaacaacag cttaagagac ggaatgaatc     540

gtgtaacagt agcggttgat aatattttag atgattctac gctcccagtt gggctatata     600

gtgaaagaca tgaagaaggt ttgggaaaag tgattcgtaa taaacctaat tttgacttct     660

ttaactatgc aggcttacat cgtcctgtaa aaatttatac aacccctttt acctatgttg     720

aggatatatc ggttgtaacc gattttaacg gtccaacggg aacagttacg tatacagttg     780
```

-continued attttcaggg taaggcagaa accgtaaagg ttagtgtagt tgatgaagaa gggaaagttg 840
ttgcttcaac tgaaggcctc tctggtaatg ttgagattcc taacgttatc ctttgggaac 900
ctttaaatac ctatctctat caaattaaag ttgagttagt aaatgatggt ctaactattg 960
atgtatacga agagccattt ggagttcgaa ccgttgaagt aaacgacggg aaattcctca 1020
ttaataacaa accattttat tttaaagggt tcggaaaaca cgaggatact ccaataaatg 1080
gaagaggctt taatgaagca tcaaatgtaa tggattttaa tattttgaaa tggatcggtg 1140
cgaattcctt tcggacggcg cactatcctt attctgaaga actgatgcgg ctcgcagatc 1200
gtgaagggtt agtcgtcata gatgaaaccc cagcagttgg tgttcatttg aactttatgg 1260
caacgactgg tttgggcgaa ggttcagaga gagtgagtac ttgggaaaaa atccggacct 1320
ttgaacatca tcaagatgta ctgagagagc tggtttctcg tgataaaaac cacccctctg 1380
ttgtcatgtg gtcgattgca aatgaagcgg ctacggaaga agaaggcgct tatgaatact 1440
ttaagccatt agttgaatta acgaaagaat tagatccaca aaaacgccca gttaccattg 1500
ttttgttcgt aatggcgaca ccagaaacag ataaagtggc ggagttaatt gatgtgattg 1560
cattgaatcg atacaacggc tggtattttg atggggggtga tcttgaagcc gcgaaagtcc 1620
accttcgtca ggaatttcat gcgtggaata aacgctgtcc aggaaaacct ataatgataa 1680
cagagtatgg ggctgatacc gtagctggtt ttcatgatat tgatccggtt atgtttacag 1740
aagagtatca ggttgaatat taccaagcaa atcatgtagt atttgatgaa tttgagaact 1800
ttgttggcga gcaggcctgg aattttgcag actttgctac aagccagggt gtcatgcgtg 1860
ttcaaggtaa caaaaaaggt gttttcacac gcgaccgcaa accaaaatta gcagcacatg 1920
ttttccgcga acgttggaca aacatcccgg atttcggtta taaaaattaa taaaaagctg 1980
gttctccaat aggaggccag ctttttttaca tggatacaat ggttgtaaat taaaaaccct 2040
cttcattttt tatataaaaa tgaagagggt tttaattttt taaatgttat tacatttttt 2100

<210> SEQ ID NO 2
<211> LENGTH: 602
<212> TYPE: PRT
<213> ORGANISM: Bacillus sp.

<400> SEQUENCE: 2

Met Leu Tyr Pro Ile Asn Thr Glu Thr Arg Gly Val Phe Asp Leu Asn
1 5 10 15

Gly Val Trp Asn Phe Lys Leu Asp Tyr Gly Lys Gly Leu Glu Glu Lys
20 25 30

Trp Tyr Glu Ser Lys Leu Thr Asp Thr Ile Ser Met Ala Val Pro Ser
35 40 45

Ser Tyr Asn Asp Ile Gly Val Thr Lys Glu Ile Arg Asn His Ile Gly
50 55 60

Tyr Val Trp Tyr Glu Arg Glu Phe Thr Val Pro Ala Tyr Leu Lys Asp
65 70 75 80

Gln Arg Ile Val Leu Arg Phe Gly Ser Ala Thr His Lys Ala Ile Val
85 90 95

Tyr Val Asn Gly Glu Leu Val Val Glu His Lys Gly Gly Phe Leu Pro
100 105 110

Phe Glu Ala Glu Ile Asn Asn Ser Leu Arg Asp Gly Met Asn Arg Val
115 120 125

Thr Val Ala Val Asp Asn Ile Leu Asp Asp Ser Thr Leu Pro Val Gly
130 135 140

-continued

```
Leu Tyr Ser Glu Arg His Glu Glu Gly Leu Gly Lys Val Ile Arg Asn
145                 150                 155                 160

Lys Pro Asn Phe Asp Phe Phe Asn Tyr Ala Gly Leu His Arg Pro Val
                165                 170                 175

Lys Ile Tyr Thr Thr Pro Phe Thr Tyr Val Glu Asp Ile Ser Val Val
            180                 185                 190

Thr Asp Phe Asn Gly Pro Thr Gly Thr Val Thr Tyr Thr Val Asp Phe
        195                 200                 205

Gln Gly Lys Ala Glu Thr Val Lys Val Ser Val Val Asp Glu Glu Gly
    210                 215                 220

Lys Val Val Ala Ser Thr Glu Gly Leu Ser Gly Asn Val Glu Ile Pro
225                 230                 235                 240

Asn Val Ile Leu Trp Glu Pro Leu Asn Thr Tyr Leu Tyr Gln Ile Lys
                245                 250                 255

Val Glu Leu Val Asn Asp Gly Leu Thr Ile Asp Val Tyr Glu Glu Pro
            260                 265                 270

Phe Gly Val Arg Thr Val Glu Val Asn Asp Gly Lys Phe Leu Ile Asn
        275                 280                 285

Asn Lys Pro Phe Tyr Phe Lys Gly Phe Gly Lys His Glu Asp Thr Pro
    290                 295                 300

Ile Asn Gly Arg Gly Phe Asn Glu Ala Ser Asn Val Met Asp Phe Asn
305                 310                 315                 320

Ile Leu Lys Trp Ile Gly Ala Asn Ser Phe Arg Thr Ala His Tyr Pro
                325                 330                 335

Tyr Ser Glu Glu Leu Met Arg Leu Ala Asp Arg Glu Gly Leu Val Val
            340                 345                 350

Ile Asp Glu Thr Pro Ala Val Gly Val His Leu Asn Phe Met Ala Thr
        355                 360                 365

Thr Gly Leu Gly Glu Gly Ser Glu Arg Val Ser Thr Trp Glu Lys Ile
    370                 375                 380

Arg Thr Phe Glu His His Gln Asp Val Leu Arg Glu Leu Val Ser Arg
385                 390                 395                 400

Asp Lys Asn His Pro Ser Val Val Met Trp Ser Ile Ala Asn Glu Ala
                405                 410                 415

Ala Thr Glu Glu Glu Gly Ala Tyr Glu Tyr Phe Lys Pro Leu Val Glu
            420                 425                 430

Leu Thr Lys Glu Leu Asp Pro Gln Lys Arg Pro Val Thr Ile Val Leu
        435                 440                 445

Phe Val Met Ala Thr Pro Glu Thr Asp Lys Val Ala Glu Leu Ile Asp
    450                 455                 460

Val Ile Ala Leu Asn Arg Tyr Asn Gly Trp Tyr Phe Asp Gly Gly Asp
465                 470                 475                 480

Leu Glu Ala Ala Lys Val His Leu Arg Gln Glu Phe His Ala Trp Asn
                485                 490                 495

Lys Arg Cys Pro Gly Lys Pro Ile Met Ile Thr Glu Tyr Gly Ala Asp
            500                 505                 510

Thr Val Ala Gly Phe His Asp Ile Asp Pro Val Met Phe Thr Glu Glu
        515                 520                 525

Tyr Gln Val Glu Tyr Tyr Gln Ala Asn His Val Val Phe Asp Glu Phe
    530                 535                 540

Glu Asn Phe Val Gly Glu Gln Ala Trp Asn Phe Ala Asp Phe Ala Thr
545                 550                 555                 560

Ser Gln Gly Val Met Arg Val Gln Gly Asn Lys Lys Gly Val Phe Thr
```

-continued 565 570 575

Arg Asp Arg Lys Pro Lys Leu Ala Ala His Val Phe Arg Glu Arg Trp
580 585 590

Thr Asn Ile Pro Asp Phe Gly Tyr Lys Asn
595 600

<210> SEQ ID NO 3
<211> LENGTH: 372
<212> TYPE: PRT
<213> ORGANISM: Enterobacter sp. / Salmonella sp.
<220> FEATURE:
<221> NAME/KEY: VARIANT
<222> LOCATION: (1)...(372)
<223> OTHER INFORMATION: Xaa = Any Amino Acid

<400> SEQUENCE: 3

Gly Lys Leu Ser Pro Thr Pro Thr Ala Tyr Ile Gln Asp Val Thr Val
1 5 10 15

Xaa Thr Asp Val Leu Glu Asn Thr Glu Gln Ala Thr Val Leu Gly Asn
20 25 30

Val Gly Ala Asp Gly Asp Ile Arg Val Glu Leu Arg Asp Gly Gln Gln
35 40 45

Gln Ile Val Ala Gln Gly Leu Gly Ala Thr Gly Ile Phe Glu Leu Asp
50 55 60

Asn Pro His Leu Trp Glu Pro Gly Glu Gly Tyr Leu Tyr Glu Leu Arg
65 70 75 80

Val Thr Cys Glu Ala Asn Gly Glu Cys Asp Glu Tyr Pro Val Arg Val
85 90 95

Gly Ile Arg Ser Ile Thr Xaa Lys Gly Glu Gln Phe Leu Ile Asn His
100 105 110

Lys Pro Phe Tyr Leu Thr Gly Phe Gly Arg His Glu Asp Ala Asp Phe
115 120 125

Arg Gly Lys Gly Phe Asp Pro Val Leu Met Val His Asp His Ala Leu
130 135 140

Met Asn Trp Ile Gly Ala Asn Ser Tyr Arg Thr Ser His Tyr Pro Tyr
145 150 155 160

Ala Glu Lys Met Leu Asp Trp Ala Asp Glu His Val Ile Val Val Ile
165 170 175

Asn Glu Thr Ala Ala Gly Gly Phe Asn Thr Leu Ser Leu Gly Ile Thr
180 185 190

Phe Asp Ala Gly Glu Arg Pro Lys Glu Leu Tyr Ser Glu Glu Ala Ile
195 200 205

Asn Gly Glu Thr Ser Gln Gln Ala His Leu Gln Ala Ile Lys Glu Leu
210 215 220

Ile Ala Arg Asp Lys Asn His Pro Ser Val Val Cys Trp Ser Ile Ala
225 230 235 240

Asn Glu Pro Asp Thr Arg Pro Asn Gly Ala Arg Glu Tyr Phe Ala Pro
245 250 255

Leu Ala Lys Ala Thr Arg Glu Leu Asp Pro Thr Arg Pro Ile Thr Cys
260 265 270

Val Asn Val Met Phe Cys Asp Ala Glu Ser Asp Thr Ile Thr Asp Leu
275 280 285

Phe Asp Val Val Cys Leu Asn Arg Tyr Tyr Gly Trp Tyr Val Gln Ser
290 295 300

Gly Asp Leu Glu Lys Ala Glu Gln Met Leu Glu Gln Glu Leu Leu Ala
305 310 315 320

-continued

```
Trp Gln Ser Lys Leu His Arg Pro Ile Ile Ile Thr Glu Tyr Gly Val
                325                 330                 335

Asp Thr Leu Ala Gly Met Pro Ser Val Tyr Pro Asp Met Trp Ser Glu
            340                 345                 350

Lys Tyr Gln Trp Lys Trp Leu Glu Met Tyr His Arg Val Phe Asp Arg
        355                 360                 365

Gly Ser Val Cys
    370


<210> SEQ ID NO 4
<211> LENGTH: 376
<212> TYPE: PRT
<213> ORGANISM: Staphylococcus homini
<220> FEATURE:
<221> NAME/KEY: VARIANT
<222> LOCATION: (1)...(376)
<223> OTHER INFORMATION: Xaa = Any Amino Acid

<400> SEQUENCE: 4

Gly Leu Ser Gly Asn Val Glu Ile Pro Asn Val Ile Leu Trp Glu Pro
 1               5                  10                  15

Leu Asn Thr Tyr Leu Tyr Gln Ile Lys Val Glu Leu Val Asn Asp Gly
            20                  25                  30

Leu Thr Ile Asp Val Tyr Glu Glu Pro Phe Gly Val Arg Thr Val Glu
        35                  40                  45

Val Asn Asp Gly Lys Phe Leu Ile Asn Asn Lys Pro Phe Tyr Phe Lys
    50                  55                  60

Gly Phe Gly Lys His Glu Asp Thr Pro Ile Asn Gly Arg Gly Phe Asn
65                  70                  75                  80

Glu Ala Ser Asn Val Met Asp Phe Asn Ile Leu Lys Trp Ile Gly Ala
                85                  90                  95

Asn Ser Phe Arg Thr Ala His Tyr Pro Tyr Ser Glu Glu Leu Met Arg
            100                 105                 110

Leu Ala Asp Arg Glu Gly Leu Val Val Ile Asp Glu Thr Pro Ala Val
        115                 120                 125

Gly Val His Leu Asn Phe Met Ala Thr Thr Gly Leu Gly Glu Gly Ser
    130                 135                 140

Glu Arg Val Ser Thr Trp Glu Lys Ile Arg Thr Phe Glu His His Gln
145                 150                 155                 160

Asp Val Leu Arg Glu Leu Val Ser Arg Asp Lys Asn His Pro Ser Val
                165                 170                 175

Val Met Trp Ser Ile Ala Asn Glu Ala Ala Thr Glu Glu Glu Gly Ala
            180                 185                 190

Tyr Glu Tyr Phe Lys Pro Leu Gly Gly Ala Ala Lys Glu Leu Asp Pro
        195                 200                 205

Xaa Lys Arg Pro Val Thr Ile Val Leu Phe Val Met Ala Thr Pro Glu
    210                 215                 220

Thr Asp Lys Val Ala Glu Leu Ile Asp Val Ile Ala Leu Asn Arg Tyr
225                 230                 235                 240

Asn Gly Trp Tyr Phe Asp Gly Gly Asp Leu Glu Ala Ala Lys Val His
                245                 250                 255

Leu Arg Gln Glu Phe His Ala Trp Asn Lys Arg Cys Pro Gly Lys Pro
            260                 265                 270

Ile Met Ile Thr Glu Tyr Gly Ala Asp Thr Val Ala Gly Phe His Asp
        275                 280                 285
```

-continued

```
Ile Asp Pro Val Met Phe Thr Glu Glu Tyr Gln Val Glu Tyr Tyr Gln
    290                 295                 300

Ala Asn His Val Val Phe Asp Glu Phe Glu Asn Phe Val Gly Glu Gln
305                 310                 315                 320

Ala Trp Asn Phe Ala Asp Phe Ala Thr Ser Gln Gly Val Met Arg Val
                325                 330                 335

Gln Gly Asn Lys Lys Gly Val Phe Thr Arg Asp Arg Lys Pro Xaa Leu
            340                 345                 350

Ala Ala His Val Phe Arg Glu Arg Arg Thr Asn Ile Pro Asp Phe Gly
        355                 360                 365

Tyr Lys Asn Ala Ser His His His
    370                 375


<210> SEQ ID NO 5
<211> LENGTH: 540
<212> TYPE: PRT
<213> ORGANISM: Staphylococcus warneri
<220> FEATURE:
<221> NAME/KEY: VARIANT
<222> LOCATION: (1)...(540)
<223> OTHER INFORMATION: Xaa = Any Amino Acid

<400> SEQUENCE: 5

Leu Xaa Leu Leu His Pro Ile Thr Thr Gly Thr Arg Gly Gly Phe Ala
 1               5                  10                  15

Leu Tyr Gly Xaa Xaa Asn Leu Met Leu Asp Tyr Gly Xaa Gly Leu Thr
            20                  25                  30

Asp Thr Trp Thr Xaa Ser Leu Leu Thr Glu Leu Ser Arg Leu Val Val
        35                  40                  45

Leu Ser Trp Thr Thr His Xaa Leu Thr Gly Glu Xaa Pro Ala Ile Ser
    50                  55                  60

Ile Leu Trp Pro Asn Ser Glu Leu Thr Val Ser Xaa Leu Tyr Xaa Gly
65                  70                  75                  80

Ser Leu Xaa Ser Ser Ser Xaa Leu Cys Ser Ser Leu Thr Xaa His Val
                85                  90                  95

Val Ile Cys Gln Xaa Val Thr Leu Xaa Val Asp His Thr Gly Leu Ile
            100                 105                 110

Xaa Xaa Phe Glu Phe Met Ser Thr Thr Cys Cys Xaa Xaa Asp Glu Leu
        115                 120                 125

Val Thr Gly Thr Leu Ala Xaa Ile Leu Tyr His Xaa Ile Leu Pro His
    130                 135                 140

Gly Leu Tyr Arg Lys Arg His Glu Xaa Gly Leu Gly Lys Xaa Asn Phe
145                 150                 155                 160

Tyr Xaa Leu His Phe Ala Phe Phe Xaa Tyr Ala Xaa Leu Xaa Arg Thr
                165                 170                 175

Val Xaa Met Tyr Xaa Asn Leu Val Arg Xaa Gln Asp Ile Xaa Val Val
            180                 185                 190

Thr Xaa Xaa His Xaa Xaa Xaa Xaa Thr Val Glu Gln Cys Val Xaa Xaa
        195                 200                 205

Asn Xaa Lys Ile Xaa Ser Val Lys Ile Thr Ile Leu Asp Glu Asn Asp
    210                 215                 220

His Ala Ile Xaa Glu Ser Glu Gly Ala Lys Gly Asn Val Thr Ile Gln
225                 230                 235                 240

Asn Pro Ile Leu Trp Gln Pro Leu His Ala Tyr Leu Tyr Asn Met Lys
                245                 250                 255

Val Glu Leu Leu Asn Asp Asn Glu Cys Val Asp Val Tyr Thr Glu Arg
```

-continued

```
            260                 265                 270

Phe Gly Ile Arg Ser Val Glu Val Lys Asp Gly Gln Phe Leu Ile Asn
        275                 280                 285

Asp Lys Pro Phe Tyr Phe Lys Gly Phe Gly Lys His Glu Asp Thr Tyr
    290                 295                 300

Xaa Asn Gly Arg Gly Leu Asn Glu Ser Ala Asn Val Met Asp Ile Asn
305                 310                 315                 320

Leu Met Lys Trp Ile Gly Ala Asn Ser Phe Arg Thr Ser His Tyr Pro
                325                 330                 335

Tyr Ser Glu Glu Met Met Arg Leu Ala Asp Glu Gln Gly Ile Val Val
            340                 345                 350

Ile Asp Glu Thr Thr Xaa Val Gly Ile His Leu Asn Phe Met Xaa Thr
        355                 360                 365

Leu Gly Gly Ser Xaa Ala His Asp Thr Trp Xaa Glu Phe Asp Thr Leu
    370                 375                 380

Glu Phe His Lys Glu Val Ile Xaa Asp Leu Ile Xaa Arg Asp Lys Asn
385                 390                 395                 400

His Ala Trp Val Val Met Trp Xaa Phe Gly Asn Glu Xaa Gly Xaa Asn
                405                 410                 415

Lys Gly Gly Ala Lys Ala Xaa Phe Glu Pro Phe Val Asn Leu Ala Gly
            420                 425                 430

Glu Lys Asp Xaa Xaa Xaa Xaa Pro Val Thr Ile Val Thr Ile Leu Xaa
        435                 440                 445

Ala Xaa Arg Asn Val Cys Glu Val Xaa Asp Leu Val Asp Val Val Cys
    450                 455                 460

Leu Xaa Xaa Xaa Xaa Gly Trp Tyr Xaa Gln Ser Gly Asp Leu Glu Gly
465                 470                 475                 480

Ala Lys Xaa Ala Leu Asp Lys Glu Xaa Xaa Glu Trp Trp Lys Xaa Gln
                485                 490                 495

Xaa Asn Lys Pro Xaa Met Phe Thr Glu Tyr Gly Val Asp Xaa Val Val
            500                 505                 510

Gly Leu Xaa Xaa Xaa Pro Asp Lys Met Xaa Pro Glu Glu Tyr Lys Met
        515                 520                 525

Xaa Phe Tyr Lys Gly Tyr Xaa Lys Ile Met Asp Lys
    530                 535                 540


<210> SEQ ID NO 6
<211> LENGTH: 563
<212> TYPE: PRT
<213> ORGANISM: Thermotoga maritima
<220> FEATURE:
<221> NAME/KEY: VARIANT
<222> LOCATION: (1)...(563)
<223> OTHER INFORMATION: Xaa = Any Amino Acid

<400> SEQUENCE: 6

Met Val Arg Pro Gln Arg Asn Lys Lys Arg Phe Ile Leu Ile Leu Asn
 1               5                  10                  15

Gly Val Trp Asn Leu Glu Val Thr Ser Lys Asp Arg Pro Ile Ala Val
            20                  25                  30

Pro Gly Ser Trp Asn Glu Gln Tyr Gln Asp Leu Cys Tyr Glu Glu Gly
        35                  40                  45

Pro Phe Thr Tyr Lys Thr Thr Phe Tyr Val Pro Lys Xaa Leu Ser Gln
    50                  55                  60

Lys His Ile Arg Leu Tyr Phe Ala Ala Val Asn Thr Asp Cys Glu Val
65                  70                  75                  80
```

-continued

Phe Leu Asn Gly Glu Lys Val Gly Glu Asn His Ile Glu Tyr Leu Pro
85 90 95

Phe Glu Val Asp Val Thr Gly Lys Val Lys Ser Gly Glu Asn Glu Leu
100 105 110

Arg Val Val Val Glu Asn Arg Leu Lys Val Gly Gly Phe Pro Ser Lys
115 120 125

Val Pro Asp Ser Gly Thr His Thr Val Gly Phe Phe Gly Ser Phe Pro
130 135 140

Pro Ala Asn Phe Asp Phe Phe Pro Tyr Gly Gly Ile Ile Arg Pro Val
145 150 155 160

Leu Ile Glu Phe Thr Asp His Ala Arg Ile Leu Asp Ile Trp Val Asp
165 170 175

Thr Ser Glu Ser Glu Pro Glu Lys Lys Leu Gly Lys Val Lys Val Lys
180 185 190

Ile Glu Val Ser Glu Glu Ala Val Gly Gln Glu Met Thr Ile Lys Leu
195 200 205

Gly Glu Glu Glu Lys Lys Ile Arg Thr Ser Asn Arg Phe Val Glu Gly
210 215 220

Glu Phe Ile Leu Glu Asn Ala Arg Phe Trp Ser Leu Glu Asp Pro Tyr
225 230 235 240

Leu Tyr Pro Leu Lys Val Glu Leu Glu Lys Asp Glu Tyr Thr Leu Asp
245 250 255

Ile Gly Ile Arg Thr Ile Ser Trp Asp Glu Lys Arg Leu Tyr Leu Asn
260 265 270

Gly Lys Pro Val Phe Leu Lys Gly Phe Gly Lys His Glu Glu Phe Pro
275 280 285

Val Leu Gly Gln Gly Thr Phe Tyr Pro Leu Met Ile Lys Asp Phe Asn
290 295 300

Leu Leu Lys Trp Ile Asn Ala Asn Ser Phe Arg Thr Ser His Tyr Pro
305 310 315 320

Tyr Ser Glu Glu Trp Leu Asp Leu Ala Asp Arg Leu Gly Ile Leu Val
325 330 335

Ile Asp Glu Ala Pro His Val Gly Ile Thr Arg Tyr His Tyr Asn Pro
340 345 350

Glu Thr Gln Lys Ile Ala Glu Asp Asn Ile Arg Arg Met Ile Asp Arg
355 360 365

His Lys Asn His Pro Ser Val Ile Met Trp Ser Val Ala Asn Glu Pro
370 375 380

Glu Ser Asn His Pro Asp Ala Glu Gly Phe Phe Lys Ala Leu Tyr Glu
385 390 395 400

Thr Ala Asn Glu Met Asp Arg Thr Arg Pro Val Val Met Val Ser Met
405 410 415

Met Asp Ala Pro Asp Glu Arg Thr Arg Asp Val Ala Leu Lys Tyr Phe
420 425 430

Asp Ile Val Cys Val Asn Arg Tyr Tyr Gly Trp Tyr Ile Tyr Gln Gly
435 440 445

Arg Ile Glu Glu Gly Leu Gln Ala Leu Glu Lys Asp Ile Glu Glu Leu
450 455 460

Tyr Ala Arg His Arg Lys Pro Ile Phe Val Thr Glu Phe Gly Ala Asp
465 470 475 480

Ala Ile Ala Gly Ile His Tyr Asp Pro Pro Gln Met Phe Ser Glu Glu
485 490 495

-continued

```
Tyr Gln Ala Glu Leu Val Glu Lys Thr Ile Arg Leu Leu Leu Lys Lys
            500                 505                 510

Asp Tyr Ile Ile Gly Thr His Val Trp Ala Phe Ala Asp Phe Lys Thr
        515                 520                 525

Pro Gln Asn Val Arg Arg Pro Ile Leu Asn His Lys Gly Val Phe Thr
    530                 535                 540

Arg Asp Arg Gln Pro Lys Leu Val Ala His Val Leu Arg Arg Leu Trp
545                 550                 555                 560

Ser Glu Val


<210> SEQ ID NO 7
<211> LENGTH: 1806
<212> TYPE: DNA
<213> ORGANISM: Bacillus sp.
<220> FEATURE:
<221> NAME/KEY: CDS
<222> LOCATION: (1)...(1806)

<400> SEQUENCE: 7

atg tta tat cca atc aat aca gaa acc cga gga gtt ttt gat tta aat       48
Met Leu Tyr Pro Ile Asn Thr Glu Thr Arg Gly Val Phe Asp Leu Asn
 1               5                  10                  15

ggg gtc tgg aat ttt aaa tta gat tac ggc aaa gga ctg gaa gaa aag       96
Gly Val Trp Asn Phe Lys Leu Asp Tyr Gly Lys Gly Leu Glu Glu Lys
            20                  25                  30

tgg tat gaa tca aaa ctg aca gat acc ata tca atg gct gta cct tcc      144
Trp Tyr Glu Ser Lys Leu Thr Asp Thr Ile Ser Met Ala Val Pro Ser
        35                  40                  45

tcc tat aat gat atc ggt gtt acg aag gaa att cga aac cat atc ggc      192
Ser Tyr Asn Asp Ile Gly Val Thr Lys Glu Ile Arg Asn His Ile Gly
    50                  55                  60

tat gta tgg tac gag cgt gaa ttt acc gtt cct gct tat tta aaa gat      240
Tyr Val Trp Tyr Glu Arg Glu Phe Thr Val Pro Ala Tyr Leu Lys Asp
 65                  70                  75                  80

cag cgc atc gtc ctg cgt ttt ggt tca gca aca cat aag gct att gta      288
Gln Arg Ile Val Leu Arg Phe Gly Ser Ala Thr His Lys Ala Ile Val
                85                  90                  95

tac gtt aac gga gaa cta gta gtt gaa cac aaa ggc ggc ttc tta ccg      336
Tyr Val Asn Gly Glu Leu Val Val Glu His Lys Gly Gly Phe Leu Pro
            100                 105                 110

ttt gag gca gaa ata aac aac agc tta aga gac gga atg aat cgt gta      384
Phe Glu Ala Glu Ile Asn Asn Ser Leu Arg Asp Gly Met Asn Arg Val
        115                 120                 125

aca gta gcg gtt gat aat att tta gat gat tct acg ctc cca gtt ggg      432
Thr Val Ala Val Asp Asn Ile Leu Asp Asp Ser Thr Leu Pro Val Gly
    130                 135                 140

cta tat agt gaa aga cat gaa gaa ggt ttg gga aaa gtg att cgt aat      480
Leu Tyr Ser Glu Arg His Glu Glu Gly Leu Gly Lys Val Ile Arg Asn
145                 150                 155                 160

aaa cct aat ttt gac ttc ttt aac tat gca ggc tta cat cgt cct gta      528
Lys Pro Asn Phe Asp Phe Phe Asn Tyr Ala Gly Leu His Arg Pro Val
                165                 170                 175

aaa att tat aca acc cct ttt acc tat gtt gag gat ata tcg gtt gta      576
Lys Ile Tyr Thr Thr Pro Phe Thr Tyr Val Glu Asp Ile Ser Val Val
            180                 185                 190

acc gat ttt aac ggt cca acg gga aca gtt acg tat aca gtt gat ttt      624
Thr Asp Phe Asn Gly Pro Thr Gly Thr Val Thr Tyr Thr Val Asp Phe
        195                 200                 205

cag ggt aag gca gaa acc gta aag gtt agt gta gtt gat gaa gaa ggg      672
Gln Gly Lys Ala Glu Thr Val Lys Val Ser Val Val Asp Glu Glu Gly
```

-continued

```
    210                 215                 220

aaa gtt gtt gct tca act gaa ggc ctc tct ggt aat gtt gag att cct      720
Lys Val Val Ala Ser Thr Glu Gly Leu Ser Gly Asn Val Glu Ile Pro
225                 230                 235                 240

aac gtt atc ctt tgg gaa cct tta aat acc tat ctc tat caa att aaa      768
Asn Val Ile Leu Trp Glu Pro Leu Asn Thr Tyr Leu Tyr Gln Ile Lys
                245                 250                 255

gtt gag tta gta aat gat ggt cta act att gat gta tac gaa gag cca      816
Val Glu Leu Val Asn Asp Gly Leu Thr Ile Asp Val Tyr Glu Glu Pro
            260                 265                 270

ttt gga gtt cga acc gtt gaa gta aac gac ggg aaa ttc ctc att aat      864
Phe Gly Val Arg Thr Val Glu Val Asn Asp Gly Lys Phe Leu Ile Asn
        275                 280                 285

aac aaa cca ttt tat ttt aaa ggg ttc gga aaa cac gag gat act cca      912
Asn Lys Pro Phe Tyr Phe Lys Gly Phe Gly Lys His Glu Asp Thr Pro
    290                 295                 300

ata aat gga aga ggc ttt aat gaa gca tca aat gta atg gat ttt aat      960
Ile Asn Gly Arg Gly Phe Asn Glu Ala Ser Asn Val Met Asp Phe Asn
305                 310                 315                 320

att ttg aaa tgg atc ggt gcg aat tcc ttt cgg acg gcg cac tat cct     1008
Ile Leu Lys Trp Ile Gly Ala Asn Ser Phe Arg Thr Ala His Tyr Pro
                325                 330                 335

tat tct gaa gaa ctg atg cgg ctc gca gat cgt gaa ggg tta gtc gtc     1056
Tyr Ser Glu Glu Leu Met Arg Leu Ala Asp Arg Glu Gly Leu Val Val
            340                 345                 350

ata gat gaa acc cca gca gtt ggt gtt cat ttg aac ttt atg gca acg     1104
Ile Asp Glu Thr Pro Ala Val Gly Val His Leu Asn Phe Met Ala Thr
        355                 360                 365

act ggt ttg ggc gaa ggt tca gag aga gtg agt act tgg gaa aaa atc     1152
Thr Gly Leu Gly Glu Gly Ser Glu Arg Val Ser Thr Trp Glu Lys Ile
    370                 375                 380

cgg acc ttt gaa cat cat caa gat gta ctg aga gag ctg gtt tct cgt     1200
Arg Thr Phe Glu His His Gln Asp Val Leu Arg Glu Leu Val Ser Arg
385                 390                 395                 400

gat aaa aac cac ccc tct gtt gtc atg tgg tcg att gca aat gaa gcg     1248
Asp Lys Asn His Pro Ser Val Val Met Trp Ser Ile Ala Asn Glu Ala
                405                 410                 415

gct acg gaa gaa gaa ggc gct tat gaa tac ttt aag cca tta gtt gaa     1296
Ala Thr Glu Glu Glu Gly Ala Tyr Glu Tyr Phe Lys Pro Leu Val Glu
            420                 425                 430

tta acg aaa gaa tta gat cca caa aaa cgc cca gtt acc att gtt ttg     1344
Leu Thr Lys Glu Leu Asp Pro Gln Lys Arg Pro Val Thr Ile Val Leu
        435                 440                 445

ttc gta atg gcg aca cca gaa aca gat aaa gtg gcg gag tta att gat     1392
Phe Val Met Ala Thr Pro Glu Thr Asp Lys Val Ala Glu Leu Ile Asp
    450                 455                 460

gtg att gca ttg aat cga tac aac ggc tgg tat ttt gat ggg ggt gat     1440
Val Ile Ala Leu Asn Arg Tyr Asn Gly Trp Tyr Phe Asp Gly Gly Asp
465                 470                 475                 480

ctt gaa gcc gcg aaa gtc cac ctt cgt cag gaa ttt cat gcg tgg aat     1488
Leu Glu Ala Ala Lys Val His Leu Arg Gln Glu Phe His Ala Trp Asn
                485                 490                 495

aaa cgc tgt cca gga aaa cct ata atg ata aca gag tat ggg gct gat     1536
Lys Arg Cys Pro Gly Lys Pro Ile Met Ile Thr Glu Tyr Gly Ala Asp
            500                 505                 510

acc gta gct ggt ttt cat gat att gat ccg gtt atg ttt aca gaa gag     1584
Thr Val Ala Gly Phe His Asp Ile Asp Pro Val Met Phe Thr Glu Glu
        515                 520                 525

tat cag gtt gaa tat tac caa gca aat cat gta gta ttt gat gaa ttt     1632
```

-continued

```
Tyr Gln Val Glu Tyr Tyr Gln Ala Asn His Val Val Phe Asp Glu Phe
    530                 535                 540

gag aac ttt gtt ggc gag cag gcc tgg aat ttt gca gac ttt gct aca     1680
Glu Asn Phe Val Gly Glu Gln Ala Trp Asn Phe Ala Asp Phe Ala Thr
545                 550                 555                 560

agc cag ggt gtc atg cgt gtt caa ggt aac aaa aaa ggt gtt ttc aca     1728
Ser Gln Gly Val Met Arg Val Gln Gly Asn Lys Lys Gly Val Phe Thr
                565                 570                 575

cgc gac cgc aaa cca aaa tta gca gca cat gtt ttc cgc gaa cgt tgg     1776
Arg Asp Arg Lys Pro Lys Leu Ala Ala His Val Phe Arg Glu Arg Trp
            580                 585                 590

aca aac atc ccg gat ttc ggt tat aaa aat                             1806
Thr Asn Ile Pro Asp Phe Gly Tyr Lys Asn
        595                 600


<210> SEQ ID NO 8
<211> LENGTH: 602
<212> TYPE: PRT
<213> ORGANISM: Bacillus sp.

<400> SEQUENCE: 8

Met Leu Tyr Pro Ile Asn Thr Glu Thr Arg Gly Val Phe Asp Leu Asn Gly
 1              5                   10                  15

Val Trp Asn Phe Lys Leu Asp Tyr Gly Lys Gly Leu Glu Glu Lys Trp
        20                  25                  30

Tyr Glu Ser Lys Leu Thr Asp Thr Ile Ser Met Ala Val Pro Ser Ser
    35                  40                  45

Tyr Asn Asp Ile Gly Val Thr Lys Glu Ile Arg Asn His Ile Gly Tyr
50                  55                  60                  65

Val Trp Tyr Glu Arg Glu Phe Thr Val Pro Ala Tyr Leu Lys Asp Gln
                70                  75                  80

Arg Ile Val Leu Arg Phe Gly Ser Ala Thr His Lys Ala Ile Val Tyr
            85                  90                  95

Val Asn Gly Glu Leu Val Val Glu His Lys Gly Gly Phe Leu Pro Phe
        100                 105                 110

Glu Ala Glu Ile Asn Asn Ser Leu Arg Asp Gly Met Asn Arg Val Thr
    115                 120                 125

Val Ala Val Asp Asn Ile Leu Asp Asp Ser Thr Leu Pro Val Gly Leu
130                 135                 140                 145

Tyr Ser Glu Arg His Glu Glu Gly Leu Gly Lys Val Ile Arg Asn Lys
                150                 155                 160

Pro Asn Phe Asp Phe Phe Asn Tyr Ala Gly Leu His Arg Pro Val Lys
            165                 170                 175

Ile Tyr Thr Thr Pro Phe Thr Tyr Val Glu Asp Ile Ser Val Val Thr
        180                 185                 190

Asp Phe Asn Gly Pro Thr Gly Thr Val Thr Tyr Thr Val Asp Phe Gln
    195                 200                 205

Gly Lys Ala Glu Thr Val Lys Val Ser Val Val Asp Glu Glu Gly Lys
210                 215                 220                 225

Val Val Ala Ser Thr Glu Gly Leu Ser Gly Asn Val Glu Ile Pro Asn
                 230                 235                 240

Val Ile Leu Trp Glu Pro Leu Asn Thr Tyr Leu Tyr Gln Ile Lys Val
            245                 250                 255

Glu Leu Val Asn Asp Gly Leu Thr Ile Asp Val Tyr Glu Glu Pro Phe
        260                 265                 270

Gly Val Arg Thr Val Glu Val Asn Asp Gly Lys Phe Leu Ile Asn Asn
```

-continued

```
    275                 280                 285

Lys Pro Phe Tyr Phe Lys Gly Phe Gly Lys His Glu Asp Thr Pro Ile
290                 295                 300                 305

Asn Gly Arg Gly Phe Asn Glu Ala Ser Asn Val Met Asp Phe Asn Ile
                310                 315                 320

Leu Lys Trp Ile Gly Ala Asn Ser Phe Arg Thr Ala His Tyr Pro Tyr
            325                 330                 335

Ser Glu Glu Leu Met Arg Leu Ala Asp Arg Glu Gly Leu Val Val Ile
        340                 345                 350

Asp Glu Thr Pro Ala Val Gly Val His Leu Asn Phe Met Ala Thr Thr
    355                 360                 365

Gly Leu Gly Glu Gly Ser Glu Arg Val Ser Thr Trp Glu Lys Ile Arg
370                 375                 380                 385

Thr Phe Glu His His Gln Asp Val Leu Arg Glu Leu Val Ser Arg Asp
                390                 395                 400

Lys Asn His Pro Ser Val Val Met Trp Ser Ile Ala Asn Glu Ala Ala
            405                 410                 415

Thr Glu Glu Glu Gly Ala Tyr Glu Tyr Phe Lys Pro Leu Val Glu Leu
        420                 425                 430

Thr Lys Glu Leu Asp Pro Gln Lys Arg Pro Val Thr Ile Val Leu Phe
    435                 440                 445

Val Met Ala Thr Pro Glu Thr Asp Lys Val Ala Glu Leu Ile Asp Val
450                 455                 460                 465

Ile Ala Leu Asn Arg Tyr Asn Gly Trp Tyr Phe Asp Gly Gly Asp Leu
                470                 475                 480

Glu Ala Ala Lys Val His Leu Arg Gln Glu Phe His Ala Trp Asn Lys
            485                 490                 495

Arg Cys Pro Gly Lys Pro Ile Met Ile Thr Glu Tyr Gly Ala Asp Thr
        500                 505                 510

Val Ala Gly Phe His Asp Ile Asp Pro Val Met Phe Thr Glu Glu Tyr
    515                 520                 525

Gln Val Glu Tyr Tyr Gln Ala Asn His Val Val Phe Asp Glu Phe Glu
530                 535                 540                 545

Asn Phe Val Gly Glu Gln Ala Trp Asn Phe Ala Asp Phe Ala Thr Ser
                550                 555                 560

Gln Gly Val Met Arg Val Gln Gly Asn Lys Lys Gly Val Phe Thr Arg
            565                 570                 575

Asp Arg Lys Pro Lys Leu Ala Ala His Val Phe Arg Glu Arg Trp Thr
        580                 585                 590

Asn Ile Pro Asp Phe Gly Tyr Lys Asn
    595                 600
```

```
<210> SEQ ID NO 9
<211> LENGTH: 1327
<212> TYPE: DNA
<213> ORGANISM: Enterobacter sp. / Salmonella sp.
<220> FEATURE:
<221> NAME/KEY: misc_feature
<222> LOCATION: (1)...(1327)
<223> OTHER INFORMATION: n = A,T,C or G

<400> SEQUENCE: 9

cattggggaa actttccccc acacctactg cgtatattca ggatgttacg gttnttactg     60

atgttttgga aaatactgaa caggcgaccg taactgggga atgtgggggc tgatggtgat    120

attcgggttg agcttcgcga tgggcagcaa caaatagtgg cacaagggct gggggccaca    180
```

-continued

```
ggtatatttg aactggataa tcctcatctt tgggaaccag gtgaagggta tttgtacgag    240
ctgcgggtta cctgcgaagc caatggtgag tgtgacgaat atccagtacg tgtcggtatc    300
cgttccatta cggntaaggg tgagcagttt ttgattaacc acaaaccgtt ttatttaacc    360
cggttttggt cgacatgaag atgcagattt tcgcggcaaa ggtttcgacc cgggtgttga    420
tggttcacga ccacgcgttg atgaactgga ttgggctaac tcctatcgca cgtcccacta    480
cccttacgcg gaaaagatgc tcgattgggc tgatgagcac gtatcgtagt gattaatgaa    540
accgcggcgg gtggctttaa cactttatcg ttgggaatca cttttgacgc aggcgaaaga    600
cctaaagaac ttctacagcg aagaggcgat taatggcgag acttcagcag gctcacttgc    660
aggctataaa agagcttatt gcccgggata aaaaccatcc aagtgtagtg tgtggagtat    720
tgccaatgag cccgacaccc gtccaaatgg agccagagag tactttgcgc ctttagctaa    780
ggccactcgt gaactggatc cgacacgtcc gattacctgc gtaaacgtga tgttctgcga    840
tgccgaaagc gacaccatca ccgacctgtt cgacgtggtt tgtctgaatc gctattacgg    900
ctggtatgtg caatcaggtg atttggaaaa agcagaacag atgctggagc aagaactgct    960
ggcctggcag tcaaaactac atcgcccaat tattattacg gaatacggtg tcgatacgct   1020
ggcaggaatg ccctcggttt atcccgacat gtggagtgaa aagtaccagt gaaatggctt   1080
gaaatgtatc accgtgtctt tgaccggggg agcgtttgca agcgcnaagc ttagttaaca   1140
ccggnggtac cgatcacgcg tnaggcgccn cccatggnca tatgngctag cntgcggccg   1200
cnatgcattc tgcagcgatc gcagctgagt acacgagctc acccgcggag tcgacaagat   1260
ccaagtacta cccgggnata cgtaactagt gcatgctcgc gaaatattta ggccttatcg   1320
aattaat                                                             1327
```

<210> SEQ ID NO 10
<211> LENGTH: 729
<212> TYPE: DNA
<213> ORGANISM: Pseudomonas sp.
<220> FEATURE:
<221> NAME/KEY: misc_feature
<222> LOCATION: (1)...(729)
<223> OTHER INFORMATION: n = A,T,C or G

<400> SEQUENCE: 10

```
cttgctggac nacngttnag gatttttaga cacgnggagc taaagcttgc tgaccnaact     60
atcacgccgg ncgtgcangc ttggaccgcg acattncctg acangngaaa nactccgcca    120
tatccatctt tgctggccca acagtgagtt nacngtnncg nacnntnnga nggatcagtg    180
natcgagctc cnttnanntt ctncgctaac ataacatgtn gcatatgtca atnaatnacg    240
ctggncgtgg ancncaccgg gctnattcgn tgnnattcga attgnatgnc aacaactntg    300
ntgcacgntg gnaaanaatt gcgtnacagg gactttggcc ncttcctaaa ccatngcatc    360
ctcccnatgg gctgtacacg aatgngcccc caaaanggcn ttcagaaagg caatttntaa    420
caaggcngan ntttgacttt ttcaactatg cagnnctgca ccggacgctg aaaatgtaca    480
ngaccctggg tacgtncnac caagacatnn aagtngtgac cgactccatt gtnctaaccg    540
ggactgtacc tataatgcgg actatcangg caatgcatga cgtngaancg acacaccagg    600
atnaggaaaa caantggtgg nancncacca ngccatgatt gtcacgtttt gttagcntng    660
anacnaattc nattgctttn ttagcttntt anatnagcct ntttanatta ganttctnan    720
tgagactgt                                                            729
```

-continued

<210> SEQ ID NO 11
<211> LENGTH: 1062
<212> TYPE: DNA
<213> ORGANISM: Salmonella sp.
<220> FEATURE:
<221> NAME/KEY: misc_feature
<222> LOCATION: (1)...(1062)
<223> OTHER INFORMATION: n = A,T,C or G

<400> SEQUENCE: 11
nctcatgacc cncccntttt ngtancntnt ttgnnanctg ctgcannnga tcacnacnng 60
ganncggggn gggttcgnnc tctatggcnc gnggaacnnn atgntggncn acngttnang 120
actgacagac acgtggagct aaagcttgct gccgaactat cactcagntc ntgnaagttg 180
gacaacacat tncctgacan gngaaaagcc cgccatatcc atactgtgct ggcccaacan 240
tgagttcacn gtcgtcgnac tntatgangg atcacctgta tcganctccn ttnatnttct 300
ncagctaaca taactgtgng catatgtcaa tgnatgacct ggtcggtgna ncacaccggg 360
cgtnattgnt gnnattcgaa tttnatgtca acaactttgn tgcangntgg aatgaatctg 420
ggggccaggg actttggcca ncttcctnaa ccattcgcan cctcccccag tgggcttgta 480
cacnattgng ccccaaaaag gcntcagata ggcattttga caagctccan nttaactttt 540
tcaactatgc ngncctgcac cggacgctga aaaangtaca nganccttgt acgttccacc 600
aaganattta aggtgtgacc cacntccatt ttcctaacng gactgtgact nataaaggnt 660
gaccnttcan ggacacattg caatgaccct ttnaaacgga anaacccccg gnttaaagga 720
aaaacaaatt tggttgggna gtccanccaa gggccaatta nttgttncnc gggggantaa 780
ancccccncc aatcgatctt cgaaatttaa acagcgctcc ggccgccacg tgcgaattcc 840
gatatcggat gaggccagcg cnaagcttag ttaacaccgg nggtaccgat cacgcgtnag 900
gcgccnccca tggncatatg ngctagcntg cggccgcnat gcattctgca gcgatcgcag 960
ctgagtacac gagctcaccc gcggagtcga caagatccaa gtactacccg ggnatacgta 1020
actagtgcat gctcgcgaaa tatttaggcc ttatcgaatt aa 1062

<210> SEQ ID NO 12
<211> LENGTH: 1738
<212> TYPE: DNA
<213> ORGANISM: Staphylococcus warneri
<220> FEATURE:
<221> NAME/KEY: misc_feature
<222> LOCATION: (1)...(1738)
<223> OTHER INFORMATION: n = A,T,C or G

<400> SEQUENCE: 12
tanancttgt ntctgctgca cccnatcacg acagggaccc ggggngggtt cgcgctctat 60
ggcncgngga acttaatgct ggactacggt tnaggactga cagacacgtg gactnaaagc 120
ttgctgaccg aactatcacg actggtcgtg ctaagttgga ccacacattn cctgacaggg 180
gaaanacccg ccatatccat cttgtggccc aacagtgagt taaccgtgtc ganctttatat 240 ganggatcac tgnattcgag ctccntctta tgttcttcgc taacatanca tgtngtcata 300
tgtcaatang tgacnctggn cgtggatcac accgggctna ttgntgnatt cgaatttatg 360
tcaacaactt gttgcangnt ggatgaattg gtnacaggga ctttggccan catcctatac 420
catngcatcc ttccccatgg gctttaccga aagcgccacg aaaanggcct cggaaaagnc 480
aatttttacn ggctccactt tgcntttttc aantatgcng anctgnaccg gacggtnana 540
atgtacanga accttgtacg tcnncaagac atttaggttg tgaccgntta gcatnagcng 600

-continued

```
tnntaaacag tagaacaatg tgtganccnt aactaaaaaa tanacagcgt taaaatcacg    660
attctggatg aaaatgatca tgcaatancc gaaagcgaag gcgctaaagg caatgtaact    720
attcaaaatc ctatattgtg gcaaccttta catgcctatt tatacaatat gaaagtagaa    780
ttactcaacg ataatgagtg tgtagatgtt tatacagaac gtttcggtat tcgatctgtn    840
gaagtgaagg atggacagtt tttaattaat gacaaaccat tttatttcaa aggtttcggt    900
aaacatgaag atacctatta aaatggtcga ggcttaaacg aatcagccaa cgtcatggac    960
atcaacttaa tgaaatggat aggtgctaat tcatttagaa cctctcatta cccatattca   1020
gaagaaatga tgcgtttagc agatgaacaa ggtattgtag tgatagatga gacaacangt   1080
gtcggtatac atcttaattt tatggnnacc ttaggtggct ccnttgcaca tgatacatgg   1140
aangaatttg acactctcga gtttcataaa gaagtcatan aagacttgat tgngagagac   1200
aagaatcatg catgggtagt catgtggtna tttggcaatg agcnagggtn aaataaaggg   1260
ggtgctaaag catnctttga gccatttgtt aatttagcag gtgaaaaaga tnntcngnnt   1320
ngcccagtga ctatcgttac tatattanct gcnnancgaa atgtatgtga agttnnagat   1380
ttagtcgatg tggtttgtct nnnnagnnnn tanggttggt atncacaatc aggtgattta   1440
gaaggtgcta aacnagcatt agataaggag ntagncgaat ggtggaaang acaacnaaat   1500
aagccaatna tgtttacaga gtatggtgtg gatanngttg taggtttaca nncgatncct   1560
gataaaatgc nnccagaaga gtataaaatg agnttttata aaggntatna taaaattatg   1620
gataaacgat cgcagctgag tacacgagct cacccgcgga gtcgacaaga tccaagtact   1680
acccgggnat acgtaactag tgcatgctcg cgaaatattt aggccttatc gaattaat     1738
```

<210> SEQ ID NO 13
<211> LENGTH: 628
<212> TYPE: DNA
<213> ORGANISM: Staphylococcus homini
<220> FEATURE:
<221> NAME/KEY: misc_feature
<222> LOCATION: (1)...(628)
<223> OTHER INFORMATION: n = A,T,C or G

<400> SEQUENCE: 13

```
tgtgggnctt tgttccttgn tcagctcccc aacggcttga agtactcgta cgcgccctct     60
tcctcagtcg ccgcctcgtt ggcgatgctc cacatcacga cgcttggatg gttcttgtca    120
cgagacacca gttcacggag aacgtcttga tggtgctcaa acgtccgaat cttctcccag    180
gtactgacgc gctcgctgcc ttcgccgagt cccgtggtgg ccatgaagtt gaggtgcacg    240
ccaactgccg gagtctcgtc gatcacgacc agaccctcgc gatccgcaag acgcatcaac    300
tcttcagagt acggatagtg tgcggtccgg aagctgttgg cgccgatcca tttgaggata    360
ttgaaatcca tcacattgct cgcttcgtta aagccacggc cgttgatagg agtgtcctca    420
tgtttgccaa agcccttgaa gtagaacggt ttgttgttga tgaggaactt gccgtcgttg    480
acttcacggt ccgcacgccg aacggctctt catagacatc gatggtcaag tcccgtcgtt    540
caccagttcc actttgatct ggtagagata cgtgttcaag tggttcccag aggatgacat    600
tcggaatctt cacgttaccg ctcaagcc                                       628
```

<210> SEQ ID NO 14
<211> LENGTH: 1689
<212> TYPE: DNA
<213> ORGANISM: Thermotoga maritima
<220> FEATURE:

-continued

<221> NAME/KEY: misc_feature
<222> LOCATION: (1)...(1689)
<223> OTHER INFORMATION: n = A,T,C or G

<400> SEQUENCE: 14
atggtaagac cgcaacgaaa caagaagaga tttattctta tcttgaatgg agtttggaat 60
cttgaagtaa ccagcaaaga cagaccaatc gccgttcctg gaagctggaa tgagcagtac 120
caggatctgt gctacgaaga aggacccttc acctacaaaa ccaccttcta cgttccgaag 180
naactttcac aaaaacacat cagactttac tttgctgcgg tgaacacgga ctgcgaggtc 240
ttcctcaacg gagagaaagt gggagagaat cacattgaat accttccctt cgaagtagat 300
gtgacgggga aagtgaaatc cggagagaac gaactcaggg tggttgttga gaacagattg 360
aaagtgggag gatttccctc gaaggttcca gacagcggca ctcacaccgt gggatttttt 420
ggaagttttc cacctgcaaa cttcgacttc ttcccctacg gtggaatcat aaggcctgtt 480
ctgatagagt tcacagacca cgcgaggata ctcgacatct gggtggacac gagtgagtct 540
gaaccggaga agaaacttgg aaaagtgaaa gtgaagatag aagtctcaga agaagcggtg 600
ggacaggaga tgacgatcaa acttggagag gaagagaaaa agattagaac atccaacaga 660
ttcgtcgaag gggagttcat cctcgaaaac gccaggttct ggagcctcga agatccatat 720
ctttatcctc tcaaggtgga acttgaaaaa gacgagtaca ctctggacat cggaatcaga 780
acgatcagct gggacgagaa gaggctctat ctgaacggga aacctgtctt tttgaagggc 840
tttggaaagc acgaggaatt ccccgttctg ggcagggca ccttttatcc attgatgata 900
aaagacttca accttctgaa gtggatcaac gcgaattctt tcaggacctc tcactatcct 960
tacagtgaag agtggctgga tcttgccgac agactcggaa tccttgtgat agacgaagcc 1020
ccgcacgttg gtatcacaag gtaccactac aatcccgaga ctcagaagat agcagaagac 1080
aacataagaa gaatgatcga cagacacaag aaccatccca gtgtgatcat gtggagtgtg 1140
gcgaacgaac cagagtccaa ccatccagac gcggagggtt tcttcaaagc cctttatgag 1200
actgccaatg aaatggatcg aacacgcccc gttgtcatgg tgagcatgat ggacgcacca 1260
gacgagagaa caagagacgt ggcgctgaag tacttcgaca tcgtctgtgt gaacaggtac 1320
tacggctggt acatctatca gggaaggata gaagaaggac ttcaagctct ggaaaaagac 1380
atagaagagc tctatgcaag gcacagaaag cccatctttg tcacagaatt cggtgcggac 1440
gcgatagctg gcatccacta cgatccacct caaatgttct ccgaagagta ccaagcagag 1500
ctcgttgaaa agacgatcag gctccttttg aaaaaagact acatcatcgg aacacacgtg 1560
tgggcctttg cagattttaa gactcctcag aatgtgagaa gacccattct caaccacaag 1620
ggtgttttca caagagacag acaacccaaa ctcgttgctc atgtactgag aagactgtgg 1680
agtgaggtt 1689

<210> SEQ ID NO 15
<211> LENGTH: 602
<212> TYPE: PRT
<213> ORGANISM: Bacillus sp.

<400> SEQUENCE: 15

Met Leu Tyr Pro Ile Asn Thr Glu Thr Arg Gly Val Phe Asp Leu Asn
1 5 10 15

Gly Val Trp Asn Phe Lys Leu Asp Tyr Gly Lys Gly Leu Glu Glu Lys
20 25 30

Trp Tyr Glu Ser Lys Leu Thr Asp Thr Ile Ser Met Ala Val Pro Ser

-continued

```
        35                  40                  45

Ser Tyr Asn Asp Ile Gly Val Thr Lys Glu Ile Arg Asn His Ile Gly
    50                  55                  60

Tyr Val Trp Tyr Glu Arg Glu Phe Thr Val Pro Ala Tyr Leu Lys Asp
65                  70                  75                  80

Gln Arg Ile Val Leu Arg Phe Gly Ser Ala Thr His Lys Ala Ile Val
                85                  90                  95

Tyr Val Asn Gly Glu Leu Val Val Glu His Lys Gly Gly Phe Leu Pro
            100                 105                 110

Phe Glu Ala Glu Ile Asn Asn Ser Leu Arg Asp Gly Met Asn Arg Val
        115                 120                 125

Thr Val Ala Val Asp Asn Ile Leu Asp Asp Ser Thr Leu Pro Val Gly
    130                 135                 140

Leu Tyr Ser Glu Arg His Glu Glu Gly Leu Gly Lys Val Ile Arg Asn
145                 150                 155                 160

Lys Pro Asn Phe Asp Phe Phe Asn Tyr Ala Gly Leu His Arg Pro Val
                165                 170                 175

Lys Ile Tyr Thr Thr Pro Phe Thr Tyr Val Glu Asp Ile Ser Val Val
            180                 185                 190

Thr Asp Phe Asn Gly Pro Thr Gly Thr Val Thr Tyr Thr Val Asp Phe
        195                 200                 205

Gln Gly Lys Ala Glu Thr Val Lys Val Ser Val Val Asp Glu Glu Gly
    210                 215                 220

Lys Val Val Ala Ser Thr Glu Gly Leu Ser Gly Asn Val Glu Ile Pro
225                 230                 235                 240

Asn Val Ile Leu Trp Glu Pro Leu Asn Thr Tyr Leu Tyr Gln Ile Lys
                245                 250                 255

Val Glu Leu Val Asn Asp Gly Leu Thr Ile Asp Val Tyr Glu Glu Pro
            260                 265                 270

Phe Gly Val Arg Thr Val Glu Val Asn Asp Gly Lys Phe Leu Ile Asn
        275                 280                 285

Asn Lys Pro Phe Tyr Phe Lys Gly Phe Gly Lys His Glu Asp Thr Pro
    290                 295                 300

Ile Asn Gly Arg Gly Phe Asn Glu Ala Ser Asn Val Met Asp Phe Asn
305                 310                 315                 320

Ile Leu Lys Trp Ile Gly Ala Asn Ser Phe Arg Thr Ala His Tyr Pro
                325                 330                 335

Tyr Ser Glu Glu Leu Met Arg Leu Ala Asp Arg Glu Gly Leu Val Val
            340                 345                 350

Ile Asp Glu Thr Pro Ala Val Gly Val His Leu Asn Phe Met Ala Thr
        355                 360                 365

Thr Gly Leu Gly Glu Gly Ser Glu Arg Val Ser Thr Trp Glu Lys Ile
    370                 375                 380

Arg Thr Phe Glu His His Gln Asp Val Leu Arg Glu Leu Val Ser Arg
385                 390                 395                 400

Asp Lys Asn His Pro Ser Val Val Met Trp Ser Ile Ala Asn Glu Ala
                405                 410                 415

Ala Thr Glu Glu Gly Ala Tyr Glu Tyr Phe Lys Pro Leu Val Glu
            420                 425                 430

Leu Thr Lys Glu Leu Asp Pro Gln Lys Arg Pro Val Thr Ile Val Leu
        435                 440                 445

Phe Val Met Ala Thr Pro Glu Thr Asp Lys Val Ala Glu Leu Ile Asp
    450                 455                 460
```

-continued

```
Val Ile Ala Leu Asn Arg Tyr Asn Gly Trp Tyr Phe Asp Gly Gly Asp
465                 470                 475                 480

Leu Glu Ala Ala Lys Val His Leu Arg Gln Glu Phe His Ala Trp Asn
                485                 490                 495

Lys Arg Cys Pro Gly Lys Pro Ile Met Ile Thr Glu Tyr Gly Ala Asp
            500                 505                 510

Thr Val Ala Gly Phe His Asp Ile Asp Pro Val Met Phe Thr Glu Glu
        515                 520                 525

Tyr Gln Val Glu Tyr Tyr Gln Ala Asn His Val Val Phe Asp Glu Phe
    530                 535                 540

Glu Asn Phe Val Gly Glu Gln Ala Trp Asn Phe Ala Asp Phe Ala Thr
545                 550                 555                 560

Ser Gln Gly Val Met Arg Val Gln Gly Asn Lys Lys Gly Val Phe Thr
                565                 570                 575

Arg Asp Arg Lys Pro Lys Leu Ala Ala His Val Phe Arg Glu Arg Trp
            580                 585                 590

Thr Asn Ile Pro Asp Phe Gly Tyr Lys Asn
        595                 600


<210> SEQ ID NO 16
<211> LENGTH: 613
<212> TYPE: PRT
<213> ORGANISM: Homo sapien

<400> SEQUENCE: 16

Leu Gly Leu Gln Gly Gly Met Leu Tyr Pro Gln Glu Ser Pro Ser Arg
 1               5                  10                  15

Glu Cys Lys Glu Leu Asp Gly Leu Trp Ser Phe Arg Ala Asp Phe Ser
            20                  25                  30

Asp Asn Arg Arg Arg Gly Phe Glu Glu Gln Trp Tyr Arg Arg Pro Leu
        35                  40                  45

Trp Glu Ser Gly Pro Thr Val Asp Met Pro Val Pro Ser Ser Phe Asn
    50                  55                  60

Asp Ile Ser Gln Asp Trp Arg Leu Arg His Phe Val Gly Trp Val Trp
65                  70                  75                  80

Tyr Glu Arg Glu Val Ile Leu Pro Glu Arg Trp Thr Gln Asp Leu Arg
                85                  90                  95

Thr Arg Val Val Leu Arg Ile Gly Ser Ala His Ser Tyr Ala Ile Val
            100                 105                 110

Trp Val Asn Gly Val Asp Thr Leu Glu His Glu Gly Gly Tyr Leu Pro
        115                 120                 125

Phe Glu Ala Asp Ile Ser Asn Leu Val Gln Val Gly Pro Leu Pro Ser
    130                 135                 140

Arg Leu Arg Ile Thr Ile Ala Ile Asn Asn Thr Leu Thr Pro Thr Thr
145                 150                 155                 160

Leu Pro Pro Gly Thr Ile Gln Tyr Leu Thr Asp Thr Ser Lys Tyr Pro
                165                 170                 175

Lys Gly Tyr Phe Val Gln Asn Thr Tyr Phe Asp Phe Phe Asn Tyr Ala
            180                 185                 190

Gly Leu Gln Arg Ser Val Leu Leu Tyr Thr Thr Pro Thr Thr Tyr Ile
        195                 200                 205

Asp Asp Ile Thr Val Thr Thr Ser Val Glu Gln Asp Ser Gly Leu Val
    210                 215                 220

Asn Tyr Gln Ile Ser Val Lys Gly Ser Asn Leu Phe Lys Leu Glu Val
```

-continued

```
225                 230                 235                 240

Arg Leu Leu Asp Ala Glu Asn Lys Val Val Ala Asn Gly Thr Gly Thr
                245                 250                 255

Gln Gly Gln Leu Lys Val Pro Gly Val Ser Leu Trp Trp Pro Tyr Leu
            260                 265                 270

Met His Glu Arg Pro Ala Tyr Leu Tyr Ser Leu Glu Val Gln Leu Thr
        275                 280                 285

Ala Gln Thr Ser Leu Gly Pro Val Ser Asp Phe Tyr Thr Leu Pro Val
    290                 295                 300

Gly Ile Arg Thr Val Ala Val Thr Lys Ser Gln Phe Leu Ile Asn Gly
305                 310                 315                 320

Lys Pro Phe Tyr Phe His Gly Val Asn Lys His Glu Asp Ala Asp Ile
                325                 330                 335

Arg Gly Lys Gly Phe Asp Trp Pro Leu Leu Val Lys Asp Phe Asn Leu
            340                 345                 350

Leu Arg Trp Leu Gly Ala Asn Ala Phe Arg Thr Ser His Tyr Pro Tyr
        355                 360                 365

Ala Glu Glu Val Met Gln Met Cys Asp Arg Tyr Gly Ile Val Val Ile
    370                 375                 380

Asp Glu Cys Pro Gly Val Gly Leu Ala Leu Pro Gln Phe Phe Asn Asn
385                 390                 395                 400

Val Ser Leu His His His Met Gln Val Met Glu Glu Val Val Arg Arg
                405                 410                 415

Asp Lys Asn His Pro Ala Val Val Met Trp Ser Val Ala Asn Glu Pro
            420                 425                 430

Ala Ser His Leu Glu Ser Ala Gly Tyr Tyr Leu Lys Met Val Ile Ala
        435                 440                 445

His Thr Lys Ser Leu Asp Pro Ser Arg Pro Val Thr Phe Val Ser Asn
    450                 455                 460

Ser Asn Tyr Ala Ala Asp Lys Gly Ala Pro Tyr Val Asp Val Ile Cys
465                 470                 475                 480

Leu Asn Ser Tyr Tyr Ser Trp Tyr His Asp Tyr Gly His Leu Glu Leu
                485                 490                 495

Ile Gln Leu Gln Leu Ala Thr Gln Phe Glu Asn Trp Tyr Lys Lys Tyr
            500                 505                 510

Gln Lys Pro Ile Ile Gln Ser Glu Tyr Gly Ala Glu Thr Ile Ala Gly
        515                 520                 525

Phe His Gln Asp Pro Pro Leu Met Phe Thr Glu Glu Tyr Gln Lys Ser
    530                 535                 540

Leu Leu Glu Gln Tyr His Leu Gly Leu Asp Gln Lys Arg Arg Lys Tyr
545                 550                 555                 560

Val Val Gly Glu Leu Ile Trp Asn Phe Ala Asp Phe Met Thr Glu Gln
                565                 570                 575

Ser Pro Thr Arg Val Leu Gly Asn Lys Lys Gly Ile Phe Thr Arg Gln
            580                 585                 590

Arg Gln Pro Lys Ser Ala Ala Phe Leu Leu Arg Glu Arg Tyr Trp Lys
        595                 600                 605

Ile Ala Asn Glu Thr
    610

<210> SEQ ID NO 17
<211> LENGTH: 603
<212> TYPE: PRT
<213> ORGANISM: Escherichia coli
```

-continued

<400> SEQUENCE: 17

Met Leu Arg Pro Val Glu Thr Pro Thr Arg Glu Ile Lys Lys Leu Asp
1 5 10 15

Gly Leu Trp Ala Phe Ser Leu Asp Arg Glu Asn Cys Gly Ile Asp Gln
20 25 30

Arg Trp Trp Glu Ser Ala Leu Gln Glu Ser Arg Ala Ile Ala Val Pro
35 40 45

Gly Ser Phe Asn Asp Gln Phe Ala Asp Ala Asp Ile Arg Asn Tyr Ala
50 55 60

Gly Asn Val Trp Tyr Gln Arg Glu Val Phe Ile Pro Lys Gly Trp Ala
65 70 75 80

Gly Gln Arg Ile Val Leu Arg Phe Asp Ala Val Thr His Tyr Gly Lys
85 90 95

Val Trp Val Asn Asn Gln Glu Val Met Glu His Gln Gly Gly Tyr Thr
100 105 110

Pro Phe Glu Ala Asp Val Thr Pro Tyr Val Ile Ala Gly Lys Ser Val
115 120 125

Arg Ile Thr Val Cys Val Asn Asn Glu Leu Asn Trp Gln Thr Ile Pro
130 135 140

Pro Gly Met Val Ile Thr Asp Glu Asn Gly Lys Lys Lys Gln Ser Tyr
145 150 155 160

Phe His Asp Phe Phe Asn Tyr Ala Gly Ile His Arg Ser Val Met Leu
165 170 175

Tyr Thr Thr Pro Asn Thr Trp Val Asp Asp Ile Thr Val Val Thr His
180 185 190

Val Ala Gln Asp Cys Asn His Ala Ser Val Asp Trp Gln Val Val Ala
195 200 205

Asn Gly Asp Val Ser Val Glu Leu Arg Asp Ala Asp Gln Gln Val Val
210 215 220

Ala Thr Gly Gln Gly Thr Ser Gly Thr Leu Gln Val Val Asn Pro His
225 230 235 240

Leu Trp Gln Pro Gly Glu Gly Tyr Leu Tyr Glu Leu Cys Val Thr Ala
245 250 255

Lys Ser Gln Thr Glu Cys Asp Ile Tyr Pro Leu Arg Val Gly Ile Arg
260 265 270

Ser Val Ala Val Lys Gly Glu Gln Phe Leu Ile Asn His Lys Pro Phe
275 280 285

Tyr Phe Thr Gly Phe Gly Arg His Glu Asp Ala Asp Leu Arg Gly Lys
290 295 300

Gly Phe Asp Asn Val Leu Met Val His Asp His Ala Leu Met Asp Trp
305 310 315 320

Ile Gly Ala Asn Ser Tyr Arg Thr Ser His Tyr Pro Tyr Ala Glu Glu
325 330 335

Met Leu Asp Trp Ala Asp Glu His Gly Ile Val Val Ile Asp Glu Thr
340 345 350

Ala Ala Val Gly Phe Asn Leu Ser Leu Gly Ile Gly Phe Glu Ala Gly
355 360 365

Asn Lys Pro Lys Glu Leu Tyr Ser Glu Glu Ala Val Asn Gly Glu Thr
370 375 380

Gln Gln Ala His Leu Gln Ala Ile Lys Glu Leu Ile Ala Arg Asp Lys
385 390 395 400

Asn His Pro Ser Val Val Met Trp Ser Ile Ala Asn Glu Pro Asp Thr

-continued

```
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600


<210> SEQ ID NO 18
<211> LENGTH: 607
<212> TYPE: PRT
<213> ORGANISM: Bacillus sp.

<400> SEQUENCE: 18

Met Val Asp Leu Thr Ser Leu Tyr Pro Ile Asn Thr Glu Thr Arg Gly
 1               5                  10                  15

Val Phe Asp Leu Asn Gly Val Trp Asn Phe Lys Leu Asp Tyr Gly Lys
            20                  25                  30

Gly Leu Glu Glu Lys Trp Tyr Glu Ser Lys Leu Thr Asp Thr Ile Ser
        35                  40                  45

Met Ala Val Pro Ser Ser Tyr Asn Asp Ile Gly Val Thr Lys Glu Ile
    50                  55                  60

Arg Asn His Ile Gly Tyr Val Trp Tyr Glu Arg Glu Phe Thr Val Pro
65                  70                  75                  80

Ala Tyr Leu Lys Asp Gln Arg Ile Val Leu Arg Phe Gly Ser Ala Thr
                85                  90                  95

His Lys Ala Ile Val Tyr Val Asn Gly Glu Leu Val Val Glu His Lys
            100                 105                 110

Gly Gly Phe Leu Pro Phe Glu Ala Glu Ile Asn Asn Ser Leu Arg Asp
        115                 120                 125

Gly Met Asn Arg Val Thr Val Ala Val Asp Asn Ile Leu Asp Asp Ser
    130                 135                 140

Thr Leu Pro Val Gly Leu Tyr Ser Glu Arg His Glu Glu Gly Leu Gly
145                 150                 155                 160

Lys Val Ile Arg Asn Lys Pro Asn Phe Asp Phe Phe Asn Tyr Ala Gly
                165                 170                 175
```

-continued

```
Leu His Arg Pro Val Lys Ile Tyr Thr Thr Pro Phe Thr Tyr Val Glu
            180                 185                 190

Asp Ile Ser Val Val Thr Asp Phe Asn Gly Pro Thr Gly Thr Val Thr
        195                 200                 205

Tyr Thr Val Asp Phe Gln Gly Lys Ala Glu Thr Val Lys Val Ser Val
    210                 215                 220

Val Asp Glu Glu Gly Lys Val Val Ala Ser Thr Glu Gly Leu Ser Gly
225                 230                 235                 240

Asn Val Glu Ile Pro Asn Val Ile Leu Trp Glu Pro Leu Asn Thr Tyr
                245                 250                 255

Leu Tyr Gln Ile Lys Val Glu Leu Val Asn Asp Gly Leu Thr Ile Asp
            260                 265                 270

Val Tyr Glu Glu Pro Phe Gly Val Arg Thr Val Glu Val Asn Asp Gly
        275                 280                 285

Lys Phe Leu Ile Asn Asn Lys Pro Phe Tyr Phe Lys Gly Phe Gly Lys
    290                 295                 300

His Glu Asp Thr Pro Ile Asn Gly Arg Gly Phe Asn Glu Ala Ser Asn
305                 310                 315                 320

Val Met Asp Phe Asn Ile Leu Lys Trp Ile Gly Ala Asn Ser Phe Arg
                325                 330                 335

Thr Ala His Tyr Pro Tyr Ser Glu Glu Leu Met Arg Leu Ala Asp Arg
            340                 345                 350

Glu Gly Leu Val Val Ile Asp Glu Thr Pro Ala Val Gly Val His Leu
        355                 360                 365

Asn Phe Met Ala Thr Thr Gly Leu Gly Glu Gly Ser Glu Arg Val Ser
    370                 375                 380

Thr Trp Glu Lys Ile Arg Thr Phe Glu His His Gln Asp Val Leu Arg
385                 390                 395                 400

Glu Leu Val Ser Arg Asp Lys Asn His Pro Ser Val Val Met Trp Ser
                405                 410                 415

Ile Ala Asn Glu Ala Ala Thr Glu Glu Glu Gly Ala Tyr Glu Tyr Phe
            420                 425                 430

Lys Pro Leu Val Glu Leu Thr Lys Glu Leu Asp Pro Gln Lys Arg Pro
        435                 440                 445

Val Thr Ile Val Leu Phe Val Met Ala Thr Pro Glu Thr Asp Lys Val
    450                 455                 460

Ala Glu Leu Ile Asp Val Ile Ala Leu Asn Arg Tyr Asn Gly Trp Tyr
465                 470                 475                 480

Phe Asp Gly Gly Asp Leu Glu Ala Ala Lys Val His Leu Arg Gln Glu
                485                 490                 495

Phe His Ala Trp Asn Lys Arg Cys Pro Gly Lys Pro Ile Met Ile Thr
            500                 505                 510

Glu Tyr Gly Ala Asp Thr Val Ala Gly Phe His Asp Ile Asp Pro Val
        515                 520                 525

Met Phe Thr Glu Glu Tyr Gln Val Glu Tyr Tyr Gln Ala Asn His Val
    530                 535                 540

Val Phe Asp Glu Phe Glu Asn Phe Val Gly Glu Gln Ala Trp Asn Phe
545                 550                 555                 560

Ala Asp Phe Ala Thr Ser Gln Gly Val Met Arg Val Gln Gly Asn Lys
                565                 570                 575

Lys Gly Val Phe Thr Arg Asp Arg Lys Pro Lys Leu Ala Ala His Val
            580                 585                 590

Phe Arg Glu Arg Trp Thr Asn Ile Pro Asp Phe Gly Tyr Lys Asn
```

-continued

```
        595                 600                 605


<210> SEQ ID NO 19
<211> LENGTH: 376
<212> TYPE: PRT
<213> ORGANISM: Staphylococcus homini
<220> FEATURE:
<221> NAME/KEY: VARIANT
<222> LOCATION: (1)...(376)
<223> OTHER INFORMATION: Xaa = Any Amino Acid

<400> SEQUENCE: 19

Gly Leu Ser Gly Asn Val Glu Ile Pro Asn Val Ile Leu Trp Glu Pro
 1               5                  10                  15

Leu Asn Thr Tyr Leu Tyr Gln Ile Lys Val Glu Leu Val Asn Asp Gly
            20                  25                  30

Leu Thr Ile Asp Val Tyr Glu Glu Pro Phe Gly Val Arg Thr Val Glu
        35                  40                  45

Val Asn Asp Gly Lys Phe Leu Ile Asn Asn Lys Pro Phe Tyr Phe Lys
    50                  55                  60

Gly Phe Gly Lys His Glu Asp Thr Pro Ile Asn Gly Arg Gly Phe Asn
65                  70                  75                  80

Glu Ala Ser Asn Val Met Asp Phe Asn Ile Leu Lys Trp Ile Gly Ala
                85                  90                  95

Asn Ser Phe Arg Thr Ala His Tyr Pro Tyr Ser Glu Glu Leu Met Arg
            100                 105                 110

Leu Ala Asp Arg Glu Gly Leu Val Val Ile Asp Glu Thr Pro Ala Val
        115                 120                 125

Gly Val His Leu Asn Phe Met Ala Thr Thr Gly Leu Gly Glu Gly Ser
    130                 135                 140

Glu Arg Val Ser Thr Trp Glu Lys Ile Arg Thr Phe Glu His His Gln
145                 150                 155                 160

Asp Val Leu Arg Glu Leu Val Ser Arg Asp Lys Asn His Pro Ser Val
                165                 170                 175

Val Met Trp Ser Ile Ala Asn Glu Ala Ala Thr Glu Glu Glu Gly Ala
            180                 185                 190

Tyr Glu Tyr Phe Lys Pro Leu Gly Gly Ala Ala Lys Glu Leu Asp Pro
        195                 200                 205

Xaa Lys Arg Pro Val Thr Ile Val Leu Phe Val Met Ala Thr Pro Glu
    210                 215                 220

Thr Asp Lys Val Ala Glu Leu Ile Asp Val Ile Ala Leu Asn Arg Tyr
225                 230                 235                 240

Asn Gly Trp Tyr Phe Asp Gly Gly Asp Leu Glu Ala Ala Lys Val His
                245                 250                 255

Leu Arg Gln Glu Phe His Ala Trp Asn Lys Arg Cys Pro Gly Lys Pro
            260                 265                 270

Ile Met Ile Thr Glu Tyr Gly Ala Asp Thr Val Ala Gly Phe His Asp
        275                 280                 285

Ile Asp Pro Val Met Phe Thr Glu Glu Tyr Gln Val Glu Tyr Tyr Gln
    290                 295                 300

Ala Asn His Val Val Phe Asp Glu Phe Glu Asn Phe Val Gly Glu Gln
305                 310                 315                 320

Ala Trp Asn Phe Ala Asp Phe Ala Thr Ser Gln Gly Val Met Arg Val
                325                 330                 335

Gln Gly Asn Lys Lys Gly Val Phe Thr Arg Asp Arg Lys Pro Xaa Leu
            340                 345                 350
```

```
Ala Ala His Val Phe Arg Glu Arg Arg Thr Asn Ile Pro Asp Phe Gly
        355                 360                 365

Tyr Lys Asn Ala Ser His His His
    370                 375


<210> SEQ ID NO 20
<211> LENGTH: 535
<212> TYPE: PRT
<213> ORGANISM: Staphylococcus warneri
<220> FEATURE:
<221> NAME/KEY: VARIANT
<222> LOCATION: (1)...(535)
<223> OTHER INFORMATION: Xaa = Any Amino Acid

<400> SEQUENCE: 20

Leu Xaa Leu Leu His Pro Ile Thr Thr Gly Thr Arg Gly Gly Phe Ala
 1               5                  10                  15

Leu Tyr Gly Xaa Xaa Asn Leu Met Leu Asp Tyr Gly Xaa Gly Leu Thr
            20                  25                  30

Asp Thr Trp Thr Xaa Ser Leu Leu Thr Glu Leu Ser Arg Leu Val Val
        35                  40                  45

Leu Ser Trp Thr Thr His Xaa Leu Thr Gly Glu Xaa Pro Ala Ile Ser
    50                  55                  60

Ile Leu Trp Pro Asn Ser Glu Leu Thr Val Ser Xaa Leu Tyr Xaa Gly
65                  70                  75                  80

Ser Leu Xaa Ser Ser Ser Xaa Leu Cys Ser Ser Leu Thr Xaa His Val
                85                  90                  95

Val Ile Cys Gln Xaa Val Thr Leu Xaa Val Asp His Thr Gly Leu Ile
            100                 105                 110

Xaa Xaa Phe Glu Phe Met Ser Thr Thr Cys Cys Xaa Xaa Asp Glu Leu
        115                 120                 125

Val Thr Gly Thr Leu Ala Xaa Ile Leu Tyr His Xaa Ile Leu Pro His
    130                 135                 140

Gly Leu Tyr Arg Lys Arg His Glu Xaa Gly Leu Gly Lys Xaa Asn Phe
145                 150                 155                 160

Tyr Xaa Leu His Phe Ala Phe Phe Xaa Tyr Ala Xaa Leu Xaa Arg Thr
                165                 170                 175

Val Xaa Met Tyr Xaa Asn Leu Val Arg Xaa Gln Asp Ile Val Val Thr
            180                 185                 190

Xaa His Xaa Xaa Xaa Thr Val Glu Gln Cys Val Xaa Xaa Asn Lys Ile
        195                 200                 205

Xaa Ser Val Lys Ile Thr Ile Leu Asp Glu Asn Asp His Ala Ile Xaa
    210                 215                 220

Glu Ser Glu Gly Ala Lys Gly Asn Val Thr Ile Gln Asn Pro Ile Leu
225                 230                 235                 240

Trp Gln Pro Leu His Ala Tyr Leu Tyr Asn Met Lys Val Glu Leu Leu
                245                 250                 255

Asn Asp Asn Glu Cys Val Asp Val Tyr Thr Glu Arg Phe Gly Ile Arg
            260                 265                 270

Ser Val Glu Val Lys Asp Gly Gln Phe Leu Ile Asn Asp Lys Pro Phe
        275                 280                 285

Tyr Phe Lys Gly Phe Gly Lys His Glu Asp Thr Tyr Asn Gly Arg Gly
    290                 295                 300

Leu Asn Glu Ser Ala Asn Val Met Asp Ile Asn Leu Met Lys Trp Ile
305                 310                 315                 320
```

-continued

```
Gly Ala Asn Ser Phe Arg Thr Ser His Tyr Pro Tyr Ser Glu Glu Met
                325                 330                 335

Met Arg Leu Ala Asp Glu Gln Gly Ile Val Val Ile Asp Glu Thr Thr
            340                 345                 350

Xaa Val Gly Ile His Leu Asn Phe Met Xaa Thr Leu Gly Gly Ser Xaa
        355                 360                 365

Ala His Asp Thr Trp Xaa Glu Phe Asp Thr Leu Glu Phe His Lys Glu
    370                 375                 380

Val Ile Xaa Asp Leu Ile Xaa Arg Asp Lys Asn His Ala Trp Val Val
385                 390                 395                 400

Met Trp Xaa Phe Gly Asn Glu Xaa Gly Xaa Asn Lys Gly Gly Ala Lys
                405                 410                 415

Ala Xaa Phe Glu Pro Phe Val Asn Leu Ala Gly Glu Lys Asp Xaa Xaa
            420                 425                 430

Xaa Xaa Pro Val Thr Ile Val Thr Ile Leu Xaa Ala Xaa Arg Asn Val
        435                 440                 445

Cys Glu Val Xaa Asp Leu Val Asp Val Val Cys Leu Xaa Xaa Xaa Xaa
    450                 455                 460

Gly Trp Tyr Xaa Gln Ser Gly Asp Leu Glu Gly Ala Lys Xaa Ala Leu
465                 470                 475                 480

Asp Lys Glu Xaa Xaa Glu Trp Trp Lys Xaa Gln Xaa Asn Lys Pro Xaa
                485                 490                 495

Met Phe Thr Glu Tyr Gly Val Asp Xaa Val Val Gly Leu Xaa Xaa Xaa
            500                 505                 510

Pro Asp Lys Met Xaa Pro Glu Glu Tyr Lys Met Xaa Phe Tyr Lys Gly
        515                 520                 525

Tyr Xaa Lys Ile Met Asp Lys
    530                 535


<210> SEQ ID NO 21
<211> LENGTH: 563
<212> TYPE: PRT
<213> ORGANISM: Thermotoga maritima
<220> FEATURE:
<221> NAME/KEY: VARIANT
<222> LOCATION: (1)...(563)
<223> OTHER INFORMATION: Xaa = Any Amino Acid

<400> SEQUENCE: 21

Met Val Arg Pro Gln Arg Asn Lys Lys Arg Phe Ile Leu Ile Leu Asn
 1               5                  10                  15

Gly Val Trp Asn Leu Glu Val Thr Ser Lys Asp Arg Pro Ile Ala Val
            20                  25                  30

Pro Gly Ser Trp Asn Glu Gln Tyr Gln Asp Leu Cys Tyr Glu Glu Gly
        35                  40                  45

Pro Phe Thr Tyr Lys Thr Thr Phe Tyr Val Pro Lys Xaa Leu Ser Gln
    50                  55                  60

Lys His Ile Arg Leu Tyr Phe Ala Ala Val Asn Thr Asp Cys Glu Val
65                  70                  75                  80

Phe Leu Asn Gly Glu Lys Val Gly Glu Asn His Ile Glu Tyr Leu Pro
                85                  90                  95

Phe Glu Val Asp Val Thr Gly Lys Val Lys Ser Gly Glu Asn Glu Leu
            100                 105                 110

Arg Val Val Val Glu Asn Arg Leu Lys Val Gly Gly Phe Pro Ser Lys
        115                 120                 125

Val Pro Asp Ser Gly Thr His Thr Val Gly Phe Phe Gly Ser Phe Pro
```

-continued

```
    130                 135                 140

Pro Ala Asn Phe Asp Phe Phe Pro Tyr Gly Gly Ile Ile Arg Pro Val
145                 150                 155                 160

Leu Ile Glu Phe Thr Asp His Ala Arg Ile Leu Asp Ile Trp Val Asp
                165                 170                 175

Thr Ser Glu Ser Glu Pro Glu Lys Lys Leu Gly Lys Val Lys Val Lys
            180                 185                 190

Ile Glu Val Ser Glu Glu Ala Val Gly Gln Glu Met Thr Ile Lys Leu
        195                 200                 205

Gly Glu Glu Glu Lys Lys Ile Arg Thr Ser Asn Arg Phe Val Glu Gly
    210                 215                 220

Glu Phe Ile Leu Glu Asn Ala Arg Phe Trp Ser Leu Glu Asp Pro Tyr
225                 230                 235                 240

Leu Tyr Pro Leu Lys Val Glu Leu Glu Lys Asp Glu Tyr Thr Leu Asp
                245                 250                 255

Ile Gly Ile Arg Thr Ile Ser Trp Asp Glu Lys Arg Leu Tyr Leu Asn
            260                 265                 270

Gly Lys Pro Val Phe Leu Lys Gly Phe Gly Lys His Glu Glu Phe Pro
        275                 280                 285

Val Leu Gly Gln Gly Thr Phe Tyr Pro Leu Met Ile Lys Asp Phe Asn
    290                 295                 300

Leu Leu Lys Trp Ile Asn Ala Asn Ser Phe Arg Thr Ser His Tyr Pro
305                 310                 315                 320

Tyr Ser Glu Glu Trp Leu Asp Leu Ala Asp Arg Leu Gly Ile Leu Val
                325                 330                 335

Ile Asp Glu Ala Pro His Val Gly Ile Thr Arg Tyr His Tyr Asn Pro
            340                 345                 350

Glu Thr Gln Lys Ile Ala Glu Asp Asn Ile Arg Arg Met Ile Asp Arg
        355                 360                 365

His Lys Asn His Pro Ser Val Ile Met Trp Ser Val Ala Asn Glu Pro
    370                 375                 380

Glu Ser Asn His Pro Asp Ala Glu Gly Phe Phe Lys Ala Leu Tyr Glu
385                 390                 395                 400

Thr Ala Asn Glu Met Asp Arg Thr Arg Pro Val Val Met Val Ser Met
                405                 410                 415

Met Asp Ala Pro Asp Glu Arg Thr Arg Asp Val Ala Leu Lys Tyr Phe
            420                 425                 430

Asp Ile Val Cys Val Asn Arg Tyr Tyr Gly Trp Tyr Ile Tyr Gln Gly
        435                 440                 445

Arg Ile Glu Glu Gly Leu Gln Ala Leu Glu Lys Asp Ile Glu Glu Leu
    450                 455                 460

Tyr Ala Arg His Arg Lys Pro Ile Phe Val Thr Glu Phe Gly Ala Asp
465                 470                 475                 480

Ala Ile Ala Gly Ile His Tyr Asp Pro Pro Gln Met Phe Ser Glu Glu
                485                 490                 495

Tyr Gln Ala Glu Leu Val Glu Lys Thr Ile Arg Leu Leu Leu Lys Lys
            500                 505                 510

Asp Tyr Ile Ile Gly Thr His Val Trp Ala Phe Ala Asp Phe Lys Thr
        515                 520                 525

Pro Gln Asn Val Arg Arg Pro Ile Leu Asn His Lys Gly Val Phe Thr
    530                 535                 540

Arg Asp Arg Gln Pro Lys Leu Val Ala His Val Leu Arg Arg Leu Trp
545                 550                 555                 560
```

-continued

```
Ser Glu Val

<210> SEQ ID NO 22
<211> LENGTH: 372
<212> TYPE: PRT
<213> ORGANISM: Enterobacter sp. / Salmonella sp.
<220> FEATURE:
<221> NAME/KEY: VARIANT
<222> LOCATION: (1)...(372)
<223> OTHER INFORMATION: Xaa = Any Amino Acid

<400> SEQUENCE: 22

Gly Lys Leu Ser Pro Thr Pro Thr Ala Tyr Ile Gln Asp Val Thr Val
 1               5                  10                  15

Xaa Thr Asp Val Leu Glu Asn Thr Glu Gln Ala Thr Val Leu Gly Asn
            20                  25                  30

Val Gly Ala Asp Gly Asp Ile Arg Val Glu Leu Arg Asp Gly Gln Gln
        35                  40                  45

Gln Ile Val Ala Gln Gly Leu Gly Ala Thr Gly Ile Phe Glu Leu Asp
    50                  55                  60

Asn Pro His Leu Trp Glu Pro Gly Glu Gly Tyr Leu Tyr Glu Leu Arg
65                  70                  75                  80

Val Thr Cys Glu Ala Asn Gly Glu Cys Asp Glu Tyr Pro Val Arg Val
                85                  90                  95

Gly Ile Arg Ser Ile Thr Xaa Lys Gly Glu Gln Phe Leu Ile Asn His
            100                 105                 110

Lys Pro Phe Tyr Leu Thr Gly Phe Gly Arg His Glu Asp Ala Asp Phe
        115                 120                 125

Arg Gly Lys Gly Phe Asp Pro Val Leu Met Val His Asp His Ala Leu
    130                 135                 140

Met Asn Trp Ile Gly Ala Asn Ser Tyr Arg Thr Ser His Tyr Pro Tyr
145                 150                 155                 160

Ala Glu Lys Met Leu Asp Trp Ala Asp Glu His Val Ile Val Val Ile
                165                 170                 175

Asn Glu Thr Ala Ala Gly Gly Phe Asn Thr Leu Ser Leu Gly Ile Thr
            180                 185                 190

Phe Asp Ala Gly Glu Arg Pro Lys Glu Leu Tyr Ser Glu Glu Ala Ile
        195                 200                 205

Asn Gly Glu Thr Ser Gln Gln Ala His Leu Gln Ala Ile Lys Glu Leu
    210                 215                 220

Ile Ala Arg Asp Lys Asn His Pro Ser Val Val Cys Trp Ser Ile Ala
225                 230                 235                 240

Asn Glu Pro Asp Thr Arg Pro Asn Gly Ala Arg Glu Tyr Phe Ala Pro
                245                 250                 255

Leu Ala Lys Ala Thr Arg Glu Leu Asp Pro Thr Arg Pro Ile Thr Cys
            260                 265                 270

Val Asn Val Met Phe Cys Asp Ala Glu Ser Asp Thr Ile Thr Asp Leu
        275                 280                 285

Phe Asp Val Val Cys Leu Asn Arg Tyr Tyr Gly Trp Tyr Val Gln Ser
    290                 295                 300

Gly Asp Leu Glu Lys Ala Glu Gln Met Leu Glu Gln Glu Leu Leu Ala
305                 310                 315                 320

Trp Gln Ser Lys Leu His Arg Pro Ile Ile Ile Thr Glu Tyr Gly Val
                325                 330                 335

Asp Thr Leu Ala Gly Met Pro Ser Val Tyr Pro Asp Met Trp Ser Glu
```

-continued

```
            340                 345                 350

Lys Tyr Gln Trp Lys Trp Leu Glu Met Tyr His Arg Val Phe Asp Arg
        355                 360                 365

Gly Ser Val Cys
    370


<210> SEQ ID NO 23
<211> LENGTH: 603
<212> TYPE: PRT
<213> ORGANISM: Escherichia coli

<400> SEQUENCE: 23

Met Leu Arg Pro Val Glu Thr Pro Thr Arg Glu Ile Lys Lys Leu Asp
 1               5                  10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335
```

-continued

```
Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600
```

<210> SEQ ID NO 24
<211> LENGTH: 807
<212> TYPE: DNA
<213> ORGANISM: Bacillus sp.

<400> SEQUENCE: 24

```
atggtagatc tgactagtct gtacccgatc aacaccgaga cccgtggcgt cttcgacctc      60

aatggcgtct ggaacttcaa gctggactac gggaaaggac tggaagagaa gtggtacgaa     120

agcaagctga ccgacactat tagtatggcc gtcccaagca gttacaatga cattggcgtg     180

accaaggaaa tccgcaacca tatcggatat gtctggtacg aacgtgagtt cacggtgccg     240

gcctatctga aggatcagcg tatcgtgctc cgcttcggct ctgcaactca caaagcaatt     300

gtctatgtca atggtgagct ggtcgtggag cacaagggcg gattcctgcc attcgaagcg     360

gaaatcaaca actcgctgcg tgatggcatg aatcgcgtca ccgtcgccgt ggacaacatc     420

ctcgacgata gcaccctccc ggtggggctg tacagcgagc gccacgaaga gggcctcgga     480

aaagtcattc gtaacaagcc gaacttcgac ttcttcaact atgcaggcct gcaccgtccg     540

gtgaaaatct acacgacccc gtttacgtac gtcgaggaca tctcggttgt gaccgacttc     600
```

-continued

```
aatggcccaa ccgggactgt gacctatacg gtggactttc aaggcaaagc cgagaccgtg    660

aaagtgtcgg tcgtggatga ggaaggcaaa gtggtcgcaa gcaccgaggg cctgagcggt    720

aacgtggaga ttccgaatgt catcctctgg gaaccactga acacgtatct ctaccagatc    780

aaagtggaac tggtgaacga cggactg                                        807
```

```
<210> SEQ ID NO 25
<211> LENGTH: 779
<212> TYPE: DNA
<213> ORGANISM: Salmonella sp.
<220> FEATURE:
<221> NAME/KEY: misc_feature
<222> LOCATION: (1)...(779)
<223> OTHER INFORMATION: n = A,T,C or G

<400> SEQUENCE: 25

ccncccnttt tngtancntn tttgnnanct gctgcannng atcacnacnn gganncgggg     60

ngggttcgnn ctctatggcn cgnggaacnn natgntggnc nacngttnan gactgacaga    120

cacgtggagc taaagcttgc tgccgaacta tcactcagnt cntgnaagtt ggacaacaca    180

ttncctgaca ngngaaaagc ccgccatatc catactgtgc tggcccaaca ntgagttcac    240

ngtcgtcgna ctntatgang gatcacctgt atcganctcc nttnatnttc tncagctaac    300

ataactgtgn gcatatgtca atgnatgacc tggtcggtgn ancacaccgg gcgtnattgn    360

tgnnattcga atttnatgtc aacaactttg ntgcangntg gaatgaatct gggggccagg    420

gactttggcc ancttcctna accattcgca ncctccccca gtgggcttgt acacnattgn    480

gccccaaaaa ggcntcagat aggcattttg acaagctcca nnttaacttt ttcaactatg    540

cngncctgca ccggacgctg aaaaangtac anganccttg tacgttccac caaganattt    600

aaggtgtgac ccacntccat tttcctaacn ggactgtgac tnataaaggn tgaccnttca    660

nggacacatt gcaatgaccc tttnaaacgg aanaaccccc ggnttaaagg aaaaacaaat    720

ttggttgggn agtccancca agggccaatt anttgttncn cgggggganta aancccccn    779
```

```
<210> SEQ ID NO 26
<211> LENGTH: 644
<212> TYPE: DNA
<213> ORGANISM: Pseudomonas sp.
<220> FEATURE:
<221> NAME/KEY: misc_feature
<222> LOCATION: (1)...(644)
<223> OTHER INFORMATION: n = A,T,C or G

<400> SEQUENCE: 26

tgctggacna cngttnagga tttttagaca cgnggagcta aagcttgctg accnaactat     60

cacgccggnc gtgcangctt ggaccgcgac attncctgac angngaaana ctccgccata    120

tccatctttg ctggcccaac agtgagttna cngtnncgna cnntnngang gatcagtgna    180

tcgagctccn ttnannttct ncgctaacat aacatgtngc atatgtcaat naatnacgct    240

ggncgtggan cncaccgggc tnattcgntg nnattcgaat tgnatgncaa caactntgnt    300

gcacgntggn aaanaattgc gtnacaggga ctttggccnc ttcctaaacc atngcatcct    360

cccnatgggc tgtacacgaa tgngccccca aaanggcntt cagaaaggca atttntaaca    420

aggcngannt ttgacttttt caactatgca gnnctgcacc ggacgctgaa aatgtacang    480

accctgggta cgtncnacca agacatnnaa gtngtgaccg actccattgt nctaaccggg    540

actgtaccta taatgcggac tatcanggca atgcatgacg tngaancgac acaccaggat    600

naggaaaaca antggtggna ncncaccang ccatgattgt cacg                     644
```

-continued

<210> SEQ ID NO 27
<211> LENGTH: 1888
<212> TYPE: DNA
<213> ORGANISM: Bacillus sp.

<400> SEQUENCE: 27

```
atacgactca ctagtgggtc gacccatggt agatctgact agtctgtacc cgatcaacac     60
cgagacccgt ggcgtcttcg acctcaatgg cgtctggaac ttcaagctgg actacgggaa    120
aggactggaa gagaagtggt acgaaagcaa gctgaccgac actattagta tggccgtccc    180
aagcagttac aatgacattg gcgtgaccaa ggaaatccgc aaccatatcg gatatgtctg    240
gtacgaacgt gagttcacgg tgccggccta tctgaaggat cagcgtatcg tgctccgctt    300
cggctctgca actcacaaag caattgtcta tgtcaatggt gagctggtcg tggagcacaa    360
gggcggattc ctgccattcg aagcggaaat caacaactcg ctgcgtgatg gcatgaatcg    420
cgtcaccgtc gccgtggaca acatcctcga cgatagcacc ctcccggtgg ggctgtacag    480
cgagcgccac gaagagggcc tcggaaaagt cattcgtaac aagccgaact tcgacttctt    540
caactatgca ggcctgcacc gtccggtgaa aatctacacg accccgttta cgtacgtcga    600
ggacatctcg gttgtgaccg acttcaatgg cccaaccggg actgtgacct atacggtgga    660
ctttcaaggc aaagccgaga ccgtgaaagt gtcggtcgtg gatgaggaag gcaaagtggt    720
cgcaagcacc gagggcctga gcggtaacgt ggagattccg aatgtcatcc tctgggaacc    780
actgaacacg tatctctacc cagatcaaag tggaactggt gaacgacgga ctgaccatcg    840
atgtctatga agagccgttc ggcgtgcgga ccgtggaagt caacgacggc aagttcctca    900
tcaacaacaa accgttctac ttcaagggct ttggcaaaca tgaggacact cctatcaacg    960
gccgtggctt taacgaagcg agcaatgtga tggatttcaa tatcctcaaa tggatcggcg   1020
ccaacagctt ccggaccgca cactatccgt actctgaaga gttgatgcgt cttgcggatc   1080
gcgagggtct ggtcgtgatc gacgagactc cggcagttgg cgtgcacctc aacttcatgg   1140
ccaccacggg actcggcgaa ggcagcgagc gcgtcagtac ctgggagaag attcggacgt   1200
ttgagcacca tcaagacgtt ctccgtgaac tggtgtctcg tgacaagaac catccaagcg   1260
tcgtgatgtg gagcatcgcc aacgaggcgg cgactgagga agagggcgcg tacgagtact   1320
tcaagccgtt ggtggagctg accaaggaac tcgacccaca gaagcgtccg gtcacgatcg   1380
tgctgtttgt gatggctacc ccggagacgg acaaagtcgc cgaactgatt gacgtcatcg   1440
cgctcaatcg ctataacgga tggtacttcg atggcggtga tctcgaagcg gccaaagtcc   1500
atctccgcca ggaatttcac gcgtggaaca agcgttgccc aggaaagccg atcatgatca   1560
ctgagtacgg cgcagacacc gttgcgggct ttcacgacat tgatccagtg atgttcaccg   1620
aggaatatca agtcgagtac taccaggcga accacgtcgt gttcgatgag tttgagaact   1680
tcgtgggtga gcaagcgtgg aacttcgcgg acttcgcgac ctctcagggc gtgatgcgcg   1740
tccaaggaaa caagaagggc gtgttcactc gtgaccgcaa gccgaagctc gccgcgcacg   1800
tctttcgcga gcgctggacc aacattccag atttcggcta caagaacgct agccatcacc   1860
atcaccatca cgtgtgaatt ggtgaccg                                      1888
```

<210> SEQ ID NO 28
<211> LENGTH: 615
<212> TYPE: PRT
<213> ORGANISM: Bacillus sp.

-continued

<400> SEQUENCE: 28

```
Met Val Asp Leu Thr Ser Leu Tyr Pro Ile Asn Thr Glu Thr Arg Gly
 1               5                  10                  15

Val Phe Asp Leu Asn Gly Val Trp Asn Phe Lys Leu Asp Tyr Gly Lys
            20                  25                  30

Gly Leu Glu Glu Lys Trp Tyr Glu Ser Lys Leu Thr Asp Thr Ile Ser
        35                  40                  45

Met Ala Val Pro Ser Ser Tyr Asn Asp Ile Gly Val Thr Lys Glu Ile
    50                  55                  60

Arg Asn His Ile Gly Tyr Val Trp Tyr Glu Arg Glu Phe Thr Val Pro
65                  70                  75                  80

Ala Tyr Leu Lys Asp Gln Arg Ile Val Leu Arg Phe Gly Ser Ala Thr
                85                  90                  95

His Lys Ala Ile Val Tyr Val Asn Gly Glu Leu Val Val Glu His Lys
            100                 105                 110

Gly Gly Phe Leu Pro Phe Glu Ala Glu Ile Asn Asn Ser Leu Arg Asp
        115                 120                 125

Gly Met Asn Arg Val Thr Val Ala Val Asp Asn Ile Leu Asp Asp Ser
    130                 135                 140

Thr Leu Pro Val Gly Leu Tyr Ser Glu Arg His Glu Glu Gly Leu Gly
145                 150                 155                 160

Lys Val Ile Arg Asn Lys Pro Asn Phe Asp Phe Phe Asn Tyr Ala Gly
                165                 170                 175

Leu His Arg Pro Val Lys Ile Tyr Thr Thr Pro Phe Thr Tyr Val Glu
            180                 185                 190

Asp Ile Ser Val Val Thr Asp Phe Asn Gly Pro Thr Gly Thr Val Thr
        195                 200                 205

Tyr Thr Val Asp Phe Gln Gly Lys Ala Glu Thr Val Lys Val Ser Val
    210                 215                 220

Val Asp Glu Glu Gly Lys Val Val Ala Ser Thr Glu Gly Leu Ser Gly
225                 230                 235                 240

Asn Val Glu Ile Pro Asn Val Ile Leu Trp Glu Pro Leu Asn Thr Tyr
                245                 250                 255

Leu Tyr Gln Ile Lys Val Glu Leu Val Asn Asp Gly Leu Thr Ile Asp
            260                 265                 270

Val Tyr Glu Glu Pro Phe Gly Val Arg Thr Val Glu Val Asn Asp Gly
        275                 280                 285

Lys Phe Leu Ile Asn Asn Lys Pro Phe Tyr Phe Lys Gly Phe Gly Lys
    290                 295                 300

His Glu Asp Thr Pro Ile Asn Gly Arg Gly Phe Asn Glu Ala Ser Asn
305                 310                 315                 320

Val Met Asp Phe Asn Ile Leu Lys Trp Ile Gly Ala Asn Ser Phe Arg
                325                 330                 335

Thr Ala His Tyr Pro Tyr Ser Glu Glu Leu Met Arg Leu Ala Asp Arg
            340                 345                 350

Glu Gly Leu Val Val Ile Asp Glu Thr Pro Ala Val Gly Val His Leu
        355                 360                 365

Asn Phe Met Ala Thr Thr Gly Leu Gly Glu Gly Ser Glu Arg Val Ser
    370                 375                 380

Thr Trp Glu Lys Ile Arg Thr Phe Glu His His Gln Asp Val Leu Arg
385                 390                 395                 400

Glu Leu Val Ser Arg Asp Lys Asn His Pro Ser Val Val Met Trp Ser
                405                 410                 415
```

-continued

```
Ile Ala Asn Glu Ala Ala Thr Glu Glu Glu Gly Ala Tyr Glu Tyr Phe
            420                 425                 430

Lys Pro Leu Val Glu Leu Thr Lys Glu Leu Asp Pro Gln Lys Arg Pro
        435                 440                 445

Val Thr Ile Val Leu Phe Val Met Ala Thr Pro Glu Thr Asp Lys Val
    450                 455                 460

Ala Glu Leu Ile Asp Val Ile Ala Leu Asn Arg Tyr Asn Gly Trp Tyr
465                 470                 475                 480

Phe Asp Gly Gly Asp Leu Glu Ala Ala Lys Val His Leu Arg Gln Glu
                485                 490                 495

Phe His Ala Trp Asn Lys Arg Cys Pro Gly Lys Pro Ile Met Ile Thr
            500                 505                 510

Glu Tyr Gly Ala Asp Thr Val Ala Gly Phe His Asp Ile Asp Pro Val
        515                 520                 525

Met Phe Thr Glu Glu Tyr Gln Val Glu Tyr Tyr Gln Ala Asn His Val
    530                 535                 540

Val Phe Asp Glu Phe Glu Asn Phe Val Gly Glu Gln Ala Trp Asn Phe
545                 550                 555                 560

Ala Asp Phe Ala Thr Ser Gln Gly Val Met Arg Val Gln Gly Asn Lys
                565                 570                 575

Lys Gly Val Phe Thr Arg Asp Arg Lys Pro Lys Leu Ala Ala His Val
            580                 585                 590

Phe Arg Glu Arg Trp Thr Asn Ile Pro Asp Phe Gly Tyr Lys Asn Ser
        595                 600                 605

His His His His His His Val
    610                 615


<210> SEQ ID NO 29
<211> LENGTH: 16
<212> TYPE: PRT
<213> ORGANISM: Bacillus sp.

<400> SEQUENCE: 29

Met Leu Ile Ile Thr Cys Asn His Leu His Leu Lys Arg Ser Ala Ile
 1               5                  10                  15


<210> SEQ ID NO 30
<211> LENGTH: 4
<212> TYPE: PRT
<213> ORGANISM: Unknown
<220> FEATURE:
<223> OTHER INFORMATION: Sequence that directs proteins to cytoplasm
      that may be added to the reference GUS

<400> SEQUENCE: 30

Lys Asp Glu Leu
 1


<210> SEQ ID NO 31
<211> LENGTH: 6
<212> TYPE: PRT
<213> ORGANISM: Escherichia coli

<400> SEQUENCE: 31

Asp Phe Phe Asn Tyr Ala
 1               5


<210> SEQ ID NO 32
<211> LENGTH: 5
```

-continued

<212> TYPE: PRT
<213> ORGANISM: Escherichia coli

<400> SEQUENCE: 32

Trp Asn Phe Ala Asp
 1               5

<210> SEQ ID NO 33
<211> LENGTH: 36
<212> TYPE: DNA
<213> ORGANISM: Artificial Sequence
<220> FEATURE:
<223> OTHER INFORMATION: PCR primer

<400> SEQUENCE: 33
aattaaccct cactaaacgg ayttyttyaa ytaygc 36

<210> SEQ ID NO 34
<211> LENGTH: 39
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (28)...(28)
<223> OTHER INFORMATION: n = inosine

<400> SEQUENCE: 34
gtaatacgac tcactatagg ggaartcngc raarttcca 39

<210> SEQ ID NO 35
<211> LENGTH: 17
<212> TYPE: DNA
<213> ORGANISM: Artificial Sequence
<220> FEATURE:
<223> OTHER INFORMATION: PCR primer

<400> SEQUENCE: 35
atcgcacgtc ccactac 17

<210> SEQ ID NO 36
<211> LENGTH: 18
<212> TYPE: DNA
<213> ORGANISM: Artificial Sequence
<220> FEATURE:
<223> OTHER INFORMATION: PCR primer

<400> SEQUENCE: 36
cgtgcgatag gagttagc 18

<210> SEQ ID NO 37
<211> LENGTH: 22
<212> TYPE: DNA
<213> ORGANISM: Artificial Sequence
<220> FEATURE:
<223> OTHER INFORMATION: PCR primer

<400> SEQUENCE: 37
atttagaaca tctcattatc cc 22

<210> SEQ ID NO 38
<211> LENGTH: 23
<212> TYPE: DNA
<213> ORGANISM: Artificial Sequence
<220> FEATURE:
<223> OTHER INFORMATION: PCR primer

<400> SEQUENCE: 38
tgagatgttc taaatgaatt agc 23

<210> SEQ ID NO 39
<211> LENGTH: 17
<212> TYPE: DNA
<213> ORGANISM: Artificial Sequence
<220> FEATURE:
<223> OTHER INFORMATION: PCR primer

<400> SEQUENCE: 39
atcgtgaccg gacgctt 17

<210> SEQ ID NO 40
<211> LENGTH: 17
<212> TYPE: DNA
<213> ORGANISM: Artificial Sequence
<220> FEATURE:
<223> OTHER INFORMATION: PCR primer

<400> SEQUENCE: 40
gcgcgtaatc ttcctgg 17

<210> SEQ ID NO 41
<211> LENGTH: 19
<212> TYPE: DNA
<213> ORGANISM: Artificial Sequence
<220> FEATURE:
<223> OTHER INFORMATION: PCR primer

<400> SEQUENCE: 41
tagcgacctt cgctttcgg 19

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
atcatgttta cagagtatgg 20

<210> SEQ ID NO 43
<211> LENGTH: 21
<212> TYPE: DNA
<213> ORGANISM: Artificial Sequence
<220> FEATURE:
<223> OTHER INFORMATION: PCR primer

<400> SEQUENCE: 43
ggaatattgc acaatgggcg c 21

<210> SEQ ID NO 44
<211> LENGTH: 23
<212> TYPE: DNA
<213> ORGANISM: Artificial Sequence
<220> FEATURE:
<223> OTHER INFORMATION: PCR primer

<400> SEQUENCE: 44
gatctctacg catttcaccg cta 23

<210> SEQ ID NO 45

-continued

<211> LENGTH: 17
<212> TYPE: DNA
<213> ORGANISM: Artificial Sequence
<220> FEATURE:
<223> OTHER INFORMATION: PCR primer

<400> SEQUENCE: 45
atggtaagac cgcaacg 17

<210> SEQ ID NO 46
<211> LENGTH: 25
<212> TYPE: DNA
<213> ORGANISM: Artificial Sequence
<220> FEATURE:
<223> OTHER INFORMATION: PCR primer

<400> SEQUENCE: 46
taaaaaccat ggtaagaccg caacg 25

<210> SEQ ID NO 47
<211> LENGTH: 20
<212> TYPE: DNA
<213> ORGANISM: Artificial Sequence
<220> FEATURE:
<223> OTHER INFORMATION: PCR primer

<400> SEQUENCE: 47
cctcactcca cagtcttctc 20

<210> SEQ ID NO 48
<211> LENGTH: 30
<212> TYPE: DNA
<213> ORGANISM: Artificial Sequence
<220> FEATURE:
<223> OTHER INFORMATION: PCR primer

<400> SEQUENCE: 48
agaccgctag cctcactcca cagtcttctc 30

<210> SEQ ID NO 49
<211> LENGTH: 22
<212> TYPE: DNA
<213> ORGANISM: Artificial Sequence
<220> FEATURE:
<223> OTHER INFORMATION: PCR primer

<400> SEQUENCE: 49
tttgactttt tcaactatgc ag 22

<210> SEQ ID NO 50
<211> LENGTH: 23
<212> TYPE: DNA
<213> ORGANISM: Artificial Sequence
<220> FEATURE:
<223> OTHER INFORMATION: PCR primer

<400> SEQUENCE: 50
aattctgcat agttgaaaaa gtc 23

<210> SEQ ID NO 51
<211> LENGTH: 35
<212> TYPE: DNA
<213> ORGANISM: Artificial Sequence
<220> FEATURE:
<223> OTHER INFORMATION: Product of sythesis to facilitate protein
purification

<400> SEQUENCE: 51
gtcgacccat ggtagatctg actagtctgt acccg 35

<210> SEQ ID NO 52
<211> LENGTH: 30
<212> TYPE: DNA
<213> ORGANISM: Artificial Sequence
<220> FEATURE:
<223> OTHER INFORMATION: Product of synthesis to facilitate construction and cloning

<400> SEQUENCE: 52
gtcgacagga gtgctatcat gctgtacccg 30

<210> SEQ ID NO 53
<211> LENGTH: 30
<212> TYPE: DNA
<213> ORGANISM: Artificial Sequence
<220> FEATURE:
<223> OTHER INFORMATION: Product of synthesis to facilitate protein purification

<400> SEQUENCE: 53
gtcgacagga gtgctaccat ggtgtacccg 30

<210> SEQ ID NO 54
<211> LENGTH: 36
<212> TYPE: DNA
<213> ORGANISM: Artificial Sequence
<220> FEATURE:
<223> OTHER INFORMATION: Product of synthesis to facilitate protein purification

<400> SEQUENCE: 54
gtcgacagga gtgctaccat ggtagatctg tacccg 36

<210> SEQ ID NO 55
<211> LENGTH: 41
<212> TYPE: DNA
<213> ORGANISM: Artificial Sequence
<220> FEATURE:
<223> OTHER INFORMATION: Product of synthesis to facilitate protein purification

<400> SEQUENCE: 55
gctagccatc accatcacca tcacgtgtga attggtgacc g 41

<210> SEQ ID NO 56
<211> LENGTH: 9
<212> TYPE: PRT
<213> ORGANISM: Artificial Sequence
<220> FEATURE:
<223> OTHER INFORMATION: Product of synthesis to facilitate protein purification

<400> SEQUENCE: 56

Ser Ser His His His His His His Val
1 5

<210> SEQ ID NO 57
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS -continued

<400> SEQUENCE: 57
tcgacccatg gtagatctga ctagtctgta cccgatcaac accgagaccc gtggcgtctt 60
cgacctcaat ggcgtctgga 80

<210> SEQ ID NO 58
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 58
ggatttcctt ggtcacgcca atgtcattgt aactgcttgg gacggccata ctaatagtgt 60
cggtcagctt gctttcgtac 80

<210> SEQ ID NO 59
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 59
ccaagcagtt acaatgacat tggcgtgacc aaggaaatcc gcaaccatat cggatatgtc 60
tggtacgaac gtgagttcac 80

<210> SEQ ID NO 60
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 60
gcggagcacg atacgctgat ccttcagata ggccggcacc gtgaactcac gttcgtacca 60
gacatatccg atatggttgc 80

<210> SEQ ID NO 61
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 61
ggtgccggcc tatctgaagg atcagcgtat cgtgctccgc ttcggctctg caactcacaa 60
agcaattgtc tatgtcaatg 80

<210> SEQ ID NO 62
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable -continued micorbial GUS

<400> SEQUENCE: 62
aatggcagga atccgccctt gtgctccacg accagctcac cattgacata gacaattgct 60
ttgtgagttg cagagccgaa 80

<210> SEQ ID NO 63
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 63
gtgagctggt cgtggagcac aagggcggat tcctgccatt cgaagcggaa atcaacaact 60
cgctgcgtga tggcatgaat 80

<210> SEQ ID NO 64
<211> LENGTH: 100
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 64
gtacagcccc accggtaggg tgctatcgtc gaggatgttg tccacggcga cggtgacgcg 60
attcatgcca tcacgcagcg agttgttgat ttccgcttcg 00

<210> SEQ ID NO 65
<211> LENGTH: 56
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 65
cgcgtcaccg tcgccgtgga caacatcctc gacgatagca ccctaccggt ggggct 56

<210> SEQ ID NO 66
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 66
cacttctctt ccagtccttt cccgtagtcc agcttgaagt tccagacgcc attgaggtcg 60
aagacgccac gggtctcggt 80

<210> SEQ ID NO 67
<211> LENGTH: 35
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS -continued

<400> SEQUENCE: 67
ttgatcgggt acagactagt cagatctacc atggg 35

<210> SEQ ID NO 68
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 68
acttcaagct ggactacggg aaaggactgg aagagaagtg gtacgaaagc aagctgaccg 60
acactattag tatggccgtc 80

<210> SEQ ID NO 69
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 69
gtacagcgag cgccacgaag agggcctcgg aaaagtcatt cgtaacaagc cgaacttcga 60
cttcttcaac tatgcaggcc 80

<210> SEQ ID NO 70
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 70
ctttgccttg aaagtccacc gtataggtca cagtcccggt tgggccattg aagtcggtca 60
caaccgagat gtcctcgacg 80

<210> SEQ ID NO 71
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 71
accgggactg tgacctatac ggtggacttt caaggcaaag ccgagaccgt gaaagtgtcg 60
gtcgtggatg aggaaggcaa 80

<210> SEQ ID NO 72
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 72
ctccacgtta ccgctcaggc cctcggtgct tgcgaccact ttgccttcct catccacgac 60
cgacactttc acggtctcgg 80

<210> SEQ ID NO 73
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 73
agtggtcgca agcaccgagg gcctgagcgg taacgtggag attccgaatg tcatcctctg 60
ggaaccactg aacacgtatc 80

<210> SEQ ID NO 74
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 74
gtcagtccgt cgttcaccag ttccactttg atctggtaga gatacgtgtt cagtggttcc 60
cagaggatga cattcggaat 80

<210> SEQ ID NO 75
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 75
tctaccagat caaagtggaa ctggtgaacg acggactgac catcgatgtc tatgaagagc 60
cgttcggcgt gcggaccgtg 80

<210> SEQ ID NO 76
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 76
acggtttgtt gttgatgagg aacttgccgt cgttgacttc cacggtccgc acgccgaacg 60
gctcttcata gacatcgatg 80

<210> SEQ ID NO 77
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS -continued

<400> SEQUENCE: 77
gaagtcaacg acggcaagtt cctcatcaac aacaaaccgt tctacttcaa gggctttggc 60
aaacatgagg acactcctat 80

<210> SEQ ID NO 78
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 78
tacgtaaacg gggtcgtgta gattttcacc ggacggtgca ggcctgcata gttgaagaag 60
tcgaagttcg gcttgttacg 80

<210> SEQ ID NO 79
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 79
atccatcaca ttgctcgctt cgttaaagcc acggccgttg ataggagtgt cctcatgttt 60
gccaaagccc ttgaagtaga 80

<210> SEQ ID NO 80
<211> LENGTH: 75
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 80
caacggccgt ggctttaacg aagcgagcaa tgtgatggat ttcaatatcc tcaaatggat 60
cggcgccaac agctt 75

<210> SEQ ID NO 81
<211> LENGTH: 36
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 81
aatgactttt ccgaggccct cttcgtggcg ctcgct 36

<210> SEQ ID NO 82
<211> LENGTH: 39
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 82
ccggaagctg ttggcgccga tccatttgag gatattgaa 39

<210> SEQ ID NO 83
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 83
tgcaccgtcc ggtgaaaatc tacacgaccc cgtttacgta cgtcgaggac atctcggttg 60
tgaccgactt caatggccca 80

<210> SEQ ID NO 84
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 84
ccggaccgca cactatccgt actctgaaga gttgatgcgt cttgcggatc gcgagggtct 60
ggtcgtgatc gacgagactc 80

<210> SEQ ID NO 85
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 85
gttcacggag aacgtcttga tggtgctcaa acgtccgaat cttctcccag gtactgacgc 60
gctcgctgcc ttcgccgagt 80

<210> SEQ ID NO 86
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 86
attcggacgt ttgagcacca tcaagacgtt ctccgtgaac tggtgtctcg tgacaagaac 60
catccaagcg tcgtgatgtg 80

<210> SEQ ID NO 87
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 87

-continued cgcgccctct tcctcagtcg ccgcctcgtt ggcgatgctc cacatcacga cgcttggatg 60
gttcttgtca cgagacacca 80

<210> SEQ ID NO 88
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 88
gagcatcgcc aacgaggcgg cgactgagga agagggcgcg tacgagtact tcaagccgtt 60
ggtggagctg accaaggaac 80

<210> SEQ ID NO 89
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 89
acaaacagca cgatcgtgac cggacgcttc tgtgggtcga gttccttggt cagctccacc 60
aacggcttga agtactcgta 80

<210> SEQ ID NO 90
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 90
tcgacccaca gaagcgtccg gtcacgatcg tgctgtttgt gatggctacc ccggagacgg 60
acaaagtcgc cgaactgatt 80

<210> SEQ ID NO 91
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 91
cgaagtacca tccgttatag cgattgagcg cgatgacgtc aatcagttcg gcgactttgt 60
ccgtctccgg ggtagccatc 80

<210> SEQ ID NO 92
<211> LENGTH: 89
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS -continued

<400> SEQUENCE: 92
gacgtcatcg cgctcaatcg ctataacgga tggtacttcg atggcggtga tctcgaagcg 60
gccaaagtcc atctccgcca ggaatttca 89

<210> SEQ ID NO 93
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 93
cccgtggtgg ccatgaagtt gaggtgcacg ccaactgccg gagtctcgtc gatcacgacc 60
agaccctcgc gatccgcaag 80

<210> SEQ ID NO 94
<211> LENGTH: 53
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 94
cgcgtgaaat tcctggcgga gatggacttt ggccgcttcg agatcaccgc cat 53

<210> SEQ ID NO 95
<211> LENGTH: 36
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 95
acgcatcaac tcttcagagt acggatagtg tgcggt 36

<210> SEQ ID NO 96
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 96
cggcagttgg cgtgcacctc aacttcatgg ccaccacggg actcggcgaa ggcagcgagc 60
gcgtcagtac ctgggagaag 80

<210> SEQ ID NO 97
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 97
cgcgtggaac aagcgttgcc caggaaagcc gatcatgatc actgagtacg gcgcagacac 60

-continued cgttgcgggc tttcacgaca 80

<210> SEQ ID NO 98
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 98
tcgcgaagtc cgcgaagttc cacgcttgct cacccacgaa gttctcaaac tcatcgaaca 60
cgacgtggtt cgcctggtag 80

<210> SEQ ID NO 99
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 99
ttcgtgggtg agcaagcgtg gaacttcgcg gacttcgcga cctctcaggg cgtgatgcgc 60
gtccaaggaa acaagaaggg 80

<210> SEQ ID NO 100
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable micorbial GUS

<400> SEQUENCE: 100
gtgcgcggcg agcttcggct tgcggtcacg agtgaacacg cccttcttgt ttccttggac 60
gcgcatcacg ccctgagagg 80

<210> SEQ ID NO 101
<211> LENGTH: 80
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable microbial GUS.

<400> SEQUENCE: 101
cgtgttcact cgtgaccgca agccgaagct cgccgcgcac gtctttcgcg agcgctggac 60
caacattcca gatttcggct 80

<210> SEQ ID NO 102
<211> LENGTH: 89
<212> TYPE: DNA
<213> ORGANISM: Artificial Sequence
<220> FEATURE:
<223> OTHER INFORMATION: Oligonucleotide. Product of synthesis to overlap and create fragments of an engineered secreatable microbial GUS.

<400> SEQUENCE: 102

-continued

```
cggtcaccaa ttcacacgtg atggtgatgg tgatggctag cgttcttgta gccgaaatct     60

ggaatgttgg tccagcgctc gcgaaagac                                       89


<210> SEQ ID NO 103
<211> LENGTH: 53
<212> TYPE: DNA
<213> ORGANISM: Artificial Sequence
<220> FEATURE:
<223> OTHER INFORMATION: Oligonucleotide.  Product of synthesis to
      overlap and create fragments of an engineered secreatable
      microbial GUS.

<400> SEQUENCE: 103

acaagaacgc tagccatcac catcaccatc acgtgtgaat tggtgaccgg gcc            53


<210> SEQ ID NO 104
<211> LENGTH: 80
<212> TYPE: DNA
<213> ORGANISM: Artificial Sequence
<220> FEATURE:
<223> OTHER INFORMATION: Oligonucleotide.  Product of synthesis to
      overlap and create fragments of an engineered secreatable
      microbial GUS.

<400> SEQUENCE: 104

tactcgactt gatattcctc ggtgaacatc actggatcaa tgtcgtgaaa gcccgcaacg     60

gtgtctgcgc cgtactcagt                                                 80


<210> SEQ ID NO 105
<211> LENGTH: 36
<212> TYPE: DNA
<213> ORGANISM: Artificial Sequence
<220> FEATURE:
<223> OTHER INFORMATION: Oligonucleotide.  Product of synthesis to
      overlap and create fragments of an engineered secreatable
      microbial GUS.

<400> SEQUENCE: 105

gatcatgatc ggctttcctg ggcaacgctt gttcca                               36


<210> SEQ ID NO 106
<211> LENGTH: 80
<212> TYPE: DNA
<213> ORGANISM: Artificial Sequence
<220> FEATURE:
<223> OTHER INFORMATION: Oligonucleotide.  Product of synthesis to
      overlap and create fragments of an engineered secreatable
      microbial GUS.

<400> SEQUENCE: 106

ttgatccagt gatgttcacc gaggaatatc aagtcgagta ctaccaggcg aaccacgtcg     60

tgttcgatga gtttgagaac                                                 80


<210> SEQ ID NO 107
<211> LENGTH: 60
<212> TYPE: DNA
<213> ORGANISM: Unknown
<220> FEATURE:
<223> OTHER INFORMATION: Invertase signal sequence used in yeast vector.

<400> SEQUENCE: 107

atgcttttgc aagccttcct tttccttttg gctggttttg cagccaaaat atctgcaatg     60


<210> SEQ ID NO 108
<211> LENGTH: 258
```

-continued

<212> TYPE: DNA
<213> ORGANISM: Unknown
<220> FEATURE:
<223> OTHER INFORMATION: Mat alpha signal sequence used in yeast vector.

<400> SEQUENCE: 108
atgagatttc cttcaatttt tactgcagtt ttattcgcag catcctccgc attagctgct 60
ccagtcaaca ctacaacaga agatgaaacg gcacaaattc cggctgaagc tgtcatcggt 120
tacttagatt tagaagggga tttcgatgtt gctgttttgc cattttccaa cagcacaaat 180
aacgggttat tgtttataaa tactactatt gccagcattg ctgctaaaga agaaggggta 240
tctttggata aaagagag 258

<210> SEQ ID NO 109
<211> LENGTH: 88
<212> TYPE: DNA
<213> ORGANISM: Unknown
<220> FEATURE:
<223> OTHER INFORMATION: Extensin signal sequence used in plant vector.

<400> SEQUENCE: 109
catgggaaaa atggcttctc tatttgccac atttttagtg gttttagtgt cacttagctt 60
agcttctgaa agctcagcaa attatcaa 88

<210> SEQ ID NO 110
<211> LENGTH: 82
<212> TYPE: DNA
<213> ORGANISM: Unknown
<220> FEATURE:
<223> OTHER INFORMATION: GRP signal sequence used in plant vector.

<400> SEQUENCE: 110
catggctact actaagcatt tggctcttgc catccttgtc ctccttagca ttggtatgac 60
caccagtgca agaaccctcc ta 82

<210> SEQ ID NO 111
<211> LENGTH: 42
<212> TYPE: DNA
<213> ORGANISM: Artificial Sequence
<220> FEATURE:
<223> OTHER INFORMATION: Oligonucleotide used in “quickchange” mutagenesis.
<220> FEATURE:
<221> NAME/KEY: misc_feature
<222> LOCATION: (1)...(42)
<223> OTHER INFORMATION: n = A,T,C or G

<400> SEQUENCE: 111
ttcctgccat tcgaggcgga aatcnngaac tcgctgcgtg at 42

<210> SEQ ID NO 112
<211> LENGTH: 43
<212> TYPE: DNA
<213> ORGANISM: Artificial Sequence
<220> FEATURE:
<223> OTHER INFORMATION: Oligonucleotide used in “quickchange” mutagenesis.
<220> FEATURE:
<221> NAME/KEY: misc_feature
<222> LOCATION: (1)...(43)
<223> OTHER INFORMATION: n = A,T,C or G

<400> SEQUENCE: 112
atcacgcagc gagttcnnga tttccgcctc gaatggcagg aat 43

MICROBIAL β-GLUCURONIDASE GENES, GENE PRODUCTS AND USES THEREOF

CROSS-REFERENCE TO RELATED APPLICATIONS

This application is a continuation of U.S. application Ser. No. 09/270,957, filed Mar. 17, 1999, now U.S. Pat. No. 6,641,996, which is a continuation-in-part of U.S. application Ser. No. 09/149,727, filed Sep. 8, 1998, now U.S. Pat. No. 6,391,547 which claims the benefit of U.S. Provisional Application No. 60/058,263, filed Sep. 9, 1997; these applications are incorporated by reference in their entirety.

TECHNICAL FIELD

The present invention relates generally to microbial β-glucuronidases, and more specifically to secreted forms of β-glucuronidase, and uses of these β-glucuronidases.

BACKGROUND OF THE INVENTION

The enzyme β-glucuronidase (GUS; E.C.3.2.1.31) hydrolyzes a wide variety of glucuronides. Virtually any aglycone conjugated to D-glucuronic acid through a β-O-glycosidic linkage is a substrate for GUS. In vertebrates, glucuronides containing endogenous as well as xenobiotic compounds are generated through a major detoxification pathway and excreted in urine and bile.

*Escherichia coli*, the major organism resident in the large intestine of vertebrates, utilizes the glucuronides generated in the liver and other organs as an efficient carbon source. Glucuronide substrates are taken up by *E. coli* via a specific transporter, the glucuronide pernease (U.S. Pat. Nos. 5,288,463 and 5,432,081), and cleaved by β-glucuronidase, releasing glucuronic acid residues that are used as a carbon source. In general, the aglycone component of the glucuronide substrate is not used by *E. coli* and passes back across the bacterial membrane into the gut to be reabsorbed into the bloodstream and undergo glucuronidation in the liver, beginning the cycle again. In *E. coli*, β-glucuronidase is encoded by the gusA gene (Novel and Novel, *Mol. Gen. Genet.* 120:319-335, 1973), which is one member of an operon comprising two other protein-encoding genes, gusB encoding a permease (PER) specific for β-glucuronides, and gusC encoding an outer membrane protein (OMP) that facilitates access of glucuronides to the permease located in the inner membrane.

While β-glucuronidase activity is expressed in almost all tissues of vertebrates and their resident intestinal flora, GUS activity is absent in most other organisms. Notably, plants, most bacteria, fungi, and insects are reported to largely, if not completely, lack GUS activity. Thus, GUS is ideal as a reporter molecule in these organisms and has become one of the most widely used reporter systems for these organisms.

In addition, because both endogenous and xenobiotic compounds are generally excreted from vertebrates as glucuronides, β-glucuronidase is widely used in medical diagnostics, such as drug testing. In therapeutics, GUS has been used as an integral component of prodrug therapy. For example, a conjugate of GUS and a targeting molecules, such as an antibody specific for a tumor cell type, is delivered along with a nontoxic prodrug, provided as a glucuronide. The antibody targets the cell and GUS cleaves the prodrug, releasing an active drug at the target site.

Because the *E. coli* GUS enzyme is much more active and stable than the mammalian enzyme against most biosynthetically derived β-glucuronides (Tomasic and Keglevic, *Biochem J* 133:789, 1973; Levvy and Conchie, 1966), the *E. coli* GUS is preferred in both reporter and medical diagnostic systems.

Production of GUS for use in in vitro assays, such as medical diagnostics, however, is costly and requires extensive manipulation as GUS must be recovered from cell lysates. A secreted form of GUS would reduce manufacturing expenses, however, attempts to cause secretion have been largely unsuccessful. In addition, for use in transgenic organisms, the current GUS system has somewhat limited utility because enzymatic activity is detected intracellularly by deposition of toxic calorimetric products during the staining or detection of GUS. Moreover, in cells that do not express a glucuronide permease, the cells must be permeabilized or sectioned to allow introduction of the substrate. Thus, this conventional staining procedure generally results in the destruction of the stained cells. In light of these limitations, a secreted GUS would facilitate development of non-destructive marker systems, especially useful for agricultural field work.

Furthermore, the *E. coli* enzyme, although more robust than vertebrate GUS, has characteristics that limit its usefulness. For example, it is heat-labile and inhibited by detergents and end product (glucuronic acid). For many applications, a more resilient enzyme would be beneficent.

The present invention provides gene and protein sequences of microbial β-glucuronidases, variants thereof, and use of the proteins as a transformation marker, effector molecule, and component of medical diagnostic and therapeutic systems, while providing other related advantages.

SUMMARY OF INVENTION

In one aspect, an isolated nucleic acid molecule is provided comprising a nucleic acid sequence encoding a microbial of β-glucuronidase, provided that the β-glucuronidase is not from *E. coli*. Nucleic acid sequences are provided for β-glucuronidases from *Thermotoga, Bacillus, Staphylococcus, Salmonella, Enterobacter*, and *Pseudomonas*. In certain embodiments, the nucleic acid molecule encoding β-glucuronidase is derived from a eubacteria, such as purple bacteria, gram(+) bacteria, cyanobacteria, spirochaetes, green sulphur bacteria, bacteroides and flavobacteria, planctomyces, chlamydiae, radioresistant micrococci, and thermotogales.

In another aspect, microbial β-glucuronidases are provided that have enhanced characteristics. In one aspect, thermostable β-glucuronidases and nucleic acids encoding them are provided. In general, a thermostable β-glucuronidase has a half-life of at least 10 min at 65° C. In preferred embodiments, the thermostable β-glucuronidase is from Thermotoga or *Bacillus* groups. In other embodiments, the β-glucuronidase converts at least 50 nmoles of p-nitrophenyl-glucuronide to p-nitrophenyl per minute, per microgram of protein. In even further embodiments, the β-glucuronidase retains at least 80% of its activity in 10 mM glucuronic acid.

In another aspect, fusion proteins of microbial β-glucuronidase or an enzymatically active portion thereof are provided. In certain embodiments, the fusion partner is an antibody or fragment thereof that binds antigen.

In other aspects, expression vectors comprising a gene encoding a microbial β-glucuronidase or a portion thereof that has enzymatic activity in operative linkage with a heterologous promoter are provided. In such a vector, the microbial β-glucuronidase is not *E. coli* β-glucuronidase. In the expression vectors, the heterologous promoter is a promoter selected from the group consisting of a developmental type-specific promoter, a tissue type-specific promoter, a cell type-specific promoter and an inducible promoter. The promoter should be functional in the host cell for the expression vector. Examples of cell types include a plant cell, a bacterial cell, an animal cell and a fungal cell. In certain embodiments, the expression vector also comprises a nucleic acid sequence encoding a product of a gene of interest or portion thereof. The gene of interest may be under control of the same or a different promoter.

Isolated forms of recombinant microbial β-glucuronidase are also provided in this invention, provided that the microbial β-glucuronidase is not *E. coli* β-glucuronidase. The recombinant β-glucuronidases may be from eubacteria, archaea, or eucarya. When eubacteria β-glucuronidases are clones, the eubacteria is selected from purple bacteria, gram(+) bacteria, cyanobacteria, spirochaetes, green sulphur bacteria, bacteroides and flavobacteria, planctomyces, chlamydiae, radioresistant micrococci, and thermotogales and the like.

The present invention also provides methods for monitoring expression of a gene of interest or a portion thereof in a host cell, comprising: (a) introducing into the host cell a vector construct, the vector construct comprising a nucleic acid molecule according to claim 1 and a nucleic acid molecule encoding a product of the gene of interest or a portion thereof; (b) detecting the presence of the microbial β-glucuronidase, thereby monitoring expression of the gene of interest; methods for transforming a host cell with a gene of interest or portion thereof, comprising: (a) introducing into the host cell a vector construct, the vector construct comprising a nucleic acid sequence encoding a microbial β-glucuronidase, provided that the microbial β-glucuronidase is not *E. coli* β-glucuronidase, and a nucleic acid sequence encoding a product of the gene of interest or a portion thereof, such that the vector construct integrates into the genome of the host cell; and (b) detecting the presence of the microbial β-glucuronidase, thereby establishing that the host cell is transformed.

Methods are also provided for positive selection for a transformed cell, comprising: (a) introducing into a host cell a vector construct, the vector construct comprising nucleic acid sequence encoding a microbial β-glucuronidase, provided that the microbial β-glucuronidase is not *E. coli* β-glucuronidase; (b) exposing the host cell to the sample comprising a glucuronide, wherein the glucuronide is cleaved by the β-glucuronidase, such that the compound is released, wherein the compound is required for cell growth. In all these methods, a microbial glucuronide permease gene may be also introduced.

Transgenic plants expressing a microbial β-glucuronidase other than *E. coli* β-glucuronidase are also provided. The present invention also provides seeds of transgenic plants. Transgenic animals, such as aquatic animals are also provided. Methods for identifying a microorganism that secretes β-glucuronidase, are provided comprising: (a) culturing the microorganism in a medium containing a substrate for β-glucuronidase, wherein the cleaved substrate is detectable, and wherein the microorganism is an isolate of a naturally occurring microorganism or a transgenic microorganism; and (b) detecting the cleaved substrate in the medium. In certain embodiments, the microorganism is cultured under specific conditions that are favorable to particular microorganisms.

In another aspect, a method for providing an effector compound to a cell in a transgenic plant is provided. The method comprises (a) growing a transgenic plant that comprises an expression vector, comprising a nucleic acid sequence encoding a microbial β-glucuronidase in operative linkage with a heterologous promoter and a nucleic acid sequence comprising a gene encoding a cell surface receptor for an effector compound and (b) exposing the transgenic plant to a glucuronide, wherein the glucuronide is cleaved by the β-glucuronidase, such that the effector compound is released. This method is especially useful for directing glucuronides to particular and specific cells by further introducing into the transgenic plant a vector construct comprising a nucleic acid sequence that binds the effector compound. The effector compound can then be used to control expression of a gene of interest by linking a gene of interest with the nucleic acid sequence that binds the effector compound.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIGS. 1A–B present DNA sequence of an approximately 6 kb fragment that encodes β-glucuronidase from *Bacillus.*

FIGS. 3A–B present amino acid sequences (SEQ ID Nos: 2–6) of representative microbial β-glucuronidases.

FIGS. 4A–J present DNA sequences (SEQ ID Nos: 7–14) of representative microbial β-glucuronidases.

FIGS. 5A–C present amino acid alignments of *Bacillus* GUS (BGUS) (SEQ ID NO: 15) *E. coli* GUS (EGUS) (SEQ ID NO: 16) and human GUS (HGUS) (SEQ ID NO: 17) (5A). Microbial GUSes (5B) (SEQ ID Nos: 18–23) and nucleotide sequence alignments (SEQ ID Nos: 24–26) of *Bacillus, Salmonella*, and *Pseudomonas* β-glucuronidases.

FIGS. 13A–C present a DNA sequence of *Bacillus* GUS that is codon-optimized for production in *E. coli.*

FIG. 15 presents schematics of two expression vectors for use in yeast (upper figure) and plants (lower figure).

DETAILED DESCRIPTION OF THE INVENTION

Figure 2:
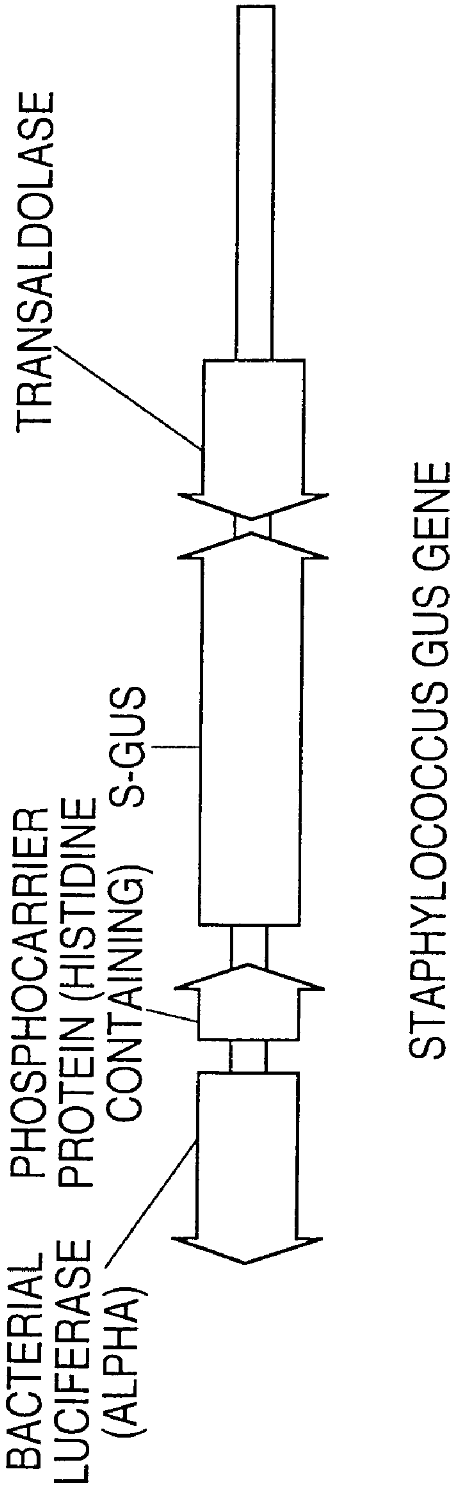
FIG. 2 is a schematic of the DNA sequence of a *Bacillus* 6 kb fragment showing the location and orientation of the major open reading frames. S-GUS is β-glucuronidase.

Prior to setting forth the invention, it may be helpful to an understanding thereof to set forth definitions of certain terms that will be used hereinafter.

As used herein, "β-glucuronidase" refers to an enzyme that catalyzes the hydrolysis of β-glucuronides. Assays and some exemplary substrates for determining β-glucuronidase activity, also known as GUS activity, are provided in U.S. Pat. No. 5,268,463. In assays to detect β-glucuronidase activity, fluorogenic or chromogenic substrates are preferred. Such substrates include, but are not limited to, p-nitrophenyl β-D-glucuronide and 4-methylumbelliferyl β-D-glucuronide.

As used herein, a "secreted form of a microbial β-glucuronidase" refers to a microbial β-glucuronidase that is capable of being localized to an extracellular environment of a cell, including extracellular fluids, periplasm, or membrane bound on the external face of a cell but not membrane bound as an integral membrane protein. Some of the protein may be found intracellularly. The amino acid and nucleotide sequences of an exemplary secreted β-glucuronidase are presented in FIG. 1 and SEQ ID Nos.: 1 and 2. Secreted microbial GUS also encompasses variants of β-glucuronidase. A variant may be a portion of the secreted β-glucuronidase and/or have amino acid substitutions, insertions, and deletions, either found naturally as a polymorphic allele or constructed.

As used herein, "percent sequence identity" is a percentage determined by the number of exact matches of amino acids or nucleotides to a reference sequence divided by the number of residues in the region of overlap. Within the context of this invention, preferred amino acid sequence identity for a variant is at least 75% and preferably greater than 80%, 85%, 90% or 95%. Such amino acid sequence identity may be determined by standard methodologies, including use of the National Center for Biotechnology Information BLAST search methodology available at www.ncbi.nlm.nih.gov. The identity methodologies preferred are non-gapped BLAST. However, those described in U.S. Pat. No. 5,691,179 and Altschul et al., Nucleic Acids Res. 25:3389–3402, 1997 all of which are incorporated herein by reference are also useful. Accordingly, if Gapped BLAST 2.0 is utilized, then it is utilized with default settings. Further, a nucleotide variant will typically be sufficiently similar in sequence to hybridize to the reference sequence under stringent hybridization conditions (for nucleic acid molecules over about 500 bp, stringent conditions include a solution comprising about 1 M Na+ at 25° to 30° C. below the Tm; e.g., 5×SSPE, 0.5% SDS, at 65° C.; see, Ausubel, et al., *Current Protocols in Molecular Biology*, Greene Publishing, 1995; Sambrook et al., *Molecular Cloning: A Laboratory Manual*, Cold Spring Harbor Press, 1989). Some variants may not hybridize to the reference sequence because of codon degeneracy, such as degeneracies introduced for codon optimization in a particular host, in which case amino acid identity may be used to assess similarity of the variant to the reference protein.

As used herein, a "glucuronide" or "β-glucuronide" refers to an aglycone conjugated in a hemiacetal linkage, typically through the hydroxyl group, to the C1 of a free D-glucuronic acid in the β configuration. Glucuronides include, but are not limited to, O-glucuronides linked through an oxygen atom, S-glucuronides, linked through a sulfur atom, N-glucuronides, linked through a nitrogen atom and C-glucuronides, linked through a carbon atom (see, Dutton, *Glucuronidation of Drugs and Other Compounds*, CRC Press, Inc. Boca Raton, Fla. pp13–15). β-glucuronides consist of virtually any compound linked to the C1-position of glucuronic acid as a beta anomer, and are typically, though by no means exclusively, found as an O-glycoside. β-glucuronides are produced naturally in most vertebrates through the action of UDP-glucuronyl transferase as a part of the process of solubilizing, detoxifying, and mobilizing both natural and xenobiotic compounds, thus directing them to sites of excretion or activity through the circulatory system.

β-glucuronides in polysaccharide form are also common in nature, most abundantly in vertebrates, where they are major constituents of connective and lubricating tissues in polymeric form with other sugars such as N-acetylglucosamine (e.g., chondroitan sulfate of cartilage, and hyaluronic acid, which is the principle constituent of synovial fluid and mucus). Other polysaccharide sources of β-glucuronides occur in bacterial cell walls, e.g., cellobiuronic acid. β-glucuronides are relatively uncommon or absent in plants. Glucuronides and galacturonides found in plant cell wall components (such as pectin) are generally in the alpha configuration, and are frequently substituted as the 4-O-methyl ether; hence, such glucuronides are not substrates for β-glucuronidase.

An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

Microbial β-glucuronidase Genes

As noted above, this invention provides gene sequences and gene products for microbial β-glucuronidase including secreted β-glucuronidase. As exemplified herein, genes from microorganisms, including a gene from *Bacillus* that encodes a secreted β-glucuronidase, are identified and characterized biochemically, genetically, and by DNA sequence analysis. Exemplary isolations of β-glucuronidase genes and gene products from several phylogenetic groups, including *Bacillus, Thermotoga, Pseudomonas, Salmonella, Staphylococcus, Enterobacter, Arthobacter*, and the like, are provided herein. Microbial β-glucuronidases from additional organisms may be identified as described herein or by hybridization of one of the microbial β-glucuronidase gene sequence to genomic or cDNA libraries, by genetic complementation, by function, by amplification, by antibody screening of an expression library and the like (see Sambrook et al., infra Ausubel et al., infra for methods and conditions appropriate for isolation of a β-glucuronidase from other species).

The existence of a microbial β-glucuronidase may be observed by a variety of methods and procedures. Particularly useful screens for identifying β-glucuronidase are biochemical screening and genetic complementation. Test samples containing microbes, may be obtained from sources such as soil, animal or human skin, saliva, mucous, feces, water, and the like. Microbes present in such samples include organisms from the phylogenetic domains, Eubacteria, Archaea, and Eucarya (Woese, *Microbiol. Rev.* 58: 1–9, 1994), the Eubacteria phyla: purple bacteria (including the α, β, γ, and δ subdivisions), gram (+) bacteria (including the high G+C content, low G+C content, and photosynthetic subdivisions), cyanobacteria, spirochaetes, green sulphur bacteria, bacteroides and flavobacteria, planctomyces and relatives, chlamydiae, radioresistant micrococci and relatives, and thermotogales. It will be appreciated by those in the art that the names and number of the phyla may vary somewhat according to the precise criteria for categorization (see Strunk et al., *Electrophoresis* 19: 554, 1998). Other microbes include, but are not limited to, entamoebae, fungi, and protozoa.

Colonies of microorganisms are generally obtained by plating on a suitable substrate in appropriate conditions. Conditions and substrates will vary according to the growth requirements of the microorganism. For example, anoerobic conditions, liquid culture or special defined media may be used to grow the microorganisms. Many different selective media have been devised to grow specific microorganisms (see, e.g, Merck Media Handbook). Substrates such as deoxycholate, citrate, etc. may be used to inhibit extraneous and undesired organisms such as gram-positive cocci and spore forming bacilli. Other substances to identify particular microbes (e.g., lactose fermenters, gram positives) may also be used. A glucuronide substrate is added that is readily detectable when cleaved by β-glucuronidase. A microbe that secretes β-glucuronidase should exhibit a diffuse staining (halo) pattern surrounding the colony.

A complementation assay may be additionally performed to verify that the staining pattern is due to expression of a GUS gene or to assist in isolating and cloning the GUS gene. Briefly, in this assay, the candidate GUS gene is transfected into an *E. coli* strain that is deleted for the GUS operon (e.g., KW1 described herein), and the staining pattern of the transfectant is compared to a mock-transfected host. For cloning by complementation, microbial genomic DNA is digested by e.g., restriction enzyme reaction and ligated to a vector, which ideally is an expression vector. The recombinants are transfected into a host strain, which ideally is deleted for endogenous GUS gene (e.g., KW1). In some cases, the host strain may express GUS gene but preferably not in the compartment to be assayed. If GUS is secreted, the transfectant should exhibit a diffuse staining pattern (halo) surrounding the colony, whereas, the host will not.

The microorganisms can be identified in myriad ways, including morphology, virus sensitivity, sequence similarity, metabolism signatures, and the like. A preferred method is similarity of rRNA sequence determined after amplification of genomic DNA. A region of rRNA is chosen that is flanked by conserved sequences that will anneal amplification primers. The amplification product is subjected to DNA sequence analysis and compared to known rRNA sequences described herein.

In one exemplary screen, a bacterial colony isolated from a soil sample displays a strong, diffuse staining pattern. The bacterium is identified as a *Bacillus* by sequence determination of 16S rRNA after amplification. A genomic library from this *Bacillus* is constructed in the vector pBSII KS+. The recombinant plasmids are transfected into KW1, a strain deleted for the β-glucuronidase operon. One resulting colony, containing the plasmid pRAJa17.1, exhibited a strong, diffuse staining pattern similar to the *Bacillus* isolate.

In other exemplary screens of microorganisms found in soil and in skin samples, numerous microbes exhibit a diffuse staining pattern around the colony or stained blue. The phylogenetic classifications of some of these are determined by sequence analysis of 16S rRNA. At least eight different genera are represented. Genetic complementation assays demonstrate that the staining pattern is most likely due to expression of the GUS gene. Not all complementation assays yield positive results, however, which may be due to the background genotype of the receptor strain or to restriction enzyme digestion within the GUS gene. The DNA sequence and predicted amino acid sequences of the GUS genes from several of these microorganisms found in these screens microorganisms are determined.

Figures 2, 5B:
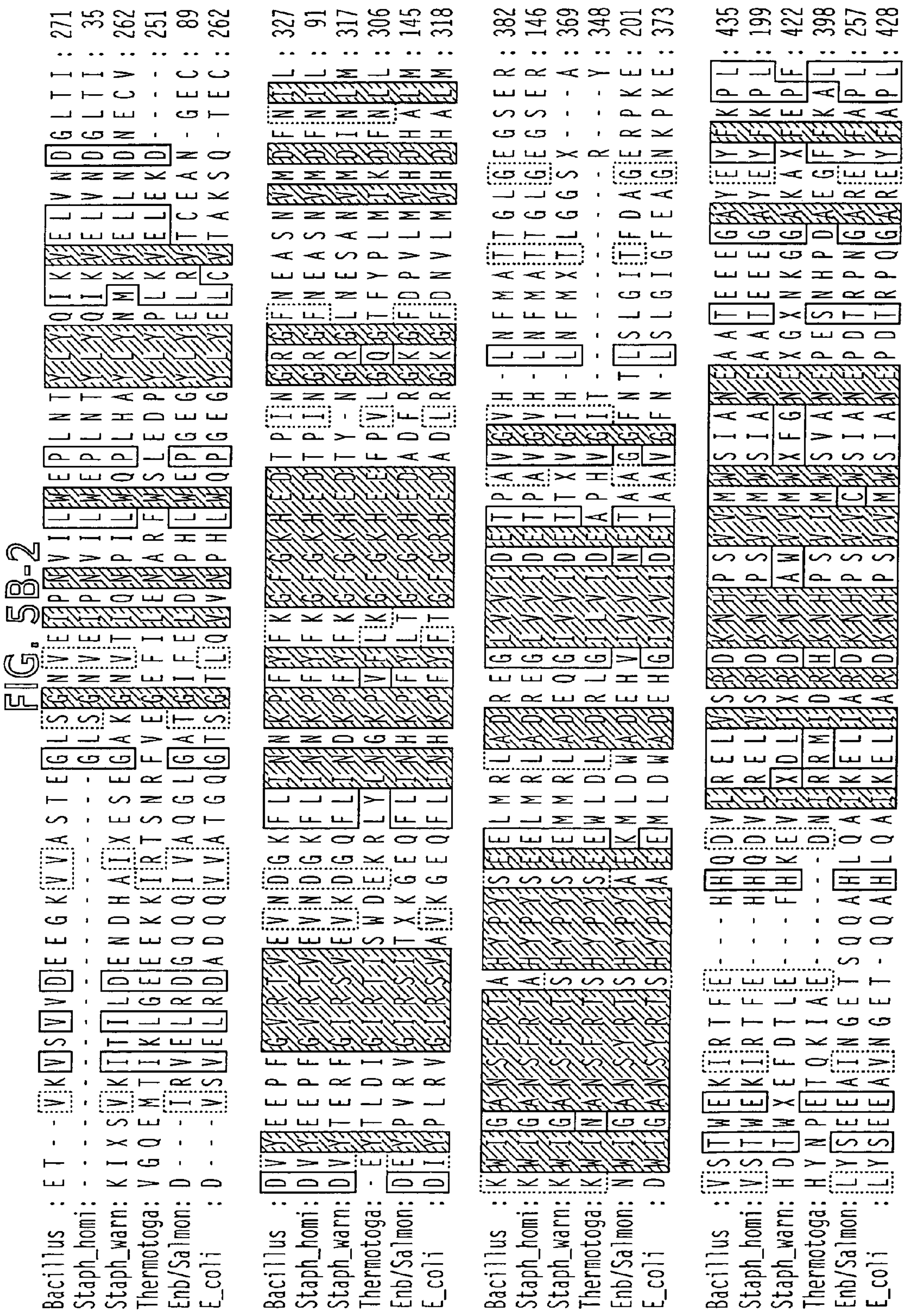
Figures 1, 5C:
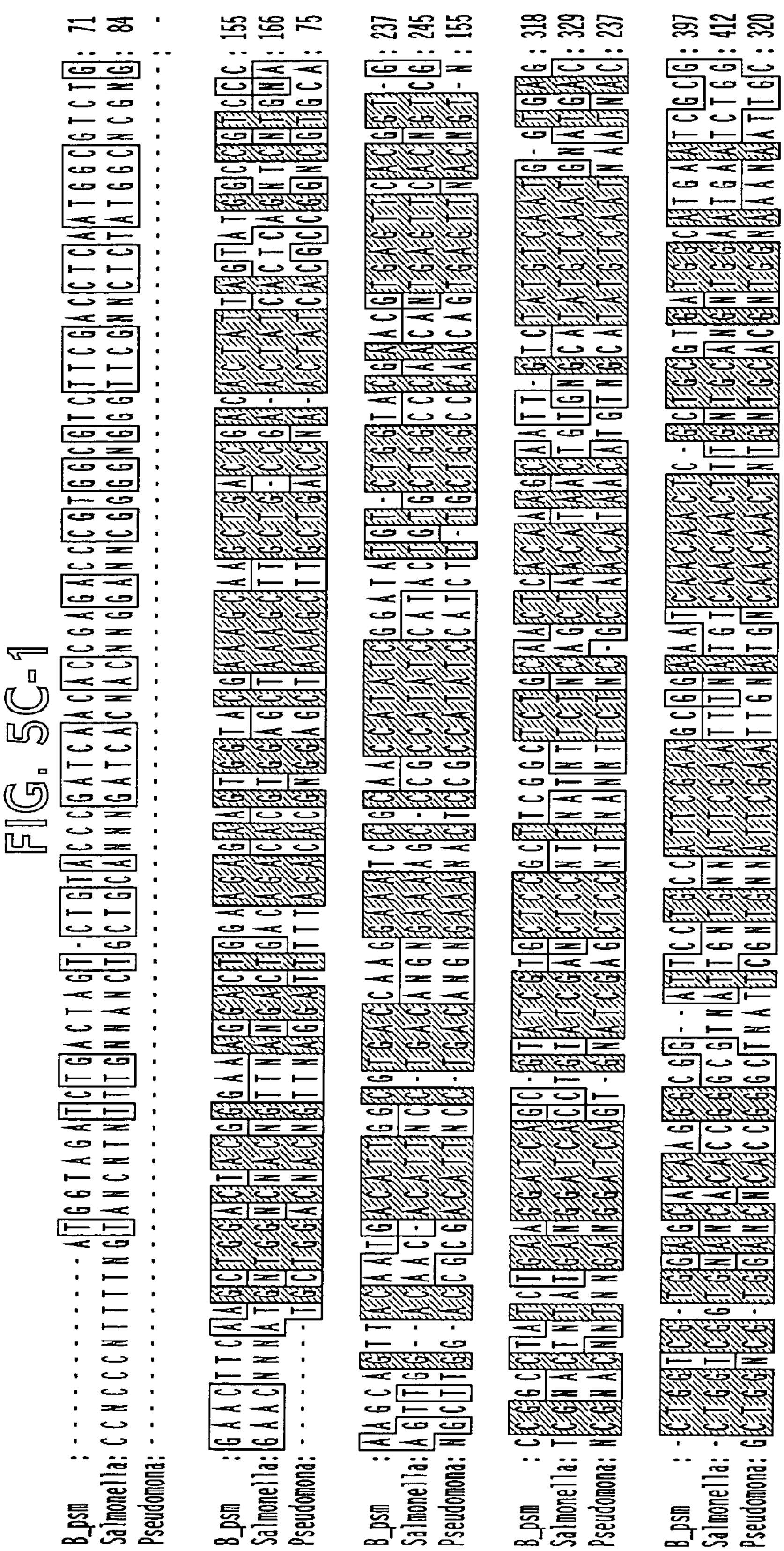
Figures 2, 5C:
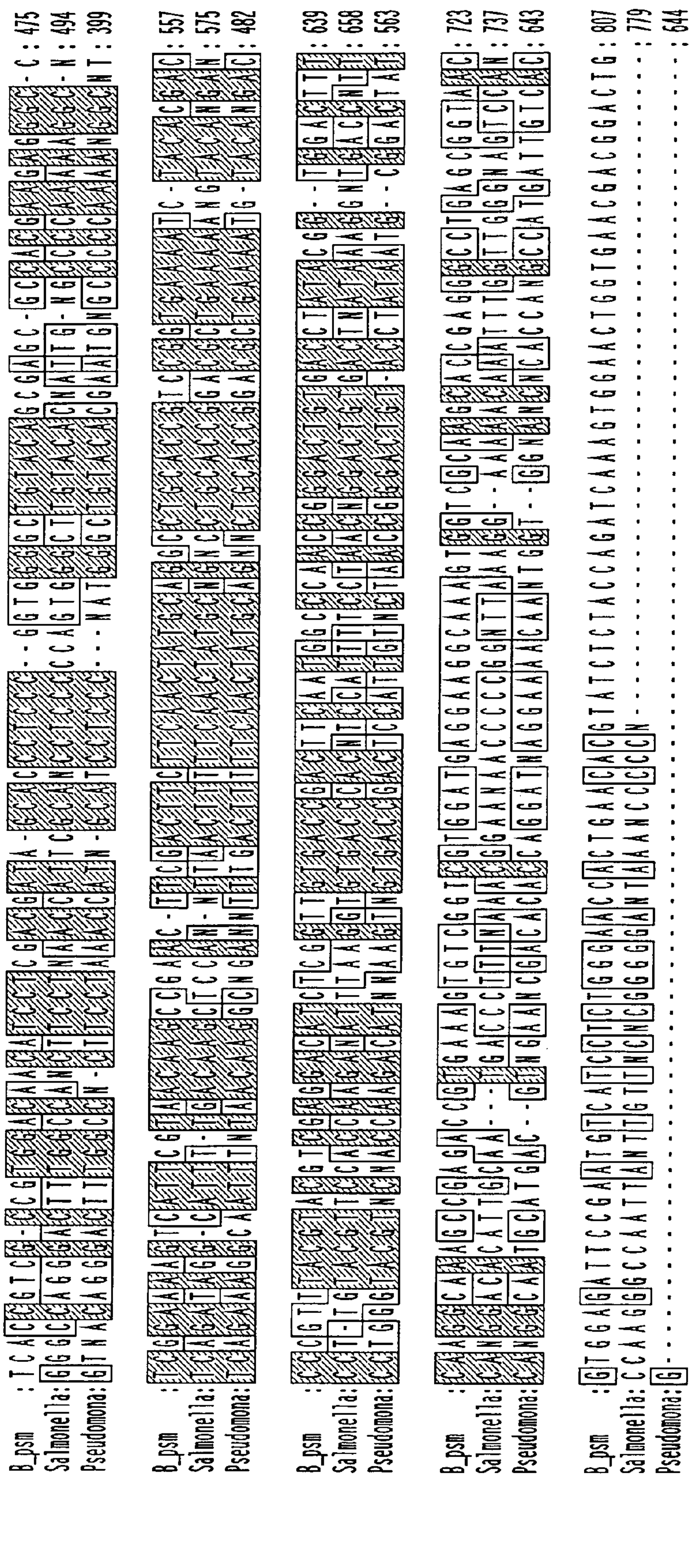

A DNA sequence of the GUS gene contained in the insert of pRAJa17.1 is presented in FIG. 1 and as SEQ ID NO: 1. A schematic of the insert is presented in FIG. 2. The β-glucuronidase gene contained in the insert is identified by similarity of the predicted amino acid sequence of an open reading frame to the *E. coli* and human β-glucuronidase amino acid sequences (FIG. 5A). Overall, *Bacillus* β-glucuronidase has approximately 47–49% amino acid identity to *E. coli* GUS and to human GUS. An open reading frame of *Bacillus* GUS is 1854 bases, which would result in a protein that is 618 amino acids in length. The first methionine codon, however, is unlikely to encode the initiator methionine. Rather the second methionine codon is most likely the initiator methionine. Such a translated product is 602 amino acids long and is the sequence presented in FIGS. 3A–B and 4A–I. The assignment of the initiator methionine is based upon a consensus Shine-Dalgarno sequence found upstream of the second Met, but not the first Met, and alignment of the *Bacillus*, human, and *E. coli* GUS amino acid sequences. Furthermore, as shown herein, *Bacillus* GUS gene lacking sequence encoding the 16 amino acids is expressed in *E. coli* transfectants. In addition, the 16 amino acids (Met-Leu-Ile-Ile-Thr-Cys-Asn-His-Leu-His-Leu-Lys-Arg-Ser-Ala-Ile) (SEQ ID NO: 29) are not a canonical signal peptide sequence.

There is a single Asn-Asn-Ser sequence (residues 118–120 in FIGS. 3A–B) that can serve as a site for N-glycosylation in the ER. Furthermore, unlike the *E. coli* and human β-glucuronidases, which have 9 and 4 cysteines respectively, the *Bacillus* protein has only a single Cys residue (residue 499 in FIGS. 3A–B).

The DNA sequences of GUS genes from *Staphylococcus homini, Staphylococcus warneri, Thermotoga maritima* (TIGR *Thermotoga* database), *Enterobacter, Salmonella*, and *Pseudomonas* are presented in FIGS. 4A–J and (SEQ ID Nos: 7–14). Predicted amino acid sequences are shown in FIGS. 3A–B and (SEQ ID Nos: 2–6). The amino acid sequences are shown in alignment in FIGS. 5A–C. The signature peptide sequences for glycosyl hydrolases (Henrissat, *Biochem Soc Trans* 26:153, 1998; Henrissat B et al., *FEBS Lett* 27:425, 1998) are located from amino acids 333 to 358 and from amino acids 406 to 420 (*Bacillus* numbering in FIGS. 3A and 5B). The catalytic nucleophile is Glu 344 (*Bacillus* numbering) (Wong et al., *J. Biol Chem.* 18: 34057, 1998). Within these two signature regions, 17/26 and 8/15 residues are identical across the six presented sequences. At the non-identical positions, most of the sequences share an identical residue. Thus, the sequences are highly conserved in these regions (identity between *Bacillus* and each other GUS gene ranges from 65% to 100% in signature 1 and from 73% to 100% in signature 2) (see FIG. 5B). In contrast, between *Bacillus* and β-galactosidase, another glycosyl hydrolase that has signature sequences, identity is 46% in signature 1 and 73% in signature 2.

In addition, portions or fragments of microbial GUS may be isolated or constructed for use in the present invention. For example, restriction fragments can be isolated by well-known techniques from template DNA, e.g., plasmid DNA, and DNA fragments, including restriction fragments, can be generated by amplification. Furthermore, oligonucleotides can be synthesized or isolated from recombinant DNA molecules. One skilled in the art will appreciated that other methods are available to obtain DNA or RNA molecules having at least a portion of a microbial GUS sequence. Moreover, for particular applications, these nucleic acids may be labeled by techniques known in the art, such as with a radiolabel (e.g., $^{32}P$, $^{33}P$, $^{35}S$, $^{125}I$, $^{131}I$, $^{3}H$, $^{14}C$), fluorescent label (e.g., FITC, Cy5, RITC, Texas Red), chemiluminescent label, enzyme, biotin and the like.

In certain aspects, the present invention provides fragments of microbial GUS genes. Fragments may be at least 17 nucleotides long (e.g., at least 20 nt, 25 nt, 30 nt, 40 nt, 50 nt). Fragments may be used in hybridization methods (see, exemplary conditions described infra) or inserted into appropriate vector for expression or production. In certain aspects, the fragments have sequences of one or both of the signatures or have sequence from at least some of the more highly conserved regions of GUS (e.g., from approximately amino acids 272–360 and from amino acids 398–421 or from amino acids 398–545; based on *Bacillus* numbering in FIG. 5B). In the various embodiments, useful fragments comprise those nucleic acid sequences which encode at least the active residue at position 344 (*Bacillus* numbering in FIG. 5B) and, preferably, comprise nucleic acid sequences 697–1624, 703–1620, 751–1573, 805–1398, 886–1248, 970–1059, and 997–1044 (*Bacillus* numbering in FIGS. 4A–4C). In other embodiments, oligonucleotides of microbial GUSes are provided especially for use as amplification primers. In such case, the oligonucleotides are at least 12 bases and preferably at least 15 bases (e.g., at least 18, 21, 25, 30 bases) and generally not longer than 35 bases. It will be appreciated that any of these fragments described herein can be double-stranded, single-stranded, derived from coding strand or complementary strand and be exact or mismatched sequence.

Microbial β-glucuronidase Gene Products

The present invention also provides β-glucuronidase gene products in various forms. Forms of the GUS protein include, but are not limited to, secreted forms, membrane-bound forms, cytoplasmic forms, fusion proteins, chemical conjugates of GUS and another molecule, portions of GUS protein, and other variants. GUS protein may be produced by recombinant means, biochemical isolation, and the like.

In certain aspects, variants of secreted microbial GUS are useful within the context of this invention. Variants include nucleotide or amino acid substitutions, deletions, insertions, and chimeras. Typically, when the result of synthesis, amino acid substitutions are conservative, i.e., substitution of amino acids within groups of polar, non-polar, aromatic, charged, etc. amino acids. As will be appreciated by those skilled in the art, a nucleotide sequence encoding microbial GUS may differ from the wild-type sequence presented in the Figures, due to codon degeneracies, nucleotide polymorphisms, or amino acid differences. In certain embodiments, variants preferably hybridize to the wild-type nucleotide sequence at conditions of normal stringency, which is approximately 25–30° C. below Tm of the native duplex (e.g., 1 M Na+ at 65° C.; e.g. 5×SSPE, 0.5% SDS, 5× Denhardt's solution, at 65° C. or equivalent conditions; see generally, Sambrook et al. *Molecular Cloning: A Laboratory Manual,* 2nd ed., Cold Spring Harbor Press, 1987; Ausubel et al., *Current Protocols in Molecular Biology*, Greene Publishing, 1987). Alternatively, the Tm for other than short oligonucleotides can be calculated by the formula Tm=81.5+0.41%(G+C)−log[Na+]. Low stringency hybridizations are performed at conditions approximately 40° C. below Tm, and high stringency hybridizations are performed at conditions approximately 10° C. below Tm.

Variants may be constructed by any of the well known methods in the art (see, generally, Ausubel et al., supra; Sambrook et al., supra). Such methods include site-directed oligonucleotide mutagenesis, restriction enzyme digestion and removal or insertion of bases, amplification using primers containing mismatches or additional nucleotides, splicing of another gene sequence to the reference microbial GUS gene, and the like. Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. Similarly, deletions and/or insertions may be constructed by any of a variety of known methods. For example, the gene can be digested with restriction enzymes and religated such that some sequence is deleted or ligated with an isolated fragment having cohesive ends so that an insertion or large substitution is made. In another embodiment, variants are generated by shuffling of regions (see U.S. Pat. No. 5,605,793). Variant sequences may also be generated by "molecular evolution" techniques (see U.S. Pat. No. 5,723,323). Other means to generate variant sequences may be found, for example, in Sambrook et al. (supra) and Ausubel et al. (supra). Verification of variant sequences is typically accomplished by restriction enzyme mapping, sequence analysis, or probe hybridization, although other methods may be used. The double-stranded nucleic acid is transformed into host cells, typically *E. coli*, but alternatively, other prokaryotes, yeast, or larger eukaryotes may be used. Standard screening protocols, such as nucleic acid hybridization, amplification, and DNA sequence analysis, can be used to identify mutant sequences.

In addition to directed mutagenesis in which one or a few amino acids are altered, variants that have multiple substitutions may be generated. The substitutions may be scattered throughout the protein or functional domain or concentrated in a small region. For example, a region may be mutagenized by oligonucleotide-directed mutagenesis in which the oligonucleotide contains a string of dN bases or the region is excised and replaced by a string of dN bases. Thus, a population of variants with a randomized amino acid sequence in a region is generated. The variant with the desired properties (e.g., more efficient secretion) is then selected from the population.

In preferred embodiments, the protein and variants are capable of being secreted and exhibit β-glucuronidase activity. A GUS protein is secreted if the amount of secretion expressed as a secretion index is statistically significantly higher for the candidate protein compared to a standard, typically *E. coli* GUS. Secretion index maybe calculated as the percentage of total GUS activity in periplasm or other extracellular environment less the percentage of total β-galactosidase activity found in the same extracellular environment.

In other preferred embodiments, a microbial GUS or its variant will exhibit one or more of the biochemical characteristics exhibited by *Bacillus* GUS, such as its increased thermal stability, its higher turnover number, and its activity in detergents, presence of end product, high salt conditions and organic solvents as compared to an *E. coli* GUS standard.

In certain preferred embodiments, the microbial GUS is thermostable having a half-life of at least 10 minutes at 65° C. (e.g., 14 minutes, 16 minutes, 18 minutes). In other preferred embodiments, GUS protein has a turnover number, expressed as nanomoles of p-nitrophenyl-β-D-glucuronide converted to p-nitrophenol per minute per µg of purified protein, of at least 50 and more preferably at least 60, at least 70, at least 80 and at least 90 nanomoles measured at its temperature optimum. In other preferred embodiments the turnover number is at least 20, at least 30, or at least 40 nanomoles at room temperature. In yet other preferred embodiments, the β-glucuronidase should not be substantially inhibited by the presence of detergents such as SDS (e.g., 0.1%, 1%, 5%), Triton® X-100 (e.g., 0.1%, 1%, 5%), or sarcosyl (e.g., 0.1%, 1%, 5%). In other preferred embodiments, the GUS enzyme is not substantially inhibited (e.g., less than 50% inhibition and more preferably less than 20% inhibition) by either at 1 mM or as high as 10 mM glucuronic acid. In still other preferred embodiments, GUS retains substantial activity (at least 50% and preferably at least 70%) in organic solvents, such as dimethylformamide, dimethylsulfoxide and in salt (e.g., NaCl).

In other preferred embodiments, GUS and variants thereof are capable of being secreted and exhibit one or more of the biochemical characteristics disclosed herein. In other embodiments, variants of microbial GUS are capable of binding to a hapten, such as biotin, dinitrophenol, and the like.

In other embodiments, variants may exhibit glucuronide binding activity without enzymatic activity or be directed to other cellular compartments, such as membrane or cytoplasm. Membrane-spanning amino acid sequences are generally hydrophobic and many examples of such sequences are well-known. These sequences may be spliced onto microbial secreted GUS by a variety of methods including conventional recombinant DNA techniques. Similarly, sequences that direct proteins to cytoplasm (e.g., Lys-Asp-Glu-Leu) (SEQ ID NO: 30) may be added to the reference GUS, typically by recombinant DNA techniques.

In other embodiments, a fusion protein comprising GUS may be constructed from the nucleic acid molecule encoding microbial and another nucleic acid molecule. As will be appreciated, the fusion partner gene may contribute, within certain embodiments, a coding region. In preferred embodiments, microbial GUS is fused to avidin, streptavidin or an antibody. Thus, it may be desirable to use only the catalytic site of GUS (e.g., amino acids 415–508 reference to *Bacillus* sequence). The choice of the fusion partner depends in part upon the desired application. The fusion partner may be used to alter specificity of GUS, provide a reporter function, provide a tag sequence for identification or purification protocols, and the like. The reporter or tag can be any protein that allows convenient and sensitive measurement or facilitates isolation of the gene product and does not interfere with the function of GUS. For example, green fluorescent protein and β-galactosidase are readily available as DNA sequences. A peptide tag is a short sequence, usually derived from a native protein, which is recognized by an antibody or other molecule. Peptide tags include FLAG®, Glu-Glu tag (Chiron Corp., Emeryville, Calif.), KT3 tag (Chiron Corp.), T7 gene 10 tag (Invitrogen, La Jolla, Calif.), T7 major capsid protein tag (Novagen, Madison, Wis.), $His_6$ (hexa-His), and HSV tag (Novagen). Besides tags, other types of proteins or peptides, such as glutathione-S-transferase may be used.

In other aspects of the present invention, isolated microbial glucuronidase proteins are provided. In one embodiment, GUS protein is expressed as a hexa-His fusion protein and isolated by metal-containing chromatography, such as nickel-coupled beads. Briefly, a sequence encoding $His_6$ is linked to a DNA sequence encoding a GUS. Although the $His_6$ sequence can be positioned anywhere in the molecule, preferably it is linked at the 3' end immediately preceding the termination codon. The His-GUS fusion may be constructed by any of a variety of methods. A convenient method is amplification of the GUS gene using a downstream primer that contains the codons for $His_6$.

In one aspect of the present invention, peptides having microbial GUS sequence are provided. Peptides may be used as immunogens to raise antibodies, as well as other uses. Peptides are generally five to 100 amino acids long, and more usually 10 to 50 amino acids. Peptides are readily chemically synthesized in an automated fashion (e.g., PerkinElmer, ABI Peptide Synthesizer) or may be obtained commercially. Peptides may be further purified by a variety of methods, including high-performance liquid chromatography (HPLC). Furthermore, peptides and proteins may contain amino acids other than the 20 naturally occurring amino acids or may contain derivatives and modification of the amino acids.

β-glucuronidase protein may be isolated by standard methods, such as affinity chromatography using matrices containing saccharose lactone, phenythio-β-glucuronide, antibodies to GUS protein and the like, size exclusion chromatography, ionic exchange chromatography, HPLC, and other known protein isolation methods. (see generally Ausubel et al. supra; Sambrook et al. supra). The protein can be expressed as a hexa-His fusion protein and isolated by metal-affinity chromatography, such as nickel-coupled beads. An isolated purified protein gives a single band on SDS-PAGE when stained with Coomassie brilliant blue.

Antibodies to Microbial GUS

Antibodies to microbial GUS proteins, fragments, or peptides discussed herein may readily be prepared. Such antibodies may specifically recognize reference microbial GUS protein and not a mutant (or variant) protein, mutant (or variant) protein and not wild type protein, or equally recognize both the mutant (or variant) and wild-type forms. Antibodies may be used for isolation of the protein, inhibiting (antagonist) activity of the protein, or enhancing (agonist) activity of the protein.

Within the context of the present invention, antibodies are understood to include monoclonal antibodies, polyclonal antibodies, anti-idiotypic antibodies, antibody fragments (e.g., Fab, and $F(ab')_2$, $F_v$ variable regions, or complementarity determining regions). Antibodies are generally accepted as specific against GUS protein if they bind with a $K_d$ of greater than or equal to $10^{-7}$ M, preferably greater than of equal to $10^{-8}$ M. The affinity of a monoclonal antibody or binding partner can be readily determined by one of ordinary skill in the art (see Scatchard, *Ann. N.Y. Acad. Sci.* 51:660–672, 1949).

Briefly, a polyclonal antibody preparation may be readily generated in a variety of warm-blooded animals such as rabbits, mice, or rats. Typically, an animal is immunized with GUS protein or peptide thereof, which may be conjugated to a carrier protein, such as keyhole limpet hemocyanin. Routes of administration include intraperitoneal, intramuscular, intraocular, or subcutaneous injections, usually in an adjuvant (e.g., Freund's complete or incomplete adjuvant). Particularly preferred polyclonal antisera demonstrate binding in an assay that is at least three times greater than background.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual*, Harlow and Lane (eds.), Cold Spring Harbor Laboratory Press, 1988). Briefly, within one embodiment, a subject animal such as a rat or mouse is injected with GUS or a portion thereof. The protein may be administered as an emulsion in an adjuvant such as Freund's complete or incomplete adjuvant in order to increase the immune response. Between one and three weeks after the initial immunization the animal is generally boosted and may tested for reactivity to the protein utilizing well-known assays. The spleen and/or lymph nodes are harvested and immortalized. Various immortalization techniques, such as mediated by Epstein-Barr virus or fusion to produce a hybridoma, may be used. In a preferred embodiment, immortalization occurs by fusion with a suitable myeloma cell line (e.g., NS-1 (ATCC No. TIB 18), and P3x63-Ag 8.653 (ATCC No. CRL 1580) to create a hybridoma that secretes monoclonal antibody. The preferred fusion partners do not express endogenous antibody genes. Following fusion, the cells are cultured in medium containing a reagent that selectively allows for the growth of fused spleen and myeloma cells such as HAT (hypoxanthine, aminopterin, and thymidine) and are subsequently screened for the presence of antibodies that are reactive against a GUS protein. A wide variety of assays may be utilized, including for example countercurrent immuno-electrophoresis, radioimmunoassays, radioimmunoprecipitations, enzyme-linked immunosorbent assays (ELISA), dot blot assays, western blots, immunoprecipitation, inhibition or competition assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988).

Other techniques may also be utilized to construct monoclonal antibodies (see Huse et al., Science 246:1275–1281, 1989; Sastry et al., *Proc. Natl. Acad. Sci. USA* 86:5728–5732, 1989; Alting-Mees et al., *Strategies in Molecular Biology* 3:1–9, 1990; describing recombinant techniques). Briefly, RNA is isolated from a B cell population and utilized to create heavy and light chain immunoglobulin cDNA expression libraries in suitable vectors, such as λImmunoZap(H) and λImmunoZap(L). These vectors may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli.*

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources (e.g., Stratacyte, La Jolla, Calif.) Amplification products are inserted into vectors such as ImmunoZAP™ H or ImmunoZAP™ L (Stratacyte), which are then introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423–426, 1988). In addition, techniques may be utilized to change a "murine" antibody to a "human" antibody, without altering the binding specificity of the antibody.

One of ordinary skill in the art will appreciate that a variety of alternative techniques for generating antibodies exist. In this regard, the following U.S. patents teach a variety of these methodologies and are thus incorporated herein by reference: U.S. Pat. Nos. 5,840,479; 5,770,380; 5,204,244; 5,482,856; 5,849,288; 5,780,225; 5,395,750; 5,225,539; 5,110,833; 5,693,762; 5,693,761; 5,693,762; 5,698,435; and 5,328,834.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC (e.g., reversed phase, size exclusion, ion-exchange), purification on protein A or protein G columns, or any combination of these techniques.

Assays for Function of β-glucuronidase

In preferred embodiments, microbial β-glucuronidase will have at least enzymatic activity and in other preferred embodiments, will also have the capability of being secreted. As noted above, variants of these reference GUS proteins may exhibit altered functional activity and cellular localization. Enzymatic activity may be assessed by an assay such as the ones disclosed herein or in U.S. Pat. No. 5,268,463 (Jefferson). Generally, a chromogenic or fluorogenic substrate is incubated with cell extracts, tissue sections, or purified protein. Cleavage of the substrate is monitored by a method appropriate for the aglycone.

A variety of methods may be used to demonstrate that a β-glucuronidase is secreted. For example, a rapid screening method in which colonies of organisms or cells, such as bacteria, yeast or insect cells, are plated and incubated with a readily visualized glucuronide substrate, such as X-GlcA. A colony with a diffuse staining pattern likely secretes GUS, although such a pattern could indicate that the cell has the ability to pump out the cleaved glucuronide, that the cell has become leaky, or that the enzyme is membrane bound. When test cells express GUS from an introduced vector, a cell that is known to not pump out cleaved substrate and is deleted for endogenous GUS genes is preferably used.

Secretion of the enzyme may be verified by assaying for GUS activity in the extracellular environment. If the cells secreting GUS are gram-positive bacteria, yeasts, molds, plants, or other organisms with cell walls, activity may be assayed in the culture medium and in a cell extract, however, the protein may not be transported through the cell wall. Thus, if no or low activity of a secreted form of GUS is found in the culture medium, protoplasts can be made by osmotic shock or enzymatic digestion of the cell wall or other suitable procedure, and the supernatant assayed for GUS activity. If the cells secreting GUS are gram-negative bacteria, culture supernatant may be tested, but more likely β-glucuronidase will be retained in the periplasmic space between the inner and outer membrane. In this case, spheroplasts may be made by osmotic shock, enzymatic digestion, or other suitable procedure, and the supernatant assayed for GUS activity. Cells without cell walls may be assayed for GUS in cell supernatant and cell extracts. The fraction of activity in each compartment is compared to the activity of a non-secreted GUS in the same or similar host cells. A β-glucuronidase is secreted if significantly more enzyme activity than *E. coli* GUS activity is found in extracellular spaces. The amount of secretion is generally normalized to the amount of a non-secreted protein found in extracellular spaces. Less than 10% of *E. coli* GUS is secreted. Higher amounts of secreted enzyme are preferred (e.g., greater than 20%, 25%, 30%, 40%, 50%).

β-glucuronidases that exhibit specific substrate specificities are also useful within the context of the present invention. As noted above, glucuronides can be linked through an oxygen, carbon, nitrogen or sulfur atom. Glucuronide substrates having each of the linkages may be used in one of the assays described herein. In addition, various glucuronides containing a variety of aglycones may be used.

Common glucuronides include:

Phenyl-β-glucuronide
Phenyl β-D-thio-glucuronide
p-Nitrophenyl-β-glucuronide
4-Methylumbelliferyl-β-glucuronide
p-Aminophenyl-β-D-glucuronide
p-Aminophenyl-1-thio-β-D-glucuronide
Chloramphenicol β-D-glucuronide
8-Hydroxyquinoline β-D-glucuronide
5-Bromo-4-chloro-3-indolyl-β-D-glucuronide (X-GlcA)
5-Bromo-6-chloro-3-indolyl-β-D-glucuronide (Magenta-GlcA)
6-Chloro-3-indolyl-β-D-glucuronide (Salmon-β-D-GlcA)
Indoxyl-β-D-glucuronide (Y-GlcA)
Androsterone-3-β-D-glucuronide
α-Naphthyl-β-D-glucuronide
Estriol-3-β-D-glucuronide
17-β-Estradiol-3-β-D-glucuronide.
Estrone-3-β-D-glucuronide
Testosterone-17-β-D-glucuronide
19-nor-Testosterone-17-β-D-glucuronide
Tetrahydrocortisone-3-β-D-glucuronide
Phenolphthalein-β-D-glucuronide
3'-Azido-3'-deoxythymidine-β-D-glucuronide
Methyl-β-D-glucuronide
Morphine-6-β-D-glucuronide Vectors, Host Cells and Means of Expressing and Producing Protein Microbial β-glucuronidase may be expressed in a variety of host organisms. For protein production and purification, GUS is preferably secreted and produced in bacteria, such as *E. coli*, for which many expression vectors have been developed and are available. Other suitable host organisms include other bacterial species (e.g., *Bacillus*, and eukaryotes, such as yeast (e.g., *Saccharomyces cerevisiae*), mammalian cells (e.g., CHO and COS-7), plant cells and insect cells (e.g., Sf9). Vectors for these hosts are well known.

A DNA sequence encoding microbial β-glucuronidase is introduced into an expression vector appropriate for the host. The sequence is derived from an existing clone or synthesized. As described herein, a fragment of the coding region may be used, but if enzyme activity is desired, the catalytic region should be included. A preferred means of synthesis is amplification of the gene from cDNA, genomic DNA, or a recombinant clone using a set of primers that flank the coding region or the desired portion of the protein. Restriction sites are typically incorporated into the primer sequences and are chosen with regard to the cloning site of the vector. If necessary, translational initiation and termination codons can be engineered into the primer sequences. The sequence of GUS can be codon-optimized for expression in a particular host. For example, a secreted form of β-glucuronidase isolated from a bacterial species that is expressed in a fungal host, such as yeast, can be altered in nucleotide sequence to use codons preferred in yeast. Codon-optimization may be accomplished by methods such as splice overlap extension, site-directed mutagenesis, automated synthesis, and the like.

At minimum, the vector must contain a promoter sequence. Other regulatory sequences may be included. Such sequences include a transcription termination signal sequence, secretion signal sequence, origin of replication, selectable marker, and the like. The regulatory sequences are operationally associated with one another to allow transcription or translation.

Expression in Bacteria

The plasmids used herein for expression of secreted GUS include a promoter designed for expression of the proteins in a bacterial host. Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, RSV LTR, SV40, metallothionein promoter (see, e.g., U.S. Pat. No. 4,870,009) and other inducible promoters. For expression of the proteins, a promoter is inserted in operative linkage with the coding region for β-glucuronidase.

The promoter controlling transcription of β-glucuronidase may be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the *E. coli* lacI repressor responsive to IPTG induction, the temperature sensitive λcI 857 repressor, and the like. The *E. coli* lacI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in bacterial cells. Thus, the vector preferably contains a bacterial origin of replication. Preferred bacterial origins of replication include the f1-ori and col E1 origins of replication, especially the ori derived from pUC plasmids.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene ($Amp^r$), tetracycline resistance gene ($Tc^r$) and the kanamycin resistance gene ($Kan^r$). Suitable markers for eukaryotes usually require a complementary deficiency in the host (e.g., thymidine kinase (tk) in tk-hosts). However, drug markers are also available (e.g., G418 resistance and hygromycin resistance).

The sequence of nucleotides encoding β-glucuronidase may also include a classical secretion signal, whereby the resulting peptide is a precursor protein processed and secreted. The resulting processed protein may be recovered from the periplasmic space or the fermentation medium. Secretion signals suitable for use are widely available and are well known in the art (von Heijne, *J. Mol. Biol.* 184: 99–105, 1985). Prokaryotic and eukaryotic secretion signals that are functional in *E. coli* (or other host) may be employed. The presently preferred secretion signals include, but are not limited to pelB, matα, extensin and glycine-rich protein.

One skilled in the art appreciates that there are a wide variety of suitable vectors for expression in bacterial cells and which are readily obtainable. Vectors such as the pET series (Novagen, Madison, Wis.) and the tac and trc series (Pharmacia, Uppsala, Sweden) are suitable for expression of a β-glucuronidase. A suitable plasmid is ampicillin resistant, has a colEI origin of replication, $lac^q$ gene, a lac/trp hybrid promoter in front of the lac Shine-Dalgarno sequence, a hexa-his coding sequence that joins to the 3' end of the inserted gene, and an rrnB terminator sequence.

The choice of a bacterial host for the expression of a β-glucuronidase is dictated in part by the vector. Commercially available vectors are paired with suitable hosts. The vector is introduced in bacterial cells by standard methodology. Typically, bacterial cells are treated to allow uptake of DNA (for protocols, see generally, Ausubel et al., supra; Sambrook et al., supra). Alternatively, the vector may be introduced by electroporation, phage infection, or another suitable method.

Expression in Plant Cells

As noted above, the present invention provides vectors capable of expressing microbial secreted β-glucuronidase and secreted microbial β-glucuronidases. For agricultural applications, the vectors should be functional in plant cells. Vectors and procedures for cloning and expression in *E. coli* and animal cells are discussed herein and, for example, in Sambrook et al (supra) and in Ausubel et al. (supra). Suitable plants include, but are not limited to, wheat, rice, corn, soybeans, lupins, vegetables, potatoes, canola, nut trees, coffee, alfalfa and other forage plants, cereals, legumes and the like. In one preferred embodiment, rice is a host for GUS gene expression.

Vectors that are functional in plants are preferably binary plasmids derived from *Agrobacterium* plasmids. Such vectors are capable of transforming plant cells. These vectors contain left and right border sequences that are required for integration into the host (plant) chromosome. At minimum, between these border sequences is the gene to be expressed under control of a promoter. In preferred embodiments, a selectable marker and a reporter gene are also included. The vector also preferably contains a bacterial origin of replication.

A gene for microbial β-glucuronidase should be in operative linkage with a promoter that is functional in a plant cell. Typically, the promoter is derived from a host plant gene, but promoters from other plant species and other organisms, such as insects, fungi, viruses, mammals, and the like, may also be suitable, and at times preferred. The promoter may be constitutive or inducible, or may be active in a certain tissue or tissues (tissue type-specific promoter), in a certain cell or cells (cell-type specific promoter), of at a particular stage or stages of development (development-type specific promoter). The choice of a promoter depends at least in part upon the application. Many promoters have been identified and isolated (see, generally, GenBank and EMBL databases). Other promoters may be isolated by well-known methods. For example, a genomic clone for a particular gene can be isolated by probe hybridization. The coding region is mapped by restriction mapping, DNA sequence analysis, RNase probe protection, or other suitable method. The genomic region immediately upstream of the coding region comprises a promoter region and is isolated. Generally, the promoter region is located in the first 200 bases upstream, but may extend to 500 or more bases. The candidate region is inserted in a suitable vector in operative linkage with a reporter gene, such as in pBI121 in place of the CaMV 35S promoter, and the promoter is tested by assaying for the reporter gene after transformation into a plant cell. (see, generally, Ausubel et al, supra; Sambrook et al., supra; *Methods in Plant Molecular Biology and Biotechnology*, Ed. Glick and Thompson, CRC Press, 1993.)

Preferably, the vector contains a selectable marker for identifying transformants. The selectable marker preferably confers a growth advantage under appropriate conditions. Generally, selectable markers are drug resistance genes, such as neomycin phosphotransferase. Other drug resistance genes are known to those in the art and may be readily substituted. Selectable markers for bacteria include, ampicillin resistance, tetracycline resistance, kanamycin resistance, chloramphenicol resistance, and the like. The selectable marker also preferably has a linked constitutive or inducible promoter and a termination sequence, including a polyadenylation signal sequence.

Additionally, a bacterial origin of replication and a selectable marker for bacteria are preferably included in the vector. Of the various origins (e.g., coleI, fd phage), a colEI origin of replication is preferred. Most preferred is the origin from the pUC plasmids, which allow high copy number.

The sequence of nucleotides encoding β-glucuronidase may also include a classical secretion signal, whereby the resulting peptide is a precursor protein processed and secreted. Suitable signal sequences of plant genes include, but are not limited to the signal sequences from glycine-rich protein and extensin. In addition, a glucuronide permease gene may be co-transfected either from the same vector containing microbial GUS or from a separate expression vector.

A general vector suitable for use in the present invention is based on pBI121 (U.S. Pat. No. 5,432,081) a derivative of pBIN19. Other vectors have been described (U.S. Pat. No. 4,536,475) or may be constructed based on the guidelines presented herein. The plasmid pBI121 contains a left and right border sequence for integration into a plant host chromosome and also contains a bacterial origin of replication and selectable marker. These border sequences flank two genes. One is a kanamycin resistance gene (neomycin phosphotransferase) driven by a nopaline synthase promoter and using a nopaline synthase polyadenylation site. The second is the *E. coli* GUS gene (reporter gene) under control of the CaMV 35S promoter and polyadenlyated using a nopaline synthase polyadenylation site. The *E. coli* GUS gene is replaced with a gene encoding a secreted form of β-glucuronidase. If appropriate, the CaMV 35S promoter is replaced by a different promoter. Either one of the expression units described above is additionally inserted or is inserted in place of the CaMV promoter and GUS gene.

Plants may be transformed by any of several methods. For example, plasmid DNA may be introduced by *Agrobacterium* co-cultivation or bombardment. Other transformation methods include electroporation, $CaPO_4$-mediated transfection, gene transfer to protoplasts, microinjection, and the like (see, *Gene Transfer to Plants*, Ed. Potrykus and Spangenberg, Springer, 1995, for procedures). Preferably, vector DNA is first transfected into *Agrobacterium* and subsequently introduced into plant cells. Most preferably, the infection is achieved by co-cultivation. In part, the choice of transformation methods depends upon the plant to be transformed. For example, monocots may be refractory to transformation by *Agrobacterium*. Tissues can alternatively be efficiently infected by *Agrobacterium* utilizing a projectile or bombardment method. Projectile methods are generally used for transforming sunflowers and soybean. Bombardment is used when naked DNA, typically *Agrobacterium* binary plasmids or pUC-based plasmids, is used for transformation or transient expression.

Briefly, co-cultivation is performed by first transforming *Agrobacterium* by freeze-thaw method (Holsters et al., *Mol. Gen. Genet.* 163: 181–187, 1978) or by other suitable methods (see, Ausubel, et al. supra; Sambrook et al., supra). A culture of *Agrobacterium* containing the plasmid is incubated with leaf disks, protoplasts or meristematic tissue to generate transformed plants (Bevan, *Nucl. Acids. Res.* 12:8711, 1984).

Briefly, for microprojectile bombardment, seeds are surface sterilized in bleach solution and rinsed with distilled water. Seeds are then imbibed in distilled water, and the cotyledons are broken off to produce a clean fracture at the plane of the embryonic axis. Explants are then bisected longitudinally between the primordial leaves and placed cut surface up on medium with growth regulating hormones, minerals and vitamin additives. Explants from other tissues or methods of preparation may alternatively be used. Explants are bombarded with gold or tungsten microprojectiles by a particle acceleration device. Freshly bombarded explants are placed in a suspension of transformed *Agrobacterium* transferred to medium with the cut surfaces down for 3 days with an 18 hr light cycle. Explants are transferred to medium lacking growth regulators but containing drug for selection and grown for 2–5 weeks. A positive selection system, such as using cellobiuronic acid and culture medium lacking a carbon source, is preferably used (see, co-pending application Ser. No. 09/130,695). After 1–2 weeks more without drug selection, leaf samples from green, drug-resistant shoots are grafted to in vitro grown rootstock and transferred to soil.

Activity of secreted GUS is assayed in whole plants or in selected tissues using a glucuronide substrate that is readily detected upon cleavage. Glucuronide substrates that are calorimetric are preferred. Field testing of plants may be performed by spraying a plant with the glucuronide substrate and observing color formation of the cleaved product.

Expression in Other Organisms

A variety of other organisms are suitable for use in the present invention. For example, various fungi, including yeasts, molds, and mushrooms, insects, especially vectors for diseases and pathogens, and other animals, such as cows, mice, goats, birds, aquatic animals (e.g., shrimp, turtles, fish, lobster and other crustaceans), amphibians and reptiles and the like, may be transformed with a GUS transgene.

The principles that guide vector construction for bacteria and plants, as discussed above, are applicable to vectors for these organisms. In general, vectors are well known and readily available. Briefly, the vector should have at least a promoter functional in the host in operative linkage with GUS. Usually, the vector will also have one or more selectable markers, an origin of replication, a polyadenylation signal and transcription terminator.

The sequence of nucleotides encoding β-glucuronidase may also include a classical secretion signal, whereby the resulting peptide is a precursor protein processed and secreted. Suitable secretion signals may be obtained from a variety of genes, such as mat-alpha or invertase genes. In addition, a permease gene may be co-transfected.

One of ordinary skill in the art will appreciate that a variety of techniques for producing transgenic animals exist. In this regard, the following U.S. patents teach such methodologies and are thus incorporated herein by reference: U.S. Pat. Nos. 5,162,215; 5,545,808; 5,741,957; 4,873,191; 5,780,009; 4,736,866; 5,567,607; and 5,633,076.

Uses of Microbial β-glucuronidase

As noted above, microbial β-glucuronidase may be used in a variety of applications. In general, microbial β-glucuronidase can be used as a reporter/effector molecule and as a diagnostic tool. As taught herein, microbial β-glucuronidase that is secretable is preferred as an in vivo reporter/effector molecule, whereas, in in vitro diagnostic applications, the biochemical characteristics of the β-glucuronidase disclosed herein (e.g., thermal stability, high turnover number) may provide preferred advantages.

Microbial-GUS, either secreted or non-secreted, can be used as a marker for transgenic constructions. In a certain embodiments, the transgenic host is a plant, such as rice, corn, wheat, or an aquatic animal. The transgenic GUS may be used in at least three ways: one in a method of positive selection, obviating the need for drug resistance selection, a second as a system to target molecules to specific cells, and a third as a means of detecting and tracking linked genes.

For positive selection, a host cell, (e.g., plant cells) is transformed with a GUS (preferably secretable GUS) transgene. Selection is achieved by providing the cells with a glucuronidated form of a required nutrient. For example, all cells require a carbon source, such as glucose. In one embodiment, glucose is provided as glucuronyl glucose (cellobiuronic acid), which is cleaved by GUS into glucose plus glucuronic acid. The glucose would then bind to receptors and be taken up by cells. The glucuronide may be any required compound, including without limitation, a cytokinin, auxin, vitamin, carbohydrate, nitrogen-containing compound, and the like. It will be appreciated that this positive selection method can be used for cells and tissues derived from diverse organisms, such as animal cells, insect cells, fungi, and the like. The choice of glucuronide will depend in part upon the requirements of the host cell.

As a marker/effector molecule, secreted GUS (s-GUS) is preferred because it is non-destructive, that is, the host does not need to be destroyed in order to assay enzyme activity. A non-destructive marker has special utility as a tool in plant breeding. The GUS enzyme can be used to detect and track linked endogenous or exogenously introduced genes. GUS may also be used to generate sentinel plants that serve as bioindicators of environmental status. Plant pathogen invasion can be monitored if GUS is under control of a pathogen promoter. In addition, such transgenic plants may serve as a model system for screening inhibitors of pathogen invasion. In this system, GUS is expressed if a pathogen invades. In the presence of an effective inhibitor, GUS activity will not be detectable. In certain embodiments, GUS is co-transfected with a gene encoding a glucuronide permease.

Preferred transgenes for introduction into plants encode proteins that affect fertility, including male sterility, female fecundity, and apomixis; plant protection genes, including proteins that confer resistance to diseases, bacteria, fungus, nematodes, viruses and insects; genes and proteins that affect developmental processes or confer new phenotypes, such as genes that control meristem development, timing of flowering, and the like.

Insect and disease resistance genes are well known. Some of these genes are present in the genome of plants and have been genetically identified. Others of these genes have been found in bacteria and are used to confer resistance.

Particularly well known insect resistance genes are the crystal genes of *Bacillus thuringiensis*. The crystal genes are active against various insects, such as lepidopterans, *Diptera, Hemiptera* and *Coleoptera*. Many of these genes have been cloned. For examples, see, GenBank Accession Nos. X96682, X96684; M76442, M90843, M89794, M22472, M37207, D17518, L32019, M97880, L32020, M64478, M11250, M13201, D00117, M73319, X17123, X86902, X06711, X13535, X54939, X54159, X13233, X54160, X56144, X58534, X59797, X75019, X62821, Z46442, U07642, U35780, U43605, U43606, U10985; U.S. Pat. Nos. 5,317,096; 5,254,799; 5,460,963; 5,308,760, 5,466,597, 5,2187,091, 5,382,429, 5,164,180, 5,206,166, 5,407,825, 4,918,066; PCT Applications WO 95/30753, WO 94/24264; AU 9062083; EP 408403 B1, EP 142924 B1, EP 256,553 B1, EP 192,741 B1; JP 62-56932;. Gene sequences for these and related proteins may be obtained by standard and routine technologies, such as probe hybridization of a *B. thuringiensis* library or amplification (see generally, Sambrook et al., supra, Ausubel et al. supra). The probes and primers may be synthesized based on publicly available sequence information.

Other resistance genes to *Sclerotinia*, cyst nematodes, tobacco mosaic virus, flax and crown rust, rice blast, powdery mildew, verticillum wilt, potato beetle, aphids, as well as other infections, are useful within the context of this invention. Examples of such disease resistance genes may be isolated from teachings in the following references: isolation of rust disease resistance gene from flax plants (WO 95/29238); isolation of the gene encoding Rps2 protein from *Arabidopsis thaliana* that confers disease resistance to pathogens carrying the avrRpt2 avirulence gene (WO 95/28478); isolation of a gene encoding a lectin-like protein of kidney bean confers insect resistance (JP 71-32092); isolation of the Hml disease resistance gene to *C. carbonum* from maize (WO 95/07989); for examples of other resistance genes, see WO 95/05743; U.S. Pat. No. 5,496,732; U.S. Pat. No. 5,349,126; EP 616035; EP 392225; WO 94/18335; JP 43-20631; EP 502719; WO 90/11770; U.S. Pat. No. 5,270,200; U.S. Pat. Nos. 5,218,104 and 5,306,863). In addition, general methods for identification and isolation of plant disease resistance genes are disclosed (WO 95/28423). Any of these gene sequences suitable for insertion in a vector according to the present invention may be obtained by standard recombinant technology techniques, such as probe hybridization or amplification. When amplification is performed, restriction sites suitable for cloning are preferably inserted. Nucleotide sequences for other transgenes, such as controlling male fertility, are found in U.S. Pat. No. 5,478,369, references therein, and Mariani et al., *Nature* 347:737, 1990.

In similar fashion, microbial GUS, preferably secreted, can be used to generate transgenic insects for tracking insect populations or facilitate the development of a bioassay for compounds that affect molecules critical for insect development (e.g., juvenile hormone). Secreted GUS may also serve as a marker for beneficial fungi destined for release into the environment. The non-destructive marker is useful for detecting persistence and competitive advantage of the released organisms.

In animal systems, secreted GUS may be used to achieve extracellular detoxification of glucuronides (e.g, toxin glucuronide) and examine conjugation patterns of glucuronides. Furthermore, as discussed above, secreted GUS may be used as a transgenic marker to track cells or as a positive selection system, or to assist in development of new bioactive GUS substrates that do not need to be transported across membrane. Aquatic animals are suitable hosts for GUS transgene. GUS may be used in these animals as a marker or effector molecule.

Within the context of this invention, GUS may also be used in a system to target molecules to cells. This system is particularly useful when the molecules are hydrophobic and thus, not readily delivered. These molecules can be useful as effectors (e.g., inducers) of responsive promoters. For example, molecules such as ecdysone are hydrophobic and not readily transported through phloem in plants. When ecdysone is glucuronidated it becomes amphipathic and can be delivered to cells by way of phloem. Targeting of compounds such as ecdysone-glucuronic acid to cells is accomplished by causing cells to express receptor for ecdysone. As ecdysone receptor is naturally only expressed in insect cells, however a host cell that is transgenic for ecdysone receptor will express it. The glucuronide containing ecdysone then binds only to cells expressing the receptor. If these cells also express GUS, ecdysone will be released from the glucuronide and able to induce expression from an ecdysone-responsive promoter. Plasmids containing ecdysone receptor genes and ecdysone responsive promoter can be obtained from Invitrogen (Carlsbad, Calif.). Other ligand-receptors suitable for use in this system include glucocorticoids/glucocorticoid receptor, estrogen/estrogen receptor and the like (see also U.S. Pat. Nos. 5,693,769 and 5,612,317).

In another aspect, purified microbial β-glucuronidase is used in medical applications. For these applications, secretion is not a necessary characteristic although it may be desirable a characteristic for production and purification. The biochemical attributes, such as increased stability and enzymatic activity disclosed herein are preferred characteristics. The microbial glucuronidase preferably has one or more of the disclosed characteristics.

For the majority of drug or pharmaceutical analysis, the compounds in urine, blood, saliva, or other bodily fluids are de-glucuronidated prior to analysis. Such a procedure is undertaken because compounds are often, if not nearly always, detoxified by glucuronidation in vertebrates. Thus, drugs that are in circulation and have passed through a site of glucuronidation (e.g., liver) are found conjugated to glucuronic acid. Such glucuronides yield a complex pattern upon analysis by, for example, HPLC. However, after the aglycone (drug) is cleaved from the glucuronic acid, a spectrum can be compared to a reference spectrum. Currently, *E. coli* GUS is utilized, but as shown herein, microbial GUS, e.g. *Bacillus* GUS has superior qualities.

The microbial GUS enzymes disclosed herein may be used in traditional medical diagnostic assays, such as described above for drug testing, pharmacokinetic studies, bioavailability studies, diagnosis of diseases and syndromes, following progression of disease or its response to therapy and the like (see U.S. Pat. Nos. 5,854,009, 4,450,239, 4,274,832, 4,473,640, 5,726,031, 4,939,264, 4,115,064, 4,892,833). These β-glucuronidase enzymes may be used in place of other traditional enzymes (e.g., alkaline phosphatase, horseradish peroxidase, beta-galactosidase, and the like) and compounds (e.g., green fluorescent protein, radionuclides) that serve as visualizing agents. Microbial GUS has qualities advantageous for use as a visualizing agent: it is highly specific for the substrate, water soluble and the substrates are stable. Thus, microbial GUS is suitable for use in Southern analysis of DNA, Northern analysis, ELISA, and the like.

In preferred embodiments, microbial GUS binds a hapten, either as a fusion protein with a partner protein that binds the hapten (e.g., avidin that binds biotin, antibody) or alone. If used alone, microbial GUS can be mutagenized and selected for hapten-binding abilities. Mutagenesis and binding assays are well known in the art. In addition, microbial GUS can be conjugated to avidin, streptavidin, antibody or other hapten binding protein and used as a reporter in the myriad assays that currently employ enzyme-linked binding proteins. Such assays include immunoassays, Western blots, in situ hybridizations, HPLC, high-throughput binding assays, and the like (see, for examples, U.S. Pat. Nos. 5,328,985 and 4,839,293, which teach avidin and streptavidin fusion proteins and U.S. Pat. No. 4,298,685, Diamandis and Christopoulos, *Clin. Chem.* 37:625, 1991; Richards, *Methods Enzymol.* 184:3, 1990; Wilchek and Bayer, *Methods Enzymol.* 184:467, 1990; Wilchek and Bayer, *Methods Enzymol.* 184:5, 1990; Wilchek and Bayer, *Methods Enzymol.* 184:14, 1990; Dunn, *Methods Mol. Biol.* 32:227, 1994; Bloch, *J. Hitochem. Cytochem.* 41:1751, 1993; Bayer and Wilchek *J. Chromatogr.* 510:3, 1990, which teach various applications of enzyme-linked technologies and methods).

Microbial GUSes can also be used in therapeutic methods. By glucuronidating compounds such as drugs, the compound is inactivated. When a glucuronidase is expressed or targeted to the site for delivery, the glucuronide is cleaved and the compound delivered. For these purposes, GUS may be expressed as a transgene or delivered, for example, coupled to an antibody specific for the target cell (see e.g., U.S. Pat. Nos. 5,075,340, 4,584,368, 4,481,195, 4,478,936, 5,760,008, 5,639,737, 4,588,686).

The present invention also provides kits comprising microbial GUS protein or expression vectors containing microbial GUS gene. One exemplary type of kit is a dipstick test. Such tests are widely utilized for establishing pregnancy, as well as other conditions. Generally, these dipstick tests assay the glucuronide form, but it would be advantageous to use reagents that detect the aglycone form. Thus, GUS may be immobilized on the dipstick adjacent to or mixed in with the detector molecule (e.g., antibody). The dipstick is then dipped in the test fluid (e.g., urine) and as the compounds flow past GUS, they are cleaved into aglycone and glucuronic acid. The aglycone is then detected. Such a setup may be extremely useful for testing compounds that are not readily detectable as glucuronides.

In a variation of this method, the microbial GUS enzyme is engineered to bind a glucuronide but lacks enzymatic activity. The enzyme will then bind the glucuronide and the enzyme is detected by standard methodology. Alternatively, GUS is fused to a second protein, either as a fusion protein or as a chemical conjugate, that binds the aglycone. The fusion is incubated with the test substance and an indicator substrate is added. This procedure may be used for ELISA, Northern, Southern analysis and the like.

The following examples are offered by way of illustration, and not by way of limitation.

EXAMPLES

Example 1

Identification of Microbes that Express β-glucuronidase

Skin microbes are obtained using cotton swabs immersed in 0.1% Triton® X-100 and rubbing individual arm pits or by dripping the solution directly into arm pits and recovering it with a pipette. Seven individuals are sampled. Dilutions (1:100, 1:1000) of arm pit swabs are plated on 0.1×and 0.5× TSB (Tryptone Soy Broth, Difco) agar containing 50 μg/mL X-GlcA (5-bromo-4-chloro-3-indolyl β-D-glucuronide), an indicator substrate for β-glucuronidase. This substrate gives a blue precipitate at the site of enzyme activity (see U.S. Pat. No. 5,268,463). TSB is a rich medium which promotes growth of a wide range of microorganisms. Plates are incubated at 37° C.

Soil samples (ca. 1 g) are obtained from an area in Canberra, ACT, Australia (10 samples) and from Queanbeyan, NSW, Australia (12 samples). Although only one of the ten samples from Canberra is intentionally taken from an area of pigeon excrement, most isolates displaying β-glucuronidase activity are in the genera *Enterobacter* or *Salmonella*. Soil samples are shaken in 1–2 mL of water; dilutions of the supernatant are treated as for skin samples, except that incubation is at 30° C. and 1.0×TSB plates are used rather than diluted TSB. Some bacteria lose vitality if maintained on diluted medium, although the use of full-strength TSB usually delays, but does not prevent, the onset of indigo from X-GlcA hydrolysis.

Microbes that secrete β-glucuronidase have a strong, diffuse staining pattern (halo) surrounding the colony. The appearance of blue colonies varies in time, from one to several days. Under these conditions (aerobic atmosphere and rich medium) many microorganisms grow. Of these, approximately 0.1–1% display β-glucuronidase phenotype, with the secretory phenotype being less common than the non-secretory phenotype.

Colonies that exhibit a strong, diffuse staining pattern are selected for further purification, which consists of two or more restreaking of those colonies. Occasionally segregation of color production can be observed after the purification procedure. In Table 1 below, a summary of the findings is presented. Some strains are listed as GUS secretion-negative because a later repetition of the halo test was negative, showing that the phenotype can vary, possibly because of growth conditions.

Phylogenetic Analysis

1 For phylogenetic identification of the microbes, a variable region of 16S rDNA is amplified using primers, P3-16SrDNA and P4-16SrDNA (see Table 2), derived from two conserved regions within stem-loop structures of the rRNA. The amplified region corresponds to nucleotides 361 to 705 of *E coli* rRNA, including the primers. Amplification conditions for 16S rDNA are 94° C. for 2 min; followed by 35 cycles of 94° C. for 20 sec, 48° C. for 40 sec, 72° C. for 1.5 min; followed by incubation at 72° C. for 5 min.

2 Amplified fragments are separated by electrophoresis on TAE agarose gels (approximately 1.2%), excised and extracted by freeze-fracture and phenol treatment. Fragments are further purified using Qiagen (Clifton Hill, Vic, Australia) silica-based membranes in microcentrifuge tubes. Purified DNA fragments are sequenced using the amplification primers in combination with BigDye™ Primer Cycle Sequencing Kit from Perkin-Elmer ABI (fluorescent dye termal cycling sequencing) (Foster City, Calif.). Cycling conditions for DNA sequence reactions are: 2 min at 94° C., followed by 30 cycles of 94° C. for 30 sec, 50° C. for 15 sec, and 60° C. for 2 min. A 10 μL reaction uses 41 μL of BigDye™ Terminator mix, 1 μL of 10 μM primer, and 200–500 ng of DNA. The reaction products are precipitated with ethanol or iso-propanol, resuspended and subjected to gel separation and nucleotide analysis.

3 The ribosomal sequences are aligned and assigned to phylogenetic placement using the facilities of the Ribosomal Database Project of Michigan State University (rdpwww.life.uiuc.edu which now contains more than 10,000 16S rRNA sequences (Maidak et al., *Nucl. Acids Res.* 27:171–173; 1999). Phylogenetic placement is used to select strains for further study.

TABLE 1

| STRAIN | GUS Secretion | GUS Amplif. | GENUS[^] |
|---|---|---|---|
| SKIN | | | |
| EH2 | + | yes | *Staphylococcus warneri* |
| EH4 | + | yes | *Staphylococcus warneri* |
| EH4-110A | − | yes | *Staphylococcus warneri* |
| LS-B | + | yes | *Staphylococcus haemophilus*/ homini |
| PG3A | + | no | *Staphylococcus homini*/warneri |
| SH1B | + | no | *Staphylococcus warneri*/aureus |
| SH1C | + | yes | *Staphylococcus warneri*/aureus |
| CRA1 | + | no | *Staphylococcus warneri* |
| CRA2 | + | no | *Staphylococcus warneri* |
| CANBERRA SOIL | | | |
| CSW1a | − | yes | Enterobacter/Salmonella |
| CSW1b | | yes | Enterobacter/Salmonella |
| CDS1 | + | no | Enterobacter/Salmonella |
| CBP1 | − | yes | Salmonella |
| CS2.1 | − | no | Enterobacter/Salmonella |
| CS2.3 | − | no | Enterobacter/Salmonella |
| QUEANBEYAN SOIL | | | |
| Q1.2 | − | yes | Pseudomonas/Azospirilium |
| Q1.3 | + | no | Pseudomonas |
| Q2VD3 | − | yes | Pseudomonas/Azospirilium |
| Q2VD6 | − | yes | Salmonella |
| Q2VD7 | − | yes | Clavibacter |
| Q3WR2 | + | no | Flavobacter/Planococcus |
| Q3WR6 | + | yes | Pseudomonas |
| Q4DS1 | − | no | Arthrobacter |
| QRM1 | − | no | Arthrobacter |
| QRM2 | − | no | Arthrobacter |
| QRM6 | − | no | Pseudomonas |
| QTCR3 | + | no | Arthrobacter |

[^]where two genera or species are listed, the rRNA analysis is inconclusive

As can be observed from the table above, all GUS expressing skin isolates belong to the genus *Staphylococcus* and to a limited number of species, *Staphylococcus warneri* and *Staphylococcus homini* or *haemophilus*. The Canberra soil samples all belonged to the genera *Salmonella* or *Enterobacter/Salmonella*. In contrast, a higher degree of microbial diversity was found in the Queanbeyan strains.

The presence of GUS genes is established by amplification using degenerate oligonucleotides derived from a conserved region of the GUS gene. A pair of oligonucleotides is designed using an alignment of *E. coli* gusA and human GUS sequences. The primer T3-GUS-2F covers *E. coli* GUS amino acids 163–168 (DFFNYA) (SEQ ID NO: 31), while T7-GUS-5B covers the complementary sequence to amino acids 549–153 (WNFAD) (SEQ ID NO: 32). The full length of *E. coli* GUS is 603 amino acids. As shown in Table 1, amplification is not always successful, likely due to mismatching of the primers with template. Thus, a negative amplification does not necessarily signify that the microorganism lacks a GUS gene.

Example 2

Cloning of GUS Genes by Genetic Complementation

Genomic DNA of several candidate strains is isolated and digested with one of the following enzymes, EcoR I, BamH I, Hind III, Pst I. Digested DNA fragments are ligated into the corresponding site of plasmid vector pBluescript II SK (+), and the ligation mix is electroporated into *E. coli* KW1, which is a strain deleted for the complete GUS operon. Colonies are plated on LB-X-GlcA plates and assayed for blue color. Halo formation is not used as a criterium, because behavior of the GUS gene in a different genetic background is unknown. In general though, halo formation is obtained in KW1.

Isolated plasmids from GUS+transformants are retransformed into KW1 and also into DH5α to demonstrate that the GUS gene is contained within the construct. In all cases, retransformant colonies stained blue with X-GIcA.

Example 3

DNA Sequence Analysis of GUS Genes Isolated by Complementation

1 DNA sequence is determined for the isolates that amplified from the primers T3 and T7, which flank the pBS polylinker. Cyclic thermal sequencing was done as above, except that elongation time is increased to 4 min to allow for longer sequence determinations.

2 The sequence information is used to design new oligonucleotides to obtain the full-length sequence of the clones.

3 DNA sequences are obtained for GUS genes from seven different genera: *Bacillus* (see, Example 4), *Enterobacter/Salmonella, Pseudomonas, Salmonella, Staphylococcus*, and *Thermotga* (see, TIGR database at www.tigr.org) (FIGS. 4A–J). Predicted amino acids translations are presented in FIGS. 3A–B. In addition to the biochemical analysis and amplification using GUS primers, confirmation that the isolates contain GUS gene is obtained from the DNA and amino acid sequences. Amino acid alignment of *Bacillus* GUS with human (HGUS) and *E. coli* (EGUS) reveal extensive sequence identity and similarity. Likewise, alignment using ClustalW program of *Bacillus, Staphylococcus homini, Staphylococcus warneri, Thermotoga maritima, Enterobacter/Salmonella* and *E. coli* show considerable amino acid identity and conservation (FIG. 5B). The darker the shading, the higher the conservation among all GUSes. As seen in FIG. 5B, the region containing the critical catalytic residue (E344 using *Bacillus* numbering) is highly conserved. This region extends over amino acids ca. 250-ca. 360 and ca. 400-ca. 535. Within these regions there are pockets of nearly complete identity among six sequences. When constructing variants, in general, the regions of highest identity are not altered.

Two additional sequences from *Salmonella* and *Pseudomonas* are presented in nucleotide alignment with *Bacillus*. Significant sequence identity among the three sequences indicates that the *Salmonella* and *Pseudomonas* sequences are β-glucuronidase coding sequences.

TABLE 2

| PRIMER | BASES | SEQUENCE | SEQ ID NO. |
|---|---|---|---|
| T3-GUS-2F | 36 | AAT TAA CCC TCA CTA AAC GG/A YTT YTT YAA YTA YGC | |
| T7-GUS-5B | 39 | GTA ATA CGA CTC ACT ATA GGG/GAA RTC IGC RAA RTT CCA | |
| CSW-RTSHY(F) | 17 | ATC GCA CGT CCC ACT AC | |
| CSW-RTSHY(R) | 18 | CGT GCG ATA GGA GTT AGC | |
| EH-FRTSHY(F) | 22 | ATT TAG AAC ATC TCA TTA TCC C | |
| EH-FRTSHY(R) | 23 | TGA GAT GTT CTA AAT GAA TTA GC | |
| LSB-KRPVT(R) | 17 | ATC GTG ACC GGA CGC TT | |
| CBP-QAYDE | 17 | GCG CGT AAT CTT CCT GG | |
| NG-RP1L | 18 | TAG C(GA)C CTT CGC TTT CGG | |
| NG-RP1R | 20 | ATC ATG TTT ACA GAG TAT GG | |
| P3-16SrDNA | 21 | GGA ATA TTG CAC AAT GGG CGC | |
| P4-16SrDNA | 23 | GAT CTC TAC GCA TTT CAC CGC TA | |
| Tm-MVRPQRN | 17 | ATG GTA AGA CCG CAA CG | |
| Tm-Nco-MVRPQRN | 25 | TAA AAA CCA TGG TAA GAC CGC AAC G | |
| Tm-RRLWSE(R) | 20 | CCT CAC TCC ACA GTC TTC TC | |
| Tm-RRL WSE(R)-Nhe | 30 | AGA CCG CTA GCC TCA CTC CAC AGT CTT CTC | |
| Ps-FDFFNYA(F) | 22 | TTT GAC TTT TTC AAC TAT GCA G | |
| Ps-DFFNYA(R) | 23 | AAT TCT GCA TAG TTG AAA AAG TC | |

Example 4

Isolation of a Gene From *Bacillus* Encoding a Secreted β-glucuronidase

Soil samples are placed in broth and plated for growth of bacterial colonies on agar plates containing 50 μg/mL X-GlcA. Bacteria that secrete β-glucuronidase have a strong, diffuse staining pattern surrounding the colony.

One bacterial colony that exhibited this type of staining pattern is chosen bacterium is identified as a *Bacillus* based on amplification of 16S rRNA, and is most likely in the *Bacillus pseudomegaterium* group. Oligonucleotide sequences derived from areas exhibiting a high degree of similarity between *E. coli* and human β-glucuronidases are used in amplification reactions on *Bacillus* and *E. coli* DNA. A fragment is observed using *Bacillus* DNA, which is the same size as the *E. coli* fragment.

*Bacillus* DNA is digested with Hind III and ligated to Hind III-digested pBSII-KS plasmid vector. The recombinant plasmid is transfected into KW1, an *E. coli* strain that is deleted for the GUS operon. Cells are plated on X-GlcA plates, and one colony exhibited strong, diffuse staining pattern, suggesting that this clone encoded a secreted β-glucuronidase enzyme. The plasmid, pRAJa17.1, is isolated and subjected to analysis.

The DNA sequence of part of the insert of pRAJa17.1 is shown in FIG. 1. A schematic of the 6029 bp fragment is shown in FIG. 2. The fragment contains four large open reading frames. The open reading frame proposed as *Bacillus* GUS (BoGUS) begins at nucleotide 162 and extends to 1907 (FIG. 1). The predicted translate is shown in FIG. 3A and its alignment with *E. coli* and human β-glucuronidase is presented in FIG. 5A. BoGUS is 47.2% identical to *E. coli* GUS, which is about the same identity as human GUS and *E. coli* GUS (49.1%). Thus, GUS from *Bacillus* is about as related to another bacterium as to human. One striking difference in sequence among the proteins is the number of cysteine residues. Whereas, both human and *E. coli* GUS have 4 and 9 cysteines, respectively, BoGUS has only one cysteine.

The secreted GUS protein is 602 amino acids long and does not appear to have a canonical leader peptide. A prototypic leader sequence has an amino-terminal positively charged region, a central hydrophobic region, and a more polar carboxy-terminal region (see, von Heijne, *J. Membrane Biol.* 115:195–201, 1990) and is generally about 20 amino acids long. However, in both mammalian and bacterial cells, proteins without canonical or identifiable secretory sequences have been found in extracellular or periplasmic spaces.

Example 5

Properties of Secreted β-glucuronidase

Figure 6:
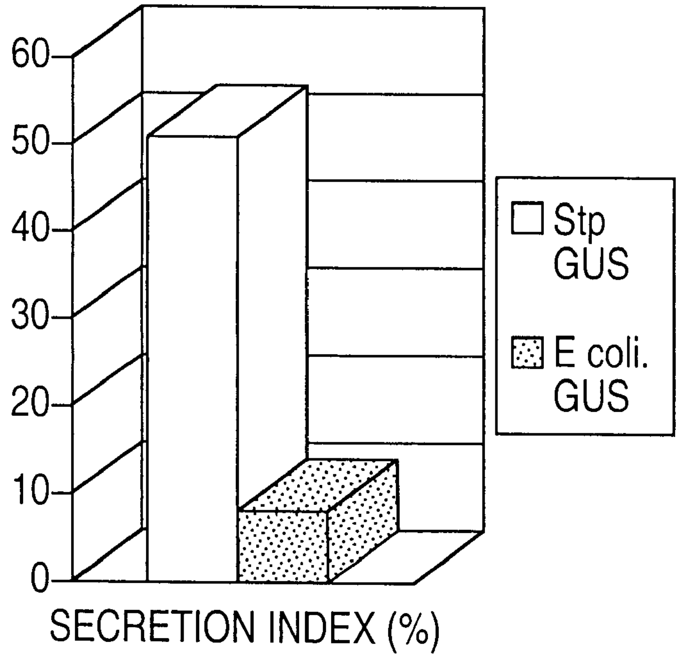
FIG. 6 is a graph showing that *Bacillus* GUS is secreted in *E. coli* transformed with an expression vector encoding *Bacillus* GUS. The secretion index is the percent of total activity in periplasm less the percent of total β-galactosidase activity in periplasm.

Although the screen described above suggests that the *Bacillus* GUS is secreted, the cellular localization of BoGUS is further examined. Cellular fractions (e.g., periplasm, spheroplast, supernatant, etc.) are prepared from KW1 cells transformed with pRAJa17.1 or a subfragment that contains the GUS gene and from *E. coli* cells that express β-glucuronidase. GUS activity and β-galactosidase (β-gal) activity is determined for each fraction. The percent of total activity in the periplasm fraction for GUS and β-gal (a non-secreted protein) are calculated; the amount of β-gal activity is considered background and thus is subtracted from the amount of β-glucuronidase activity. In FIG. 6, the relative activities of BoGUS and *E. coli* GUS in the periplasm fraction are plotted. As shown, approximately 50% of BoGUS activity is found in the periplasm, whereas less than 10% of *E. coli* GUS activity is present.

The thermal stability of BoGUS and *E. coli* GUS enzymes are determined at 65° C., using a substrate that can be measured by spectrophotometry, for example. One such substrate is p-nitrophenyl β-D-glucuronide (pNPG), which when cleaved by GUS releases the chromophore p-nitrophenol. At a pH greater than its pKa (approximately 7.15), the ionized chromophore absorbs light at 400–420 nm, therefore appears in the yellow range of visible light. Briefly, reactions are performed in 50 mM $Na_3PO_4$ pH 7.0, 10 mM 2-ME, 1 mM EDTA, 1 mM pNPG, and 0.1% Triton® X-100 at 37° C. The reactions are terminated by the addition of 0.4 ml of 2-amino-2-methylpropanediol, and absorbance measured at 415 nm against a substrate blank. Under these conditions, the molar extinction coefficient of p-nitrophenol is assumed to be 14,000. One unit is defined as the amount of enzyme that produces 1 nmole of product/min at 37° C.

Figure 7:
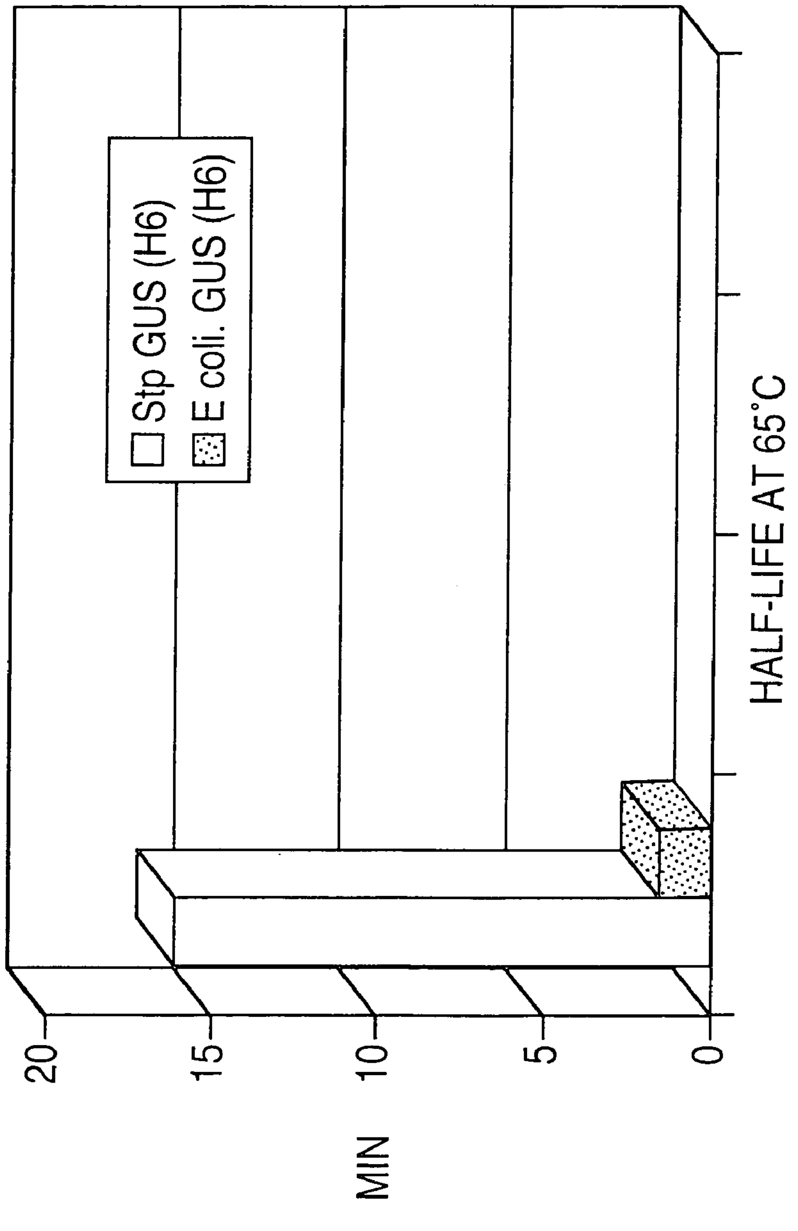
FIG. 7 is a graph illustrating the half-life of *Bacillus* GUS and *E. coli* GUS at 65° C.

As shown in FIG. 7, BoGUS has a half-life of approximately 16 min, while *E. coli* GUS has a half-life of less than 2 min. Thus, BoGUS is at least 8 times more stable than the *E. coli* GUS. In addition, the catalytic properties of BoGUS are substantially better than the *E. coli* enzyme: The Km is half and the Vmax is 2.5 times greater.

TABLE 3

| | BoGUS | *E. coli* GUS |
|---|---|---|
| Km | 70 μM pNPG | 150 μM pNPG |
| Vmax | 90 nmoles/min/μg | 35 nmoles/min/μg |

Figure 8:
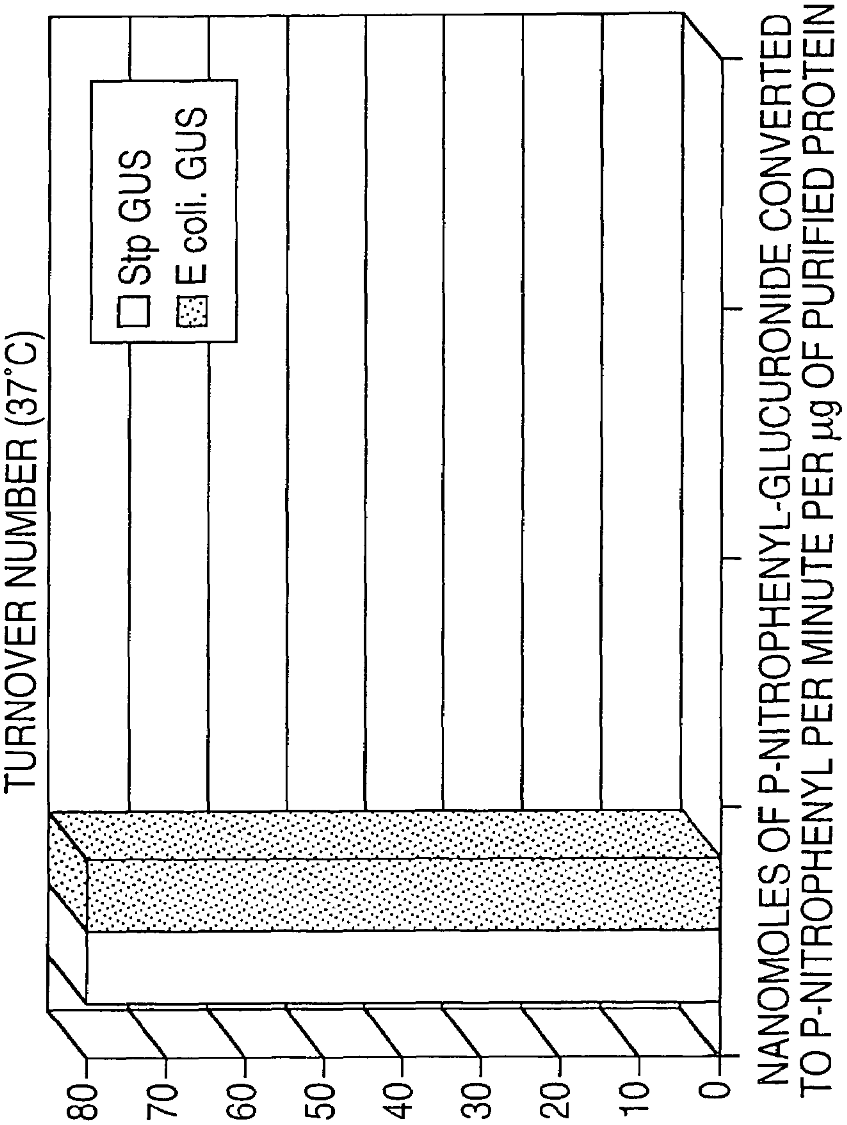
FIG. 8 is a graph showing the turnover number of *Bacillus* GUS and *E. coli* GUS enzymes at 37° C.
Figure 9:
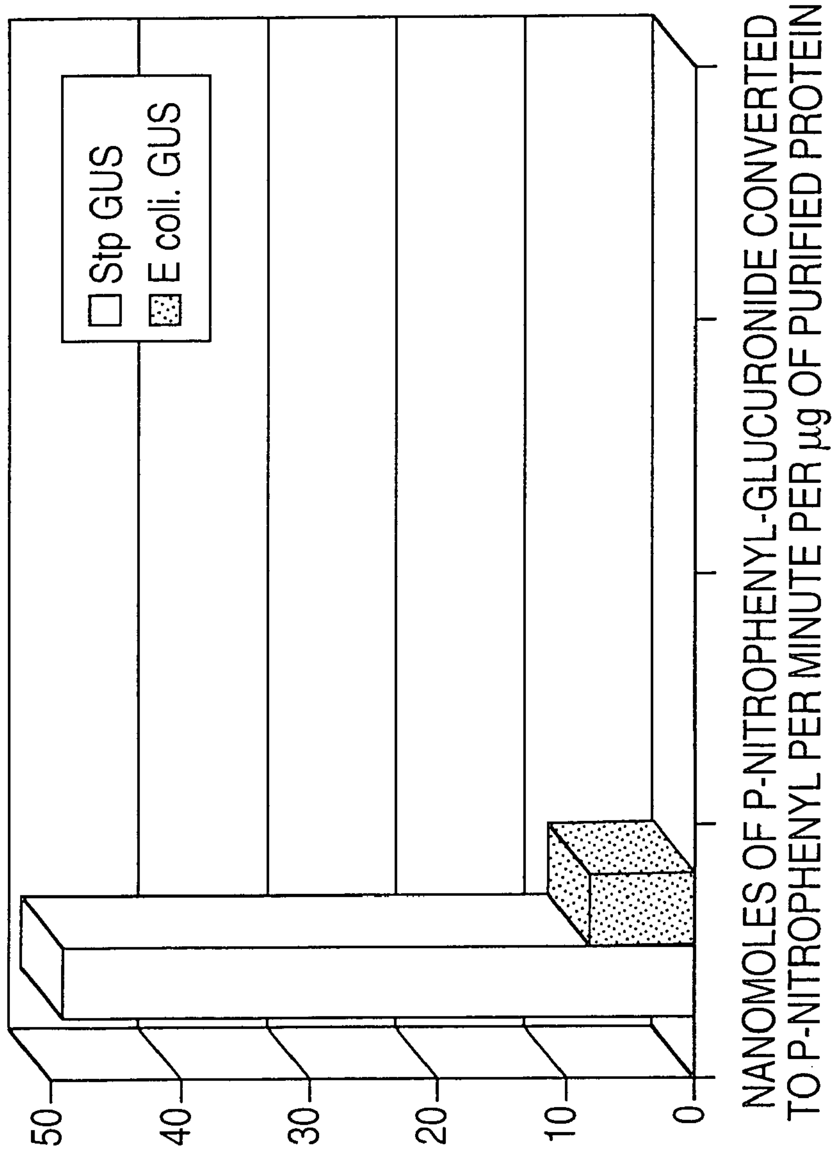
FIG. 9 is a graph showing the turnover number of *Bacillus* GUS and *E. coli* GUS enzymes at room temperature.

The turnover number of BoGUS is 2.5 to 5 times higher than *E. coli* GUS at either 37° C. or at room temperature (FIGS. 8 and 9). A turnover number is calculated as nmoles of pNPG converted to p-nitrophenol per min per μg of purified protein.

Figure 10:
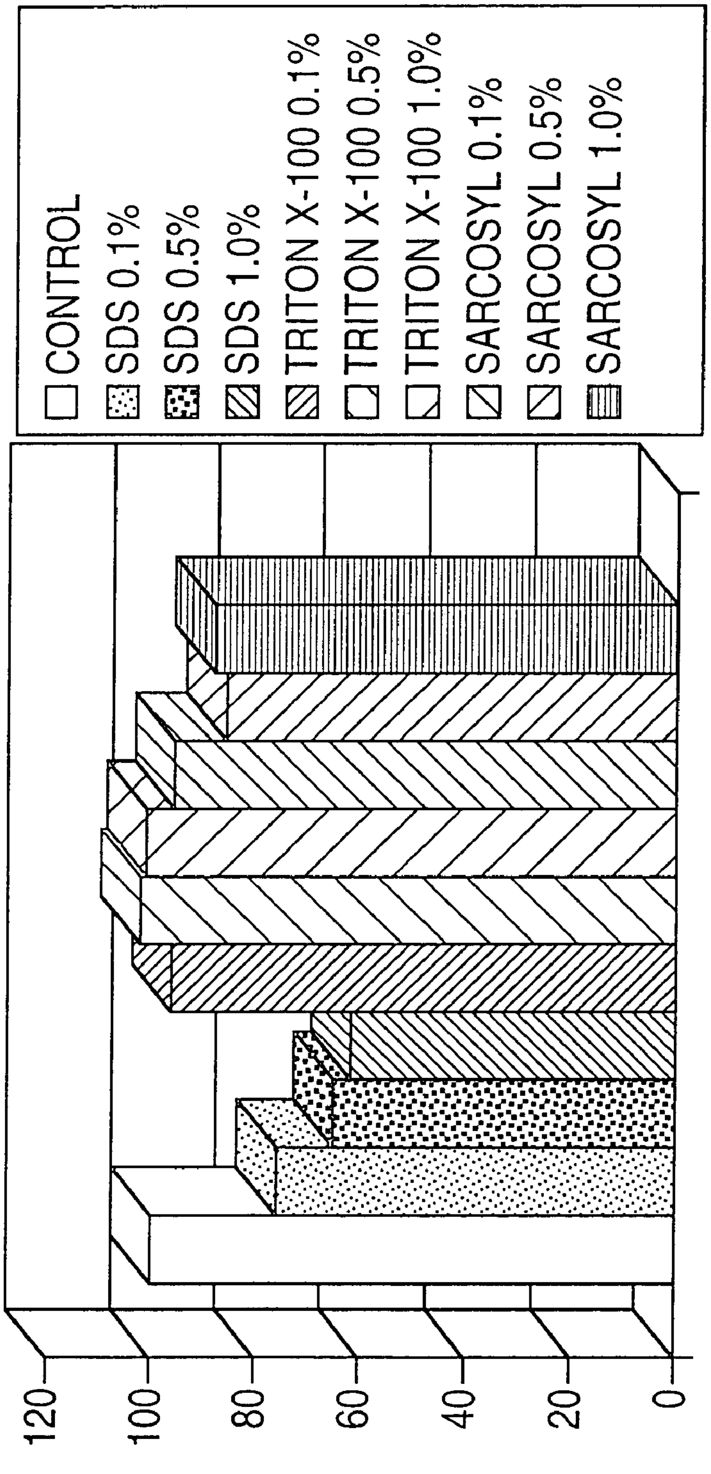
FIG. 10 is a graph presenting relative enzyme activity of *Bacillus* GUS in various detergents.
Figure 11:
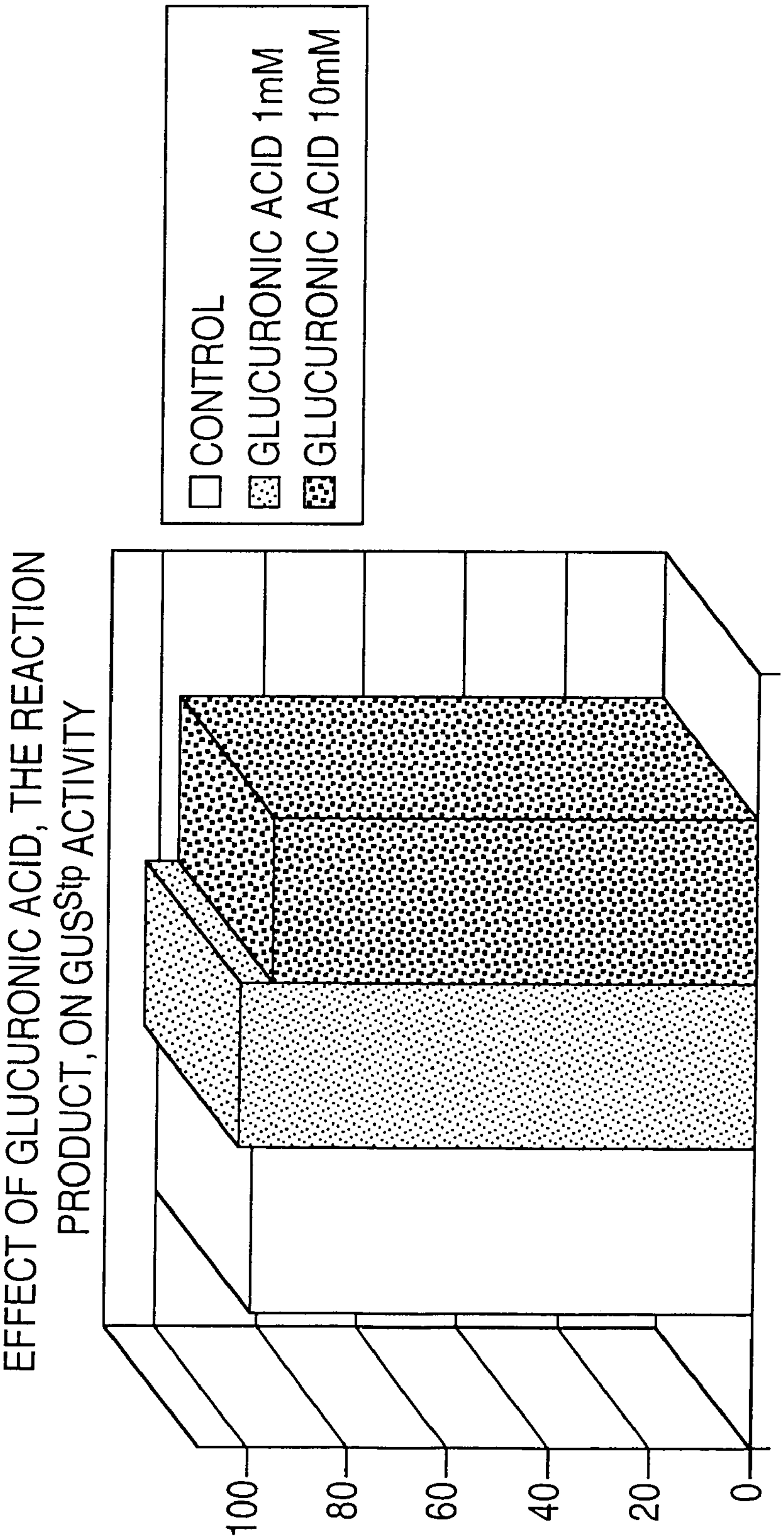
FIG. 11 is a graph presenting relative enzyme activity of *Bacillus* GUS in the presence of glucuronic acid.
Figure 12:
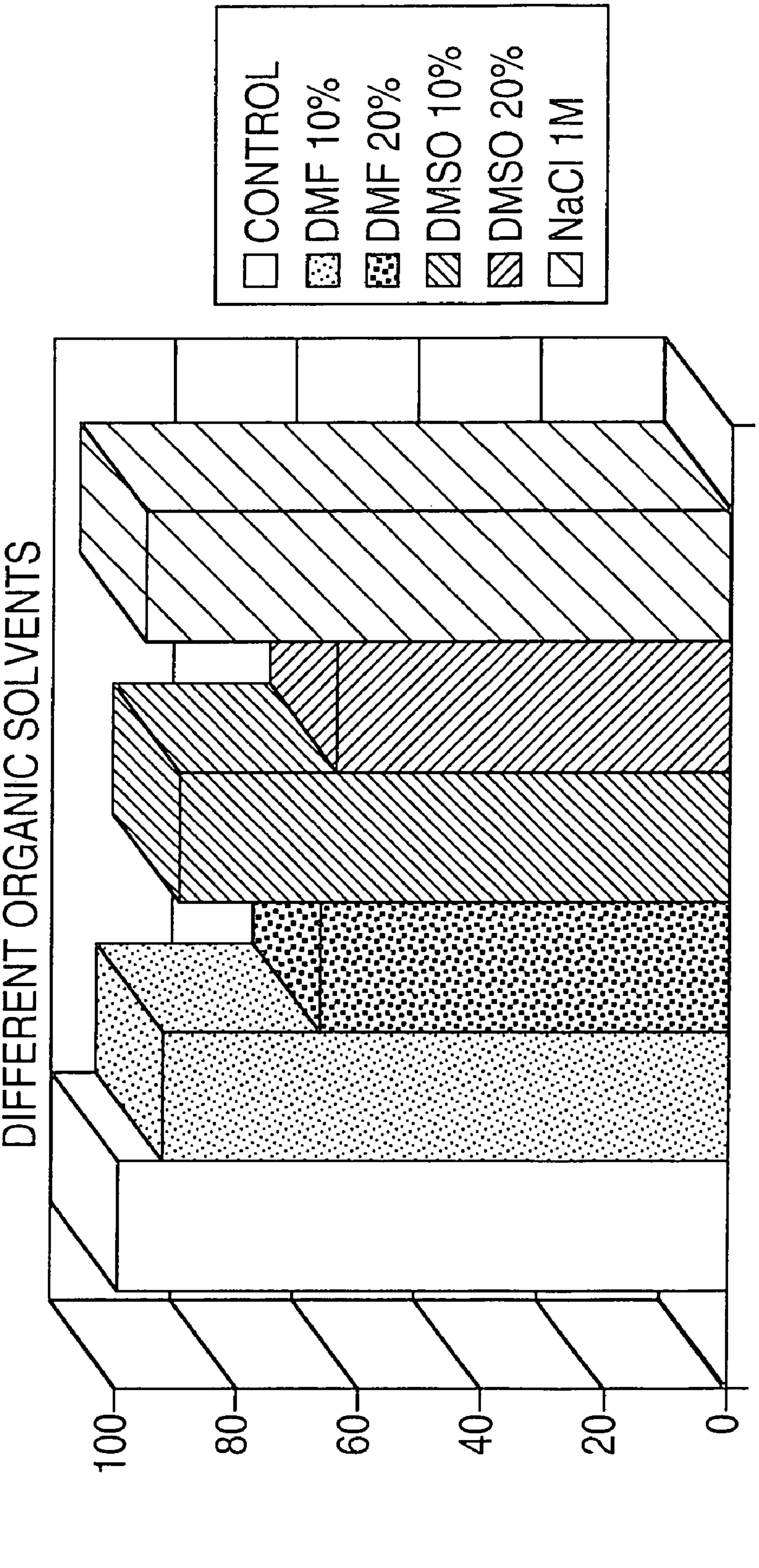
FIG. 12 is a graph presenting relative enzyme activity of *Bacillus* GUS in various organic solvents and in salt.

BoGUS enzyme activity is also resistant to inhibition by detergents. Enzyme activity assays are measured in the presence of varying amounts of SDS, Triton® X-100, or sarcosyl. As presented in FIG. 10, BoGUS was not inhibited or only slightly inhibited (<20% inhibition) in Tritong X-100 and Sarcosyl. In SDS, the enzyme still had substantial activity (60–75% activity). In addition, BoGUS is not inhibited by the end product of the reaction. Activity is determined normally or in the presence of 1 or 10 mM glucuronic acid. No inhibition is seen at either 1 or 10 mM glucuronic acid (FIG. 11). The enzyme is also assayed in the presence of organic solvents, dimethylformamide (DMF) and dimethylsulfoxide (DMSO), and high concentrations of NaCl (FIG. 12). Only at the highest concentrations of DMF and DMSO (20%) does BoGUS demonstrate inhibition, approximately 40% inhibited. In lesser concentrations of organic solvent and in the presence of 1 M NaCl, BoGUS retains essentially complete activity.

The *Bacillus* β-glucuronidase is secreted in *E. coli* when introduced in an expression plasmid as evidenced by approximately half of the enzyme activity being detected in the periplasm. In contrast, less than 10% of *E. coli* β-glucuronidase is found in periplasm. Secreted microbial GUS is also more stable than *E. coli* GUS (FIG. 7), has a higher turnover number at both 37° C. and room temperature (FIGS. 8 and 9), and unlike *E. coli* GUS, it is not substantially inhibited by detergents (FIG. 10) or by glucuronic acid (FIG. 11) and retains activity in high salt conditions and organic solvents (FIG. 12).

As shown herein, multiple mutations at residues Val 128, Leu 141, Tyr 204 and Thr 560 (FIGS. 3A–B) result in a non-functional enzyme. Thus, at least one of these amino acids is critical to maintaining enzyme activity. A mutein *Bacillus* GUS containing the amino acid alterations of Val 128→Ala, Leu 141→His, Tyr 204→Asp and Thr 560→Ala is constructed and exhibits little enzymatic activity. As shown herein, the residue alteration that most directly affected activity is Leu 141. In addition, three residues have been identified as likely contact residues important for catalysis in human GUS (residues Glu 451, Glu 540, and Tyr 504) (Jain et al., *Nature Struct. Biol.* 3: 375, 1996). Based on alignment with *Bacillus* GUS, the corresponding residues are Glu 415, Glu 508, and Tyr 471. By analogy with human GUS, Asp 165 may also be close to the reaction center and likely forms a salt bridge with Arg 566. Thus, in embodiments where it is desirable to retain enzymatic activity of GUS, the residues corresponding to Leu 141, Glu 415, Glu 508, Tyr 471, Asp 165, and Arg 566 in *Bacillus* GUS are preferably unaltered.

Example 6

Construction of a Codon Optimized Secreted β-glucuronidase

The *Bacillus* GUS gene is codon-optimized for expression in *E. coli* and in rice. Codon frequencies for each codon are determined by back translation using ecohigh codons for highly expressed genes of enteric bacteria. These ecohigh codon usages are available from GCG. The most frequently used codon for each amino acid is then chosen for synthesis. In addition, the polyadenylation signal, AATAAA, splice consensus sequences, ATTTA AGGT, and restriction sites that are found in polylinkers are eliminated. Other changes may be made to reduce potential secondary structure. To facilitate cloning in various vectors, four different 5' ends are synthesized: the first, called A0 (GT CGA CCCATGGT AGATCTG ACT AGT CTG TAC CCG) (SEQ ID NO: 51) uses a sequence (continuation of AMD-B10) comprising an Nco I (underlined), Bgl II (double underlined), and Spe I (italicized) sites. The Leu (CTG) codon is at amino acid 2 in FIGS. 3A–B. The second variant, called AI (GTC GAC AGG AGT GCT ATC ATG CTG TAC CCG), adds the native Shine/Dalgarno sequence 5' of the initiator Met (ATG) codon; the third, called AII, (GTC GAC AGG AGT GCT A CCATGGTG TAC CCG) adds a modified Shine/Dalgarno sequence 5' of the initiator Met codon such that a Nco I site is added; the fourth one, called AIII (GTC GAC AGG AGT GCT ACCATGGTA GAT CTG TAC CCG) adds a modified Shine/Dalgarno sequence 5' of the Leu (CTG) codon (residue 2) and Nco I and BgI II sites. All of these new 5' sequences contain a SaI I site at the extreme 5' end to facilitate construction and cloning. In certain embodiments, to facilitate protein purification, a sequence comprising a Nhe I, PmI I, and BstE II sites (underlined) and encoding hexa-His amino acids joined at the 3' (COOH-terminus) of the gene. (original)

GCTAGCCATCACCATCACCATCACGTGTGAATT GGTGACCG SerSerHisHisHisHisHisHisVal *

Figure 14:
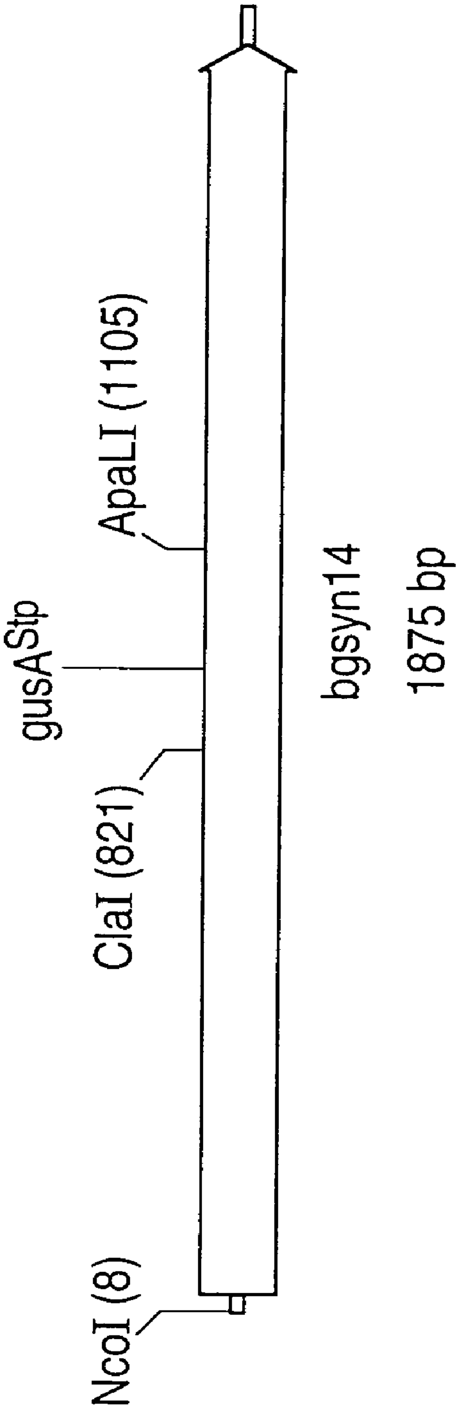
FIG. 14 is a schematic of the DNA sequence of *Bacillus* GUS that is codon-optimized for production in *E. coli.*

Nucleotide and amino acid sequences of one engineered secretable microbial GUS are shown in FIGS. 13A–C, and a schematic is shown in FIG. 14. The coding sequence for this protein is assembled in pieces. The sequence is dissected into four fragments, A (bases 1–457); B (bases 458–1012); C (bases 1013–1501); and D (bases 1502–1875). Oligonucleotides (Table 4) that are roughly 80 bases (range 36–100 bases) are synthesized to overlap and create each fragment. The fragments are each cloned separately and the DNA sequence verified. Then, the four fragments are excised and assembled in pLITMUS 39 (New England Biolabs, Beverley, Mass.), which is a small, high copy number cloning plasmid.

TABLE 4

| Oligonucleotide | Size | Sequence | SEQ ID NO |
|---|---|---|---|
| BoGUS A-1-80T | 80 | TCGACCCATGGTAGATCTGACTAGTCTGTACCCGATCAACAC CGAGACCCGTGGCGTCTTCGACCTCAATGGCGTCTGGA | |
| BoGUS A-121-200B | 80 | GGATTTCCTTGGTCACGCCAATGTCATTGTAACTGCTTGGGA CGGCCATACTAATAGTGTCGGTCAGCTTGCTTTCGTAC | |
| BoGUS A-161-240T | 80 | CCAAGCAGTTACAATGACATTGGCGTGACCAAGGAAATCCGC AACCATATCGGATATGTCTGGTACGAACGTGAGTTCAC | |
| BoGUS A-201-280B | 80 | GCGGAGCACGATACGCTGATCCTTCAGATAGGCCGGCACCGT GAACTCACGTTCGTACCAGACATATCCGATATGGTTGC | |
| BoGUS A-241-320T | 80 | GGTGCCGGCCTATCTGAAGGATCAGCGTATCGTGCTCCGCTT CGGCTCTGCAACTCACAAAGCAATTGTCTATGTCAATG | |
| BoGUS A-281-360B | 80 | AATGGCAGGAATCCGCCCTTGTGCTCCACGACCAGCTCACCA TTGACATAGACAATTGCTTTGTGAGTTGCAGAGCCGAA | |
| BoGUS A-321-400T | 80 | GTGAGCTGGTCGTGGAGCACAAGGGCGGATTCCTGCCATTCG AAGCGGAAATCAACAACTCGCTGCGTGATGGCATGAAT | |
| BoGUS A-361-460B | 100 | GTACAGCCCCACCGGTAGGGTGCTATCGTCGAGGATGTTGTC CACGGCGACGGTGACGCGATTCATGCCATCACGCAGCGAGTT GTTGATTTCCGCTTCG | |
| BoGUS A-401-456T | 56 | CGCGTCACCGTCGCCGTGGACAACATCCTCGACGATAGCACC CTACCGGTGGGGCT | |
| BoGUS A-41-120B | 80 | CACTTCTCTTCCAGTCCTTTCCCGTAGTCCAGCTTGAAGTTC CAGACGCCATTGAGGTCGAAGACGCCACGGGTCTCGGT | |
| BoGUS A-6-40B | 35 | TTGATCGGGTACAGACTAGTCAGATCTACCATGGG | |
| BoGUS A-81-160T | 80 | ACTTCAAGCTGGACTACGGGAAAGGACTGGAAGAGAAGTGGT ACGAAAGCAAGCTGACCGACACTATTAGTATGGCCGTC | |
| BoGUS B-1-80T | 80 | GTACAGCGAGCGCCACGAAGAGGGCCTCGGAAAAGTCATTCG TAACAAGCCGAACTTCGACTTCTTCAACTATGCAGGCC | |
| BoGUS B-121-200B | 80 | CTTTGCCTTGAAAGTCCACCGTATAGGTCACAGTCCCGGTTG GGCCATTGAAGTCGGTCACAACCGAGATGTCCTCGACG | |
| BoGUS B-161-240T | 80 | ACCGGGACTGTGACCTATACGGTGGACTTTCAAGGCAAAGCC GAGACCGTGAAAGTGTCGGTCGTGGATGAGGAAGGCAA | |

TABLE 4-continued

| Oligonucleotide | Size | Sequence | SEQ ID NO |
|---|---|---|---|
| BoGUS B-201-280B | 80 | CTCCACGTTACCGCTCAGGCCCTCGGTGCTTGCGACCACTTT<br>GCCTTCCTCATCCACGACCGACACTTTCACGGTCTCGG | |
| BoGUS B-241-320T | 80 | AGTGGTCGCAAGCACCGAGGGCCTGAGCGGTAACGTGGAGAT<br>TCCGAATGTCATCCTCTGGGAACCACTGAACACGTATC | |
| BoGUS B-281-360B | 80 | GTCAGTCCGTCGTTCACCAGTTCCACTTTGATCTGGTAGAGA<br>TACGTGTTCAGTGGTTCCCAGAGGATGACATTCGGAAT | |
| BoGUS B-321-400T | 80 | TCTACCAGATCAAAGTGCAACTGGTGAACGACGGACTGACCA<br>TCGATGTCTATGAAGAGCCGTTCGGCGTGCGGACCGTG | |
| BoGUS B-361-440B | 80 | ACGGTTTGTTGTTGATGAGGAACTTGCCGTCGTTGACTTCCA<br>CGGTCCGCACGCCGAACGGCTCTTCATAGACATCGATG | |
| BoGUS B-401-480T | 80 | GAAGTCAACGACGGCAAGTTCCTCATCAACAACAAACCGTTC<br>TACTTCAAGGGCTTTGGCAAACATGAGGACACTCCTAT | |
| BoGUS B-41-120B | 80 | TACGTAAACGGGGTCGTGTAGATTTTCACCGGACGGTGCAGG<br>CCTGCATAGTTGAAGAAGTCGAAGTTCGGCTTGTTACG | |
| BoGUS B-441-520B | 80 | ATCCATCACATTGCTCGCTTCGTTAAAGCCACGGCCGTTGAT<br>AGGAGTGTCCTCATGTTTGCCAAAGCCCTTGAAGTAGA | |
| BoGUS B-481-555T | 75 | CAACGGCCGTGGCTTTAACGAAGCGAGCAATGTGATGGATTT<br>CAATATCCTCAAATGGATCGGCGCCAACAGCTT | |
| BoGUS B-5-40B | 36 | AATGACTTTTCCGAGGCCCTCTTCGTGGCGCTCGCT | |
| BoGUS B-521-559B | 39 | CCGGAAGCTGTTGGCGCCGATCCATTTGAGGATATTGAA | |
| BoGUS B-81-160T | 80 | TGCACCGTCCGGTGAAAATCTACACGACCCCGTTTACGTACG<br>TCGAGGACATCTCGGTTGTGACCGACTTCAATGGCCCA | |
| BoGUS C-1-80T | 80 | CCGGACCGCACACTATCCGTACTCTGAAGAGTTGATGCGTCT<br>TGCGGATCGCGAGGGTCTGGTCGTGATCGACGAGACTC | |
| BoGUS C-121-200B | 80 | GTTCACGGAGAACGTCTTGATGGTGCTCAAACGTCCGAATCT<br>TCTCCCAGGTACTGACGCGCTCGCTGCCTTCGCCGAGT | |
| BoGUS C-161-240T | 80 | ATTCGGACGTTTGAGCACCATCAAGACGTTCTCCGTGAACTG<br>GTGTCTCGTGACAAGAACCATCCAAGCGTCGTGATGTG | |
| BoGUS C-201-280B | 80 | CGCGCCCTCTTCCTCAGTCGCCGCCTCGTTGGCGATGCTCCA<br>CATCACGACGCTTGGATGGTTCTTGTCACGAGACACCA | |
| BoGUS C-241-320T | 80 | GAGCATCGCCAACGAGGCGGCGACTGAGGAAGAGGGCGCGTA<br>CGAGTACTTCAAGCCGTTGGTGGAGCTGACCAAGGAAC | |
| BoGUS C-281-360B | 80 | ACAAACAGCACGATCGTGACCGGACGCTTCTGTGGGTCGAGT<br>TCCTTGGTCAGCTCCACCAACGGCTTGAAGTACTCGTA | |
| BoGUS C-321-400T | 80 | TCGACCCACAGAAGCGTCCGGTCACGATCGTGCTGTTTGTGA<br>TGGCTACCCCGGAGACGGACAAAGTCGCCGAACTGATT | |
| BoGUS C-361-440B | 80 | CGAAGTACCATCCGTTATAGCGATTGAGCGCGATGACGTCAA<br>TCAGTTCGGCGACTTTGTCCGTCTCCGGGGTAGCCATC | |

TABLE 4-continued

| Oligonucleotide | Size | Sequence | SEQ ID NO |
|---|---|---|---|
| BoGUS C-401-489T | 89 | GACGTCATCGCGCTCAATCGCTATAACGGATGGTACTTCGAT GGCGGTGATCTCGAAGCGGCCAAAGTCCATCTCCGCCAGGAA TTTCA | |
| BoGUS C-41-120B | 80 | CCCGTGGTGGCCATGAAGTTGAGGTGCACGCCAACTGCCGGA GTCTCGTCGATCACGACCAGACCCTCGCGATCCGCAAG | |
| BoGUS C-441-493B | 53 | CGCGTGAAATTCCTGGCGGAGATGGACTTTGGCCGCTTCGAG ATCACCGCCAT | |
| BoGUS C-5-40B | 36 | ACGCATCAACTCTTCAGAGTACGGATAGTGTGCGGT | |
| BoGUS C-81-160T | 80 | CGGCAGTTGGCGTGCACCTCAACTTCATGGCCACCACGGGAC TCGGCGAAGGCAGCGAGCGCGTCAGTACCTGGGAGAAG | |
| BoGUS D-1-80T | 80 | CGCGTGGAACAAGCGTTGCCCAGGAAAGCCGATCATGATCAC TGAGTACGGCGCAGACACCGTTGCGGGCTTTCACGACA | |
| BoGUS D-121-200B | 80 | TCGCGAAGTCCGCGAAGTTCCACGCTTGCTCACCCACGAAGT TCTCAAACTCATCGAACACGACGTGGTTCGCCTGGTAG | |
| BoGUS D-161-240T | 80 | TTCGTGGGTGAGCAAGCGTGGAACTTCGCGGACTTCGCGACC TCTCAGGGCGTGATGCGCGTCCAAGGAAACAAGAAGGG | |
| BoGUS D-201-280B | 80 | GTGCGCGGCGAGCTTCGGCTTGCGGTCACGAGTGAACACGCC CTTCTTGTTTCCTTGGACGCGCATCACGCCCTGAGAGG | |
| BoGUS D-241-320T | 80 | CGTGTTCACTCGTGACCGCAAGCCGAAGCTCGCCGCGCACGT CTTTCGCGAGCGCTGGACCAACATTCCAGATTTCGGCT | |
| BoGUS D-281-360B | 89 | CGGTCACCAATTCACACGTGATGGTGATGGTGATGGCTAGCG TTCTTGTAGCCGAAATCTGGAATGTTGGTCCAGCGCTCGCGA AAGAC | |
| BoGUS D-321-373T | 53 | ACAAGAACGCTAGCCATCACCATCACCATCACGTGTGAATTG GTGACCGGGCC | |
| BoGUS D-41-120B | 80 | TACTCGACTTGATATTCCTCGGTGAACATCACTGGATCAATG TCGTGAAAGCCCGCAACGGTGTCTGCGCCGTACTCAGT | |
| BoGUS D-5-40B | 36 | GATCATGATCGGCTTTCCTGGGCAACGCTTGTTCCA | |
| BoGUS D-81-160T | 80 | TTGATCCAGTGATGTTCACCGAGGAATATCAAGTCGAGTACT ACCAGGCGAACCACGTCGTGTTCGATGAGTTTGAGAAC | |

The AI form of microbial GUS in pLITMUS 39 is transfected into KW1 host *E. coli* cells. Bacterial cells are collected by centrifugation, washed with Mg salt solution and resuspended in IMAC buffer (50 mM $Na_3PO_4$, pH 7.0, 300 mM KCl, 0.1% Triton® X-100, 1 mM PMSF). For hexa-His fusion proteins, the lysate is clarified by centrifugation at 20,000 rpm for 30 min and batch absorbed on a Ni-IDA-Sepharose column. The matrix is poured into a column and washed with IMAC buffer containing 75 mM imidazole. The β-glucuronidase protein bound to the matrix is eluted with IMAC buffer containing 10 mM EDTA.

If GUS is cloned without the hexa-His tail, the lysate is centrifuged at 50,000 rpm for 45 min, and diluted with 20 mM $NaPO_4$, 1 mM EDTA, pH 7.0 (buffer A). The diluted supernatant is then loaded onto a SP-Sepharose or equivalent column, and a linear gradient of 0 to 30% SP Buffer B (1 M NaCl, 20 mM $NaPO_4$, 1 mM EDTA, pH 7.0) in Buffer A with a total of 6 column volumes is applied. Fractions containing GUS are combined. Further purifications can be performed.

Example 7

Muteins of Codon Optimized β-glucuronidase

Muteins of the codon-optimized GUS genes are constructed. Each of the four GUS genes described above, A0, AI, AII, and AIII, contain none, one, or four amino acid alterations. The muteins that contain one alteration have a Leu 141 to His codon change. The muteins that contain four alterations have the Leu 141 to His change as well as Val 138 to Ala, Tyr 204 to Asp, and Thr 560 to Ala changes. pLITMUS 39 containing these 12 muteins are transfected into KW1. Colonies are tested for secretion of the introduced GUS gene by staining with X-GlcA. A white colony indicates undetectable GUS activity, a light blue colony indicates some detectable activity, and a dark blue colony indicates a higher level of detectable activity. As shown in Table 5 below, when GUS has the four mutations, no GUS activity is detectable. When GUS has a single Leu 141 to His mutation, three of the four constructs exhibit no GUS activity, while the AI construct exhibits a low level of GUS activity. All constructs exhibit GUS activity when no mutations are present. Thus, the Leu 141 to His mutation dramatically affects the activity of GUS.

TABLE 5

| Number of Mutations | GUS construct A0 | AI | AII | AIII |
|---|---|---|---|---|
| 4 | white | white | white | white |
| 1 | white | light blue | white | white |
| 0 | light blue | dark blue | light blue | light blue |

Example 8

Expression of Microbial β-glucuronidases In Yeast, Plants and *E. coli*

A series of expression vector constructs of three different GUS genes, *E. coli* GUS, *Bacillus* GUS, and the A0 version of codon-optimized *Bacillus* GUS, are prepared and tested for enzymatic activity in *E. coli*, yeast, and plants (rice, Millin variety). The GUS genes are cloned in vectors that either contain a signal peptide suitable for the host or do not contain a signal peptide. The *E. coli* vector contains a sequence encoding a pelB signal peptide, the yeast vectors contain a sequence encoding either an invertase or Mat alpha signal peptide, and the plant vectors contain a sequence encoding either a glycine-rich protein (GRP) or extensin signal peptide.

```
ATGCTTTTGC AAGCCTTCCT TTTCCTTTTG GCTGGTTTTG CAGCCAAAAT ATCTGCAATG  (SEQ ID NO.___)

Mat alpha signal sequence:
ATGAGATTTC CTTCAATTTT TACTGCAGTT TTATTCGCAG CATCCTCCGC ATTAGCTGCT  (SEQ ID NO.___)

CCAGTCAACA CTACAACAGA AGATGAAACG GCACAAATTC CGGCTGAAGC TGTCATCGGT

TACTTAGATT TAGAAGGGGA TTTCGATGTT GCTGTTTTGC CATTTTCCAA CAGCACAAAT

AACGGGTTAT TGTTTATAAA TACTACTATT GCCAGCATTG CTGCTAAAGA AGAAGGGGTA

TCTTTGGATA AAAGAGAG

Extensin signal sequence
CATGGGAAAA ATGGCTTCTC TATTTGCCAC ATTTTTAGTG GTTTTAGTGT CACTTAGCTT  (SEQ ID NO.___)

AGCTTCTGAA AGCTCAGCAA ATTATCAA

GRP signal sequence
CATGGCTACT ACTAAGCATT TGGCTCTTGC CATCCTTGTC CTCCTTAGCA TTGGTATGAC  (SEQ ID NO.___)

CACCAGTGCA AGAACCCTCC TA
```

The GUS genes are cloned into each of these vectors using standard recombinant techniques of isolation of a GUS-gene containing fragment and ligation into an appropriately restricted vector. The recombinant vectors are then transfected into the appropriate host and transfectants are tested for GUS activity.

As shown in the Table below, all tested transfectants exhibit GUS activity (indicated by a +). Moreover, similar results are obtained regardless of the presence or absence of a signal peptide.

TABLE 6

| | *E. coli* | | Yeast | | | Plants | | |
|---|---|---|---|---|---|---|---|---|
| GUS | No SP* | pelB | No SP | Invertase | Mat α | No SP | GRP | Extensin |
| *E. coli* GUS | + | NT | + | + | + | + | + | + |
| Bacillus GUS | + | NT | + | + | + | + | + | + |

*SP = signal peptide

Example 9

Elimination of the Potential N-glycosylation Site of *Bacillus* β-glucuronidase The consensus N-glycosylation sequence Asn-X-Ser/Thr is present in *Bacillus* GUS at amino acids 118–120, Asn-Asn-Ser (FIGS. 3A–B). Glycosylation could interfere with secretion or activity of β-glucuronidase upon entering the ER. To remove potential N-glycosylation, the Asn at residue 118 is changed to another amino acid in the plasmid pTANE95m (AI) is altered. The GUS in this plasmid is a synthetic GUS gene with a completely native 5' end.

The oligonucleotides Asn-T, 5'-A TTC CTG CCA TTCGAGGCG GAA ATC NNG AAC TCG CTG CGT GAT-3' (SEQ ID NO: 111) and Asn-B, 5'-ATC ACG CAG CGA GTT CNN GAT TTC CGC CTC GAA TGG CAG GAA T-3' (SEQ ID NO: 112), are used in the "quikchange" mutagenesis method by Stratagene (La Jolla, Calif.) to randomize the first two nucleotides of the Asn 118 codon, AAC. The third base is changed to a G nucleotide, so that reversion to Asn is not possible. In theory a total of 13 different amino acids are created at position 118.

Because expression of GUS from the plasmid pTANE95m (AI) exhibits a range of colony phenotypes from white to dark blue, a restriction enzyme digestion assay is used to confirm presence of mutants. Therefore, an elimination of a BstB I restriction site which does not change any amino acid, is also introduced into the mutagenizing oligonucleotides to facilitate restriction digestion screening of mutants.

Sixty colonies were randomly picked and assayed by BstB I digestion. Twenty-one out of the 60 colonies have the BstB I site removed and are thus mutants. DNA sequence analysis of these candidate mutants show that a total of 8 different amino acids are obtained. Five of the N 118 mutants are chosen as suitable for further experimentation. In these mutants, the N 118 residue is changed to a Ser, Arg, Leu, Pro, or Met.

Example 10

Expression of β-glucuronidase in Transgenic Rice Plants

Microbial GUS can be used as a non-destructible marker. In this example, transgenic rice expressing a GUS gene encoding a secreted form are assayed for GUS expression in planta.

Seeds of T0 plants, which are the primary transformed plants, from pTANG86.1/2/3/4/5/6 (see Table 7 below) transformed plants, seeds of pCAM1301 (*E. coli* GUS with N358-Q change to remove N-glycosylation signal sequence) transformed plants, or untransformed Millin rice seeds are germinated in water containing 1 mM MUG or 50 μg/mL X-GlcA with or without hygromycin (for nontransformed plants). Resulting plants are observed for any reduced growth due to the presence of MUG, X-GlcA. No toxic effects of X-GlcA are detected, but roots of the plants grown in MUG are somewhat stunted.

For assaying GUS activity in planta, seeds are germinated in water with or without hygromycin (for nontransformed plants). Roots of the seedlings are submerged in water containing 1 mM MUG, or 50 μg/mL X-GlcA. Fluorescence (in the case of MUG staining) or indigo dye (in the case of X-GlcA staining) are assayed in the media and roots over time.

Secondary roots from seedlings of pTANG86.3 and pTANG86.5 (BoGUS fused with signal peptides) plants show indigo color after ½ hour incubation in water containing X-GlcA. Evidence that GUS is a non-destructive marker is obtained by plant growth after transferring the stained plant to water. Furthermore, stained roots also grow further.

Example 11

Expression of β-glucuronidase in Yeast

All the yeast plasmids are based on the Ycp backbone, which contains a yeast centromere and is stable at low copy number. Yeast strain InvSc1 (mat α his3-Δ1 leu2 trp1-289 ura3-52) from Invitrogen (Carlsbad, Calif.) is transformed with the *E. coli* GUS and *Bacillus* GUS plasmids indicated in the table below. Transformants are plated on both selection media (minimal media supplemented with His, Leu, Trp, and 2% glucose as a carbon source to suppress the expression of the gene driven by the gal1 promoter) and expression media (media supplemented with His, Leu, Trp, 1% raffinose, 1% galactose as carbon source and with 50 pg/ml X-GlcA).

TABLE 7

| | Yeast | | | Plants | | |
|---|---|---|---|---|---|---|
| | No SP | Invertase | Mat alpha | No SP | GRP | Extensin |
| *E. coli* | pAKD80.3 | pAKD80.6 | pTANG87.4 | pTANG86.2 | pTANG86.4 | pTANG86.6 |
| Syn BGUS | pTANG87.1 | pTANG87.2 | pTANG87.3 | pTANG86.1 | pTANG86.3 | pTANG86.5 |
| Nat BGUS | pAKD102.1 | pAKE2.1 | pAKE11.4 | pAKD40 | pAKC30.1 | pAKC30.3 |

With the exception of pAKD80.6, all other transformed yeast colonies are white on X-GlcA plates. The transformants do express GUS, however, which is evidenced by lysing the cells on the plates with hot agarose containing X-GlcA and observing the characteristic indigo color. The yeast transformants are white when GUS is not secreted, as X-GlcA cannot be taken by the yeast cell. All the yeast colonies transformed with pAKD80.6 are blue on X-GlcA plates and have a blue halo around each colony, clearly indicating that the enzyme is secreted into the medium.

*Bacillus* GUS enzyme has a potential N-glycosylation site, which may interfere with the secretion process or cause inactivation of the enzyme upon secretion. To determine whether the N-glycosylation site has a deleterious effect, on secretion, yeast colonies are streaked on expression plates containing X-GlcA and from 0.1 to 20 μg/ml of tunicamycin (to inhibit all N-glycosylation). At high concentrations of tunicamycin (5, 10, and 20 μg/ml), yeast colonies do not grow, likely due to toxicity of the drug. However, in yeast transformed with pTANG87.3, the cells that do survive at these tunicamycin concentrations are blue. This indicates that glycosylation may affect the secretion or activity of *Bacillus* GUS. Any effect should be overcome by mutating the glycosylation signal sequence as described.

Example 12

Expression of Low-Cysteine *E. coli* β-glucuronidase

The *E. coli* GUS protein has nine cysteine residues, whereas, human GUS has four and *Bacillus* GUS has one.

Low-cysteine muteins of *E. coli* GUS are constructed to provide a form of EcGUS that is secretable.

Single and multiple Cys muteins are constructed by site-directed mutagenesis techniques. Eight of the nine cysteine residues in *E. coli* GUS are changed to the corresponding residue found in human GUS based on alignment of the two protein sequences. One of the *E. coli* GUS cysteine residues, amino acid 463, aligns with a cysteine residue in human GUS and was not altered. The corresponding amino acids between *E. coli* GUS and human GUS are shown below.

TABLE 8

| Identifier | EcGUS Cys residue no. | Human GUS corresponding amino acid |
|---|---|---|
| A | 28 | Asn |
| B | 133 | Ala |
| C | 197 | Ser |
| D | 253 | Glu |
| E | 262 | Ser |
| F | 442 | Phe |
| G | 448 | Tyr |
| H | 463 | Cys |
| I | 527 | Lys |

The mutein GUS genes are cloned into a pBS backbone. The mutations are confirmed by diagnostic restriction site changes and by DNA sequence analysis. Recombinant vectors are transfected into KW1 and GUS activity assayed by staining with X-GICA (5-bromo-4-chloro-3-indolyl-β-D-glucuronide).

As shown in the Table below, when the Cys residues at 442 (F), 448 (G), and 527 (I) are altered, GUS activity is greatly or completely diminished. In contrast, when the N-terminal five Cys residues (A, B, C, D, and E) are altered, GUS activity remains detectable.

TABLE 9

| Cys changes | GUS activity |
|---|---|
| A | Yes |
| B | Yes |
| C | Yes |
| I | No |
| D, E | Yes |
| F, G | No |
| C, D, E | Yes |
| B, C, D, E | Yes |
| A, B, C, D, E | Yes |
| A, B, C, D, E, I | No |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A recombinant microbial β-glucuronidase, wherein the β-glucuronidase is encoded by a nucleic acid molecule comprising nucleotides 1–1689 of FIGS. 4I–J (SEQ ID NO: 14) or by a nucleic acid molecule that hybridizes under stringent conditions to the complement of nucleotides 1–1689 of FIGS. 4I–J (SEQ ID NO: 14) and which encodes a functional β-glucuronidase, wherein stringent conditions include a solution comprising 5×SSPE and 0.5% SDS and a hybridization temperature of 65° C.

2. A recombinant β-glucuronidase, comprising the amino acid sequences of FIG. 5B SEQ ID NOs: 18–23, or a variant thereof, and which encodes a functional β-glucuronidase, wherein the variant has at least 75% amino acid identity.

3. A recombinant microbial β-glucuronidase, wherein the β-glucuronidase is encoded by one of a nucleic acid molecule comprising SEQ ID NOs: 7–13 or by a nucleic acid molecule that hybridizes under stringent conditions to the complement of SEQ ID NOs: 7–13 and which encodes a functional β-glucuronidase, wherein stringent conditions include a solution comprising 5×SSPE and 0.5% SDS and a hybridization temperature of 65° C.

* * * * *